US011358930B2

(12) United States Patent
Wipf

(10) Patent No.: US 11,358,930 B2
(45) Date of Patent: Jun. 14, 2022

(54) SELECTIVE POTASSIUM CHANNEL AGONISTS

(71) Applicant: University of Pittsburgh—Of the Commonwealth System of Higher Education, Pittsburgh, PA (US)

(72) Inventor: Peter Wipf, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 60 days.

(21) Appl. No.: 17/048,878

(22) PCT Filed: Mar. 8, 2019

(86) PCT No.: PCT/US2019/021398
§ 371 (c)(1),
(2) Date: Oct. 19, 2020

(87) PCT Pub. No.: WO2019/203951
PCT Pub. Date: Oct. 24, 2019

(65) Prior Publication Data

US 2021/0238129 A1 Aug. 5, 2021

Related U.S. Application Data

(60) Provisional application No. 62/660,751, filed on Apr. 20, 2018.

(51) Int. Cl.

| | |
|---|---|
| ***C07C 271/26*** | (2006.01) |
| ***C07C 271/38*** | (2006.01) |
| ***C07D 213/38*** | (2006.01) |
| ***C07D 213/61*** | (2006.01) |
| ***A61P 27/16*** | (2006.01) |
| ***A61P 25/08*** | (2006.01) |

(52) U.S. Cl.
CPC ............ *C07C 271/26* (2013.01); *A61P 25/08* (2018.01); *A61P 27/16* (2018.01); *C07C 271/38* (2013.01); *C07D 213/38* (2013.01); *C07D 213/61* (2013.01)

(58) Field of Classification Search
CPC ..... C07C 271/26; C07C 271/38; C07D 13/38; C07D 13/61; A61P 27/16; A61P 25/08
See application file for complete search history.

(56) References Cited

U.S. PATENT DOCUMENTS

| | | | |
|---|---|---|---|
| 5,384,330 A | 1/1995 | Dieter et al. | |
| 6,348,486 B1 | 2/2002 | Argentieri et al. | |
| 8,916,133 B2 | 12/2014 | Duggan et al. | |
| 10,526,280 B2 | 1/2020 | Wipf et al. | |
| 2002/0111379 A1 | 8/2002 | Bowlby et al. | |
| 2002/0183395 A1 | 12/2002 | Argentieri et al. | |
| 2013/0287686 A1 | 10/2013 | Duggan et al. | |
| 2018/0127357 A1* | 5/2018 | Wipf ..................... | C07C 381/00 |

FOREIGN PATENT DOCUMENTS

| | | |
|---|---|---|
| WO | WO 01/01970 A2 | 1/2001 |
| WO | WO 2004/058739 A1 | 7/2004 |
| WO | WO 2007/090409 A1 | 8/2007 |
| WO | WO 2009/015667 A1 | 2/2009 |
| WO | WO 2013/007698 A1 | 1/2013 |
| WO | WO 2016/077724 A1 | 5/2016 |

OTHER PUBLICATIONS

CAS Registry No. 400010-61-9 cited in Written Opinion issued for International Application No. PCT/US2015/060627 in reference to WO 02/49628 published Jun. 27, 2002.
CAS Registry No. 400010-62-0 cited in Written Opinion issued for International Application No. PCT/US2015/060627 in reference to WO 02/49628 published Jun. 27, 2002.
CAS Registry No. 400010-63-1 cited in Written Opinion issued for International Application No. PCT/US2015/060627 in reference to WO 02/49628 published Jun. 27, 2002 and WO 2004/058739 published Jul. 15, 2004.
CAS Registry No. 400010-64-2 or cited in Written Opinion issued for International Application No. PCT/US2015/060627 in reference to WO 02/49628.

(Continued)

*Primary Examiner* — Timothy R Rozof
(74) *Attorney, Agent, or Firm* — Klarquist Sparkman, LLP

(57) ABSTRACT

Selective potassium channel agonists and methods of use thereof are disclosed. A compound, or a pharmaceutically acceptable salt thereof, having a formula I (I)

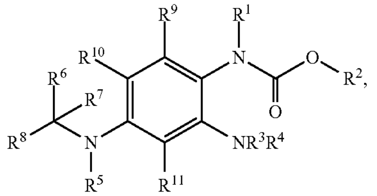

wherein $R^1$ is H or optionally-substituted alkyl; $R^2$ is optionally-substituted $C_1$-$C_6$ alkyl or optionally-substituted cyclopropyl; $R^3$ and $R^4$ are each independently H or optionally-substituted alkyl; $R^5$ is H, optionally-substituted alkyl, acyl, or alkoxycarbonyl; $R^6$ and $R^7$ are each independently H, optionally-substituted alkyl, or $R^6$ and $R^7$ together form a carbocycle; $R^8$ is substituted phenyl or optionally-substituted pyridinyl, provided that if $R^8$ is substituted phenyl, then $R^2$ is optionally-substituted cyclopropyl; and $R^9$, $R^{10}$ and $R^{11}$ are each independently H, halo, or optionally-substituted alkyl.

18 Claims, 9 Drawing Sheets

(56) References Cited

OTHER PUBLICATIONS

CAS Registry No. 945828-50-2 cited in Written Opinion issued for International Application No. PCT/US2015/060627 in reference to WO 2009/015667 published Feb. 5, 2009, and WO 2007/090409 published Aug. 16, 2007.
Cederroth, et al., "Hearing loss and tinnitus—are funders and industry listening?" *Nature Biotechnology*, vol. 31, pp. 972-974, Nov. 8, 2013.
Damgaard et al., "Extrasynaptic $GABA_A$ receptor activation reverses recognition memory deficits in an animal model of schizophrenia," *Psychopharmacology*, 214(2): 403-413, 2011.
Hoestgaard-Jensen, et al., "Pharmacological characterization of a novel positive modulator at $\alpha_4\beta_3\delta$-containing extrasynaptic $GABA_A$ receptors," Neuropharmacology, 58(4): 702-711, 2010.
Hu et al., "Discovery of a retigabine derivative that inhibits KCNQ2 potassium channels," *Acta Pharmacologica Sinica*, 34(10):1359, May 31, 2013.
International Search Report and Written Opinion issued for International Application No. PCT/US2015/060627 dated Jan. 28, 2016.
International Search Report and Written Opinion issued for International Application No. PCT/US2019/021398 dated May 26, 2019.
Kumar et al., "Synthesis and evaluation of potent KCNQ2/3—specific channel activators," *Molecular Pharmacology*, 89(6):667-677, 2016.
Li et al., "Pathogenic plasticity of Kv7.2/3 channel activity is essential for the induction of tinnitus," *Proceedings of the National Academy of Sciences of the United States of America*, 110(24): 9980-9985, Jun. 11, 2013.
Oak et al., "Voltage-gated $K^+$channels contributing to temporal precision at the inner hair cell-auditory afferent nerve fiber synapses in the mammalian cochlea," *Arch. Pharm. Res.*, 37(7): 821-833, Jul. 2014.
Office Action, dated Nov. 26, 2018, issued in U.S. Appl. No. 15/526,668.
Office Action, dated Apr. 16, 2019, issued in U.S. Appl. No. 15/526,668.
Vardya et al., "Positive modulation of δ-subunit containing $GABA_A$ receptors in mouse neurons," *Neuropharmacology*, 63(3): 469-479, 2012.

* cited by examiner

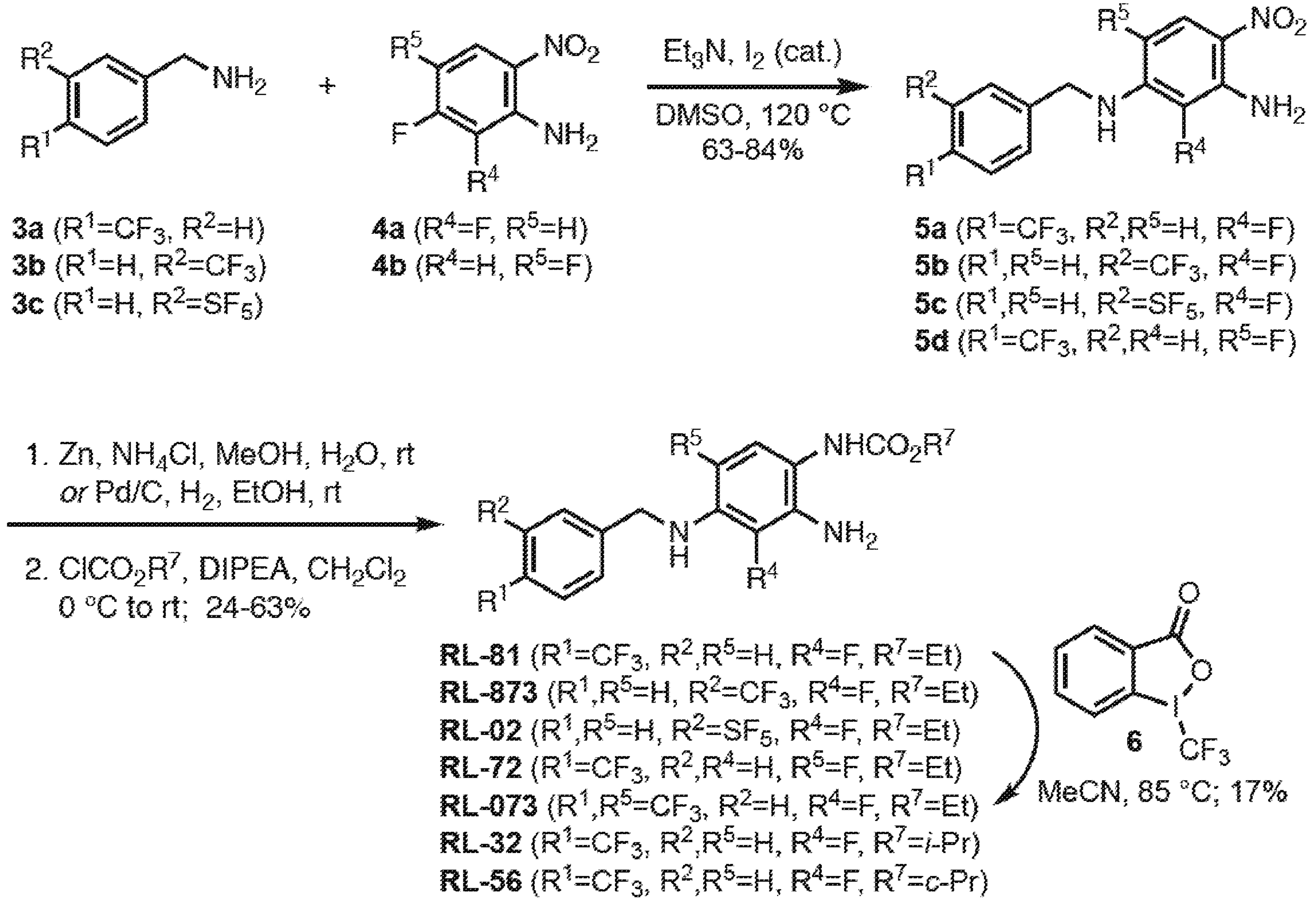

RL-23 (X=N, Y=CCN, $R^7$=Et)

3h + 4f → 5n

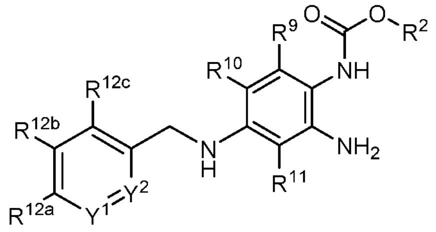

| Cpd | $Y^1$ | $Y^2$ | $R^{12a}$ | $R^{12b}$ | $R^{12c}$ | $R^9$ | $R^{10}$ | $R^{11}$ | $R^2$ | $K_v7.2/3$ $EC_{2x}$±SD [µM] | $K_v7.3/5$ $EC_{2x}$±SD [µM] | $K_v7.4$ $EC_{2x}$±SD [µM] | $K_v7.4/5$ $EC_{2x}$±SD [µM] | SI |
|---|---|---|---|---|---|---|---|---|---|---|---|---|---|---|
| FP | CH | CH | F | H | H | H | H | N* | Et | 2.00±0.69 | 1.58±0.69 | 5.62±1.86 | 3.50±2.68 | 1.8 |
| RG | CH | CH | F | H | H | H | H | H | Et | 0.33±0.08 | 0.34±0.04 | ND | ND | ND |
| RL-81 | CH | CH | $CF_3$ | H | H | H | H | F | Et | 0.26±0.13 | 0.29±0.06 | 0.10±0.04 | 0.09±0.04 | 0.3 |
| RL-73 | CH | CH | H | $CF_3$ | H | H | H | F | Et | 0.14±0.05 | 0.20±0.08 | 0.40±0.13 | 0.66±0.01 | 4.7 |
| RL-02 | CH | CH | H | $SF_5$ | H | H | H | F | Et | 0.36±0.25 | 0.21±0.11 | 0.65±0.39 | 0.65±0.28 | 1.8 |
| RL-72 | CH | CH | $CF_3$ | H | H | H | F | H | Et | 1.26±0.31 | >10 | 4.65±0.95 | >10 | >7 |
| RL-073 | CH | CH | $CF_3$ | H | H | H | $CF_3$ | F | Et | >10 | >10 | >10 | >10 | ND |
| RL-32 | CH | CH | $CF_3$ | H | H | H | H | F | i-Pr | 0.16±0.11 | 0.16±0.10 | 0.19±0.10 | 4.98±1.12 | 31 |
| RL-56 | CH | CH | $CF_3$ | H | H | H | H | F | c-Pr | 0.11±0.02 | 0.23±0.10 | 0.38±0.30 | 0.28±0.03 | 2.5 |
| RL-18 | CH | CF | $CF_3$ | H | H | H | H | F | Et | 0.18±0.11 | 0.34±0.01 | 0.11±0.04 | 0.30±0.26 | 1.7 |
| RL-35 | CH | CF | $CF_3$ | H | H | H | H | F | c-Pr | 0.59±0.08 | 0.47±0.01 | 0.21±0.19 | 0.35±0.17 | 0.6 |
| RL-36 | CH | CF | $CF_3$ | H | H | H | F | F | c-Pr | 0.93±0.21 | >10 | >10 | >10 | >10 |
| RL-46 | CH | CF | $CF_3$ | H | H | F | H | F | c-Pr | 1.47±0.22 | >10 | 0.55±0.14 | >10 | >7 |

*C-$R^{11}$ replaced by ring N; Et = ethyl, i-Pr = isopropyl, c-Pr = cyclopropyl

FIG. 5A

| Cpd | $Y^1$ | $Y^2$ | $R^{12a}$ | $R^{12b}$ | $R^{12c}$ | $R^9$ | $R^{10}$ | $R^{11}$ | $R^2$ | $K_v7.2/3$ $EC_{2x}$±SD [μM] | $K_v7.3/5$ $EC_{2x}$±SD [μM] | $K_v7.4$ $EC_{2x}$±SD [μM] | $K_v7.4/5$ $EC_{2x}$±SD [μM] | SI |
|---|---|---|---|---|---|---|---|---|---|---|---|---|---|---|
| RL-50 | CH | CF | $CF_3$ | H | H | F | F | F | c-Pr | >10 | >10 | >10 | >10 | ND |
| RL-31 | CH | N | $CF_3$ | H | H | H | H | F | Et | 0.66±0.25 | 0.79±0.26 | 0.85±0.14 | 0.59±0.34 | 0.9 |
| RL-68 | CH | N | $CF_3$ | H | H | H | H | F | c-Pr | 0.79±0.03 | 0.72±0.05 | 0.90±0.02 | 0.96±0.05 | 1.2 |
| RL-96 | CH | N | $CF_3$ | H | F | H | H | F | c-Pr | 1.39±0.20 | >10 | >10 | >10 | >7 |
| RL-01 | CH | N | $CF_3$ | H | F | H | F | F | c-Pr | >10 | >10 | >10 | >10 | ND |
| RL-12 | CH | N | $CF_3$ | H | F | F | H | F | c-Pr | 1.00±0.50 | >10 | >10 | >10 | >10 |
| RL-23 | CCN | N | $CF_3$ | H | H | H | H | F | Et | 1.60±0.19 | 1.30±0.16 | 2.17±0.37 | 2.33±0.89 | 1.5 |
| RL-24 | N | CH | $CF_3$ | H | H | H | H | F | Et | 0.61±0.34 | 0.69±0.35 | 0.95±0.13 | 1.27±0.05 | 2.1 |
| RL-67 | N | CH | $CF_3$ | H | H | H | H | F | c-Pr | 0.71±0.23 | 0.69±0.19 | 1.13±0.72 | 1.36±0.70 | 1.9 |

| Compound ID | Primary SP | | Primary CRC | | Secondary | | | |
|---|---|---|---|---|---|---|---|---|
| | hKCNQ2/3 FluxOR Ag SP | NV-KCNQ2/3 IW-Barracuda ag/pot SP | NV-KCNQ2/3 IW-Barracuda ag/pot CRC | | NV-KCNQ3/5 IW-Barracuda ag/pot CRC | | NV-KCNQ2/3 IW-Barracuda INH CRC | NV-KCNQ3/5 IW-Barracuda INH CRC |
| | %Stim @ 10μM | Delta V0.5 | Conc @ 2xG(.15) (μM) | Delta V0.5 (μM) | Conc @ 2xG(.15) (μM) | Delta V0.5 (μM) | Rel IC50 (μM) | Rel IC50 (μM) |
| UPCMLD34AMZK041521 | 116.1<br>86.74 | -22.7<br>-27.13 | 2.237<br>2.082<br>3.027 | -21.22<br>-18.87<br>-21.26 | 2.353<br>2.306<br>2.889 | -4.482<br>-8.39<br>-9.431 | >10.0 | >10.0 |
| NR561-045 | 117.5<br>120.0 | -40.78<br>-38.65 | 1.251<br>0.2502<br>1.095 | -39.49<br>-38.61<br>-36.29 | 0.7946<br>0.3993 | -18.62<br>-22.88 | >10.0 | >10.0 |
| NR579-046 | 104.2<br>81.79 | -43.38<br>-35.56 | 0.5009<br>0.3671<br>0.3416 | -36.65<br>-34.63<br>-39.21 | 0.5287<br>0.3912 | -19.52<br>-22.26 | >10.0 | >10.0 |
| RL648-073 | 96.92<br>98.79 | -43.37<br>-34.47 | 0.123<br>0.1292<br>0.0927 | -34.66<br>-32.79<br>-37.26 | 0.1849<br>0.115 | -18.63<br>-24.75 | >10.0 | >10.0 |
| RL673-002 | 101.7<br>87.0 | -36.35<br>-39.53 | 0.355<br>0.08489<br>0.1625 | -38.64<br>-31.68<br>-30.95 | 0.3312<br>0.08452 | -14.97<br>-28.55 | >10.0 | >10.0 |

FIG. 6A

| Compound ID | Primary SP | | Primary CRC | | Secondary | | | |
|---|---|---|---|---|---|---|---|---|
| | hKCNQ2/3 FluxOR Ag SP | NV-KCNQ2/3 IW-Barracuda ag/pot SP | NV-KCNQ2/3 IW-Barracuda ag/pot CRC | | NV-KCNQ3/5 IW-Barracuda ag/pot CRC | | NV-KCNQ2/3 IW-Barracuda INH CRC | NV-KCNQ3/5 IW-Barracuda INH CRC |
| | %Stim @ 10μM | Delta V0.5 | Conc @ 2xG(.15) (μM) | Delta V0.5 (μM) | Conc @ 2xG(.15) (μM) | Delta V0.5 (μM) | Rel IC50 (μM) | Rel IC50 (μM) |
| RL702-018 | 105.5<br>104.1 | -41.55<br>-42.31 | 0.09482<br>0.1054<br>0.1577 | -34.87<br>-40.21<br>-39.49 | 0.04645 | -24.9 | >10.0 | |
| RL702-024 | 111.3<br>109.3 | -42.73<br>-38.34 | 1.04<br>0.3388<br>0.233 | -38.93<br>-38.38<br>-39.27 | 1.069<br>0.3672 | -14.64<br>-13.62 | >10.0 | >10.0 |
| RL702-031 | 99.35<br>76.71 | -37.97<br>-40.65 | 0.6334<br>0.4757<br>0.3958 | -34.92<br>-30.05<br>-41.29 | 0.5373<br>0.3299 | -26.48<br>-22.02 | | |
| RL702-032 | 101.9<br>90.46 | -41.75<br>-37.57 | 0.1296<br>0.1122<br>0.09127 | -41.68<br>-29.29<br>-32.07 | 0.1366<br>0.04372 | -32.21<br>-13.98 | >10.0 | >10.0 |
| RL702-056 | 112.1<br>106.5 | -46.01<br>-41.8 | 0.1117<br>0.09588<br>0.1162 | -34.32<br>-42.18<br>-39.06 | 0.1725<br>0.06978 | -20.3<br>-17.57 | >10.0 | >10.0 |

FIG. 6B

Top= RL-81
Middle = RL-50
Bottom = RL46
Colors range from +170 kJ/mol (blue) to -310 kJ/mol (red)

SELECTIVE POTASSIUM CHANNEL AGONISTS

CROSS REFERENCE TO RELATED APPLICATIONS

This is the U.S. National Stage of International Application No. PCT/US2019/021398, filed Mar. 8, 2019, which was published in English under PCT Article 21(2), which in turn claims the benefit of the earlier filing date of U.S. Provisional Application No. 62/660,751, filed Apr. 20, 2018, each of which is incorporated herein by reference in its entirety.

ACKNOWLEDGMENT OF GOVERNMENT SUPPORT

This invention was made with government support under grants #W81XWH-14-1-0117 and W81XWH1810623, awarded by the ARMY/MRMC (US Army Medical Research and Material Command) U.S. Department of Defense. The government has certain rights in the invention.

FIELD

Selective potassium channel agonists and methods of use thereof are disclosed.

BACKGROUND

Decreased inhibitory and/or increased excitatory input are thought to generate the hyperexcitability observed in the neuronal pathways of epilepsy and tinnitus. A decrease in KCNQ2/3 (Kv7.2/Kv7.3) channel activity leads to hyperexcitable auditory brainstem circuits, which in turn promote epilepsy and tinnitus. In contrast, the pharmacological activation of KCNQ2/3 (Kv7.2/Kv7.3) channels prevents these pathologies. Therefore, KCNQ2/3 (Kv7.2/Kv7.3) channels provide a novel target for developing a treatment for epilepsy and tinnitus.

SUMMARY

Embodiments of selective potassium channel agonists and methods of use thereof are disclosed. In one embodiment, a selective potassium channel agonist, or a pharmaceutically acceptable salt thereof, has a formula I:

(I)

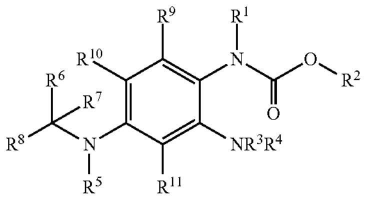

wherein $R^1$ is H or optionally-substituted alkyl; $R^2$ is optionally-substituted linear or branched $C_1$-$C_6$ alkyl or optionally-substituted cyclopropyl; $R^3$ and $R^4$ are each independently H or optionally-substituted alkyl; $R^5$ is H, optionally-substituted alkyl, acyl, or alkoxycarbonyl; $R^6$ and $R^7$ are each independently H, optionally-substituted alkyl, or $R^6$ and $R^7$ together form a carbocycle; $R^8$ is substituted phenyl or optionally-substituted pyridinyl, provided that if $R^8$ is substituted phenyl, then $R^2$ is optionally-substituted cyclopropyl; and $R^9$, $R^{10}$ and $R^{11}$ are each independently H, halo, or optionally-substituted alkyl.

In another embodiment, a selective potassium channel agonist, or a pharmaceutically acceptable salt thereof, has a formula II:

(II)

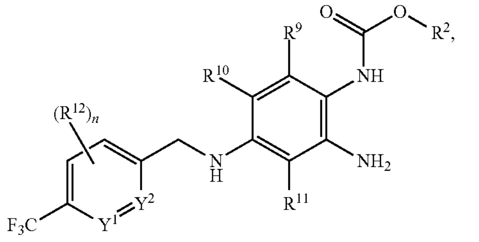

wherein $Y^1$ and $Y^2$ independently are CH, CX where X is halo, N, or CCN, provided that at least one of $Y^1$ and $Y^2$ is CH or CX; $R^{12}$ is halo or substituted sulfanyl, and n is 0, 1, or 2, and wherein if $Y^1$ and $Y^2$ independently are CH or CX, then $R^2$ is cyclopropyl.

In one example, one of $Y^1$ and $Y^2$ is N, the other of $Y^1$ and $Y^2$ is CH or CCN; and $R^2$ is ethyl or cyclopropyl. In another example, $Y^1$ and $Y^2$ independently are CH or CX, and the compound has a formula III:

(III)

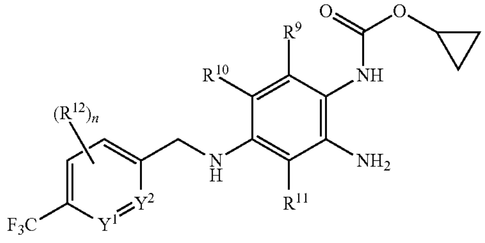

.

Embodiments of a method of activating a potassium channel include contacting the potassium channel with an effective amount of at least one compound as disclosed herein or a pharmaceutical composition comprising at least one compound as disclosed herein. In some embodiments, the potassium channel is KCNQ2/3. Contacting the potassium channel with an effective amount of the compound or pharmaceutical composition may comprise administering the effective amount of the compound or pharmaceutical composition to a subject.

In one embodiment, a method of treating a subject suffering from or susceptible to a condition that is ameliorated by KCNQ2/3 channel activation includes administering to the subject a therapeutically effective amount of at least one compound as disclosed herein or a pharmaceutical composition comprising at least one compound as disclosed herein. In some examples, the condition is tinnitus or epilepsy.

In another embodiment, a method of treating a subject suffering from or susceptible to tinnitus or epilepsy, comprises administering to the subject a therapeutically effective amount of at least one compound as disclosed herein or a pharmaceutical composition comprising at least one compound as disclosed herein.

The foregoing and other objects, features, and advantages of the invention will become more apparent from the following detailed description, which proceeds with reference to the accompanying figures.

BRIEF DESCRIPTION OF THE DRAWINGS

FIGS. 1-4 are exemplary synthetic schemes for preparing several embodiments of the disclosed compounds.

FIGS. 5A and 5B are tables showing biological activity of several disclosed compounds.

FIGS. 6A and 6B are tables showing biological activity of several additional disclosed compounds.

DETAILED DESCRIPTION

I. Definitions and Abbreviations

Figure 2:
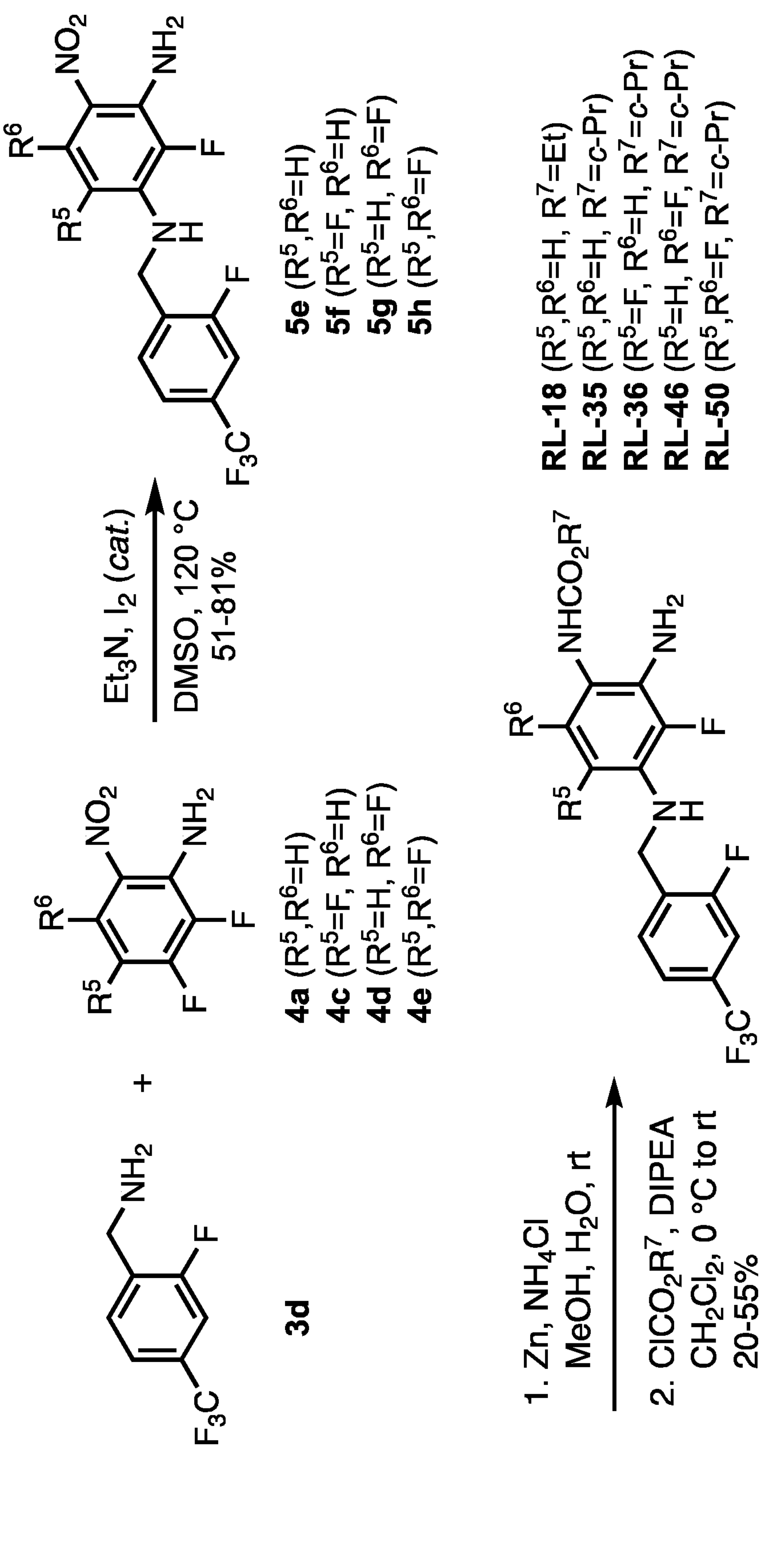

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, hydrogen, optionally substituted alkyl, optionally substituted cycloalkyl, optionally substituted heterocycloalkyl, optionally substituted aryl, or optionally substituted heteroaryl. "Lower acyl" groups are those that contain one to six carbon atoms.

"Administration" as used herein is inclusive of administration by another person to the subject or self-administration by the subject.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, heterocycloalkyl, heteroaryl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aminoalkyl" refers to alkyl groups as defined above where at least one hydrogen atom is replaced with an amino group (e.g., $—CH_2—NH_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

"Carbocycle" refers to a saturated or unsaturated cyclic radical of 3 to 8 ring atoms in which each of the ring atoms are carbon. Such carbocyclic groups may be optionally substituted independently with one, two or three substituents selected from alkyl, heteroalkyl, haloalkyl, cycloalkyl, cycloalkylalkyl, aliphatic, heteroaliphatic, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or $S(O)_n$, where n is an integer from 0 to 2, and R is hydrogen, alkyl, haloalkyl, cycloalkyl, aralkyl, aryl, heteroaryl or heteroaralkyl), or —C(O)N(R')R" (where R' and R" are independently selected from hydrogen or alkyl). Representative examples include, but are not limited to, cyclopentyl, cyclohexyl, cycloheptyl, cycloheptenyl, or cycloheptyl-2, 3, or 4-one, and the like.

The term "carboxylate" or "carboxyl" refers to the group $—COO^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$ alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

"Heterocyclic" refers to a closed-ring compound, or radical thereof as a substituent bonded to another group, particularly other organic groups, where at least one atom in the ring structure is other than carbon, and typically is oxygen, sulfur and/or nitrogen.

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$ alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino Unless otherwise defined optionally substituted N-heterocyclics includes pyridinium salts and the N-oxide form of suitable ring nitrogens.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$ alkyl, $C_{2-6}$ alkenyl, $C_{2-6}$ alkynyl, $C_{3-8}$cycloalkyl, hydroxyl, oxo, $C_{1-6}$ alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

"Substituted sulfanyl" refers to the group —SR, wherein the number of R groups satisfies the oxidation state of S and R may be, for example, halo, optionally-substituted alkyl, optionally-substituted aryl, optionally-substituted carbocyclic, or optionally-substituted heterocyclic.

"Sulfanyl" refers to —SH.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition.

As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, excipients, and/or adjuvants, and optionally other biologically active ingredients. Pharmaceutical additives include, for example, bulking agents, disintegrating agents, anti-adherents and glidants, lubricants, binding agents, flavoring agents, etc., including without limitation: bulking agents, such as microcrystalline cellulose, mannitol, xylitol, dicalcium phosphate, calcium sulfate, starches, lactose, sucrose, sorbitol, cellulose powder, and combinations thereof; disintegrating agents, such as microcrystalline cellulose, starches, crospovidone, sodium starch glycolate, croscarmellose sodium, and combinations thereof; antiadherents and glidants, such as talc, corn starch, silicon dioxide, sodium lauryl sulfate, metallic stearates, and combinations thereof; lubricants, such as magnesium stearate, calcium stearate, sodium stearate, stearic acid, sodium stearyl fumarate, hydrogenated cotton seed oil, talc, and waxes, including but not limited to, beeswax, carnauba wax, cetyl alcohol, glyceryl stearate, glyceryl palmitate, glyceryl behenate, hydrogenated vegetable oils, stearyl alcohol, and combinations thereof; and binding agents, such as polyvinyl pyrollidone, starch, methylcellulose, hydroxypropyl methylcellulose, carboxymethyl cellulose, sucrose solution, dextrose solution, acacia, tragacanth, locust bean gum, and combinations thereof. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the formulations herein disclosed. In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sorbitan monooleate. Such pharmaceutical compositions can be prepared by standard pharmaceutical formulation techniques such as those disclosed in *Remington's Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

II. Compounds

KCNQ genes encode five Kv7 potassium channel subunits (Kv7.1-Kv7.5). Kv7.2-Kv7.5 are expressed in the nervous system. The $K_v7.1$ subtype is primarily located in the cell membranes of cardiac tissue, and critical for the repolarization of the cardiac action potential. $K_v7.2$-$K_v7.5$ are active in neuronal tissue, and $K_v7.4$ and $K_v7.5$ are also expressed in skeletal and smooth muscle cells. The neuronal channels are assembled as homo- or heterotetramers, i.e. they form $K_v7.2$/$K_v7.3$, $K_v7.3$/$K_v7.4$, $K_v7.4$/$K_v7.5$, etc., channel complexes. Kv7.2/Kv7.3 heterotetramers are principle molecular components of a slow voltage-gated M-channel, referred to herein as the KCNQ2/3 channel, which widely regulates neuronal excitability. They control the subthreshold membrane potential and serve as powerful brakes on neuronal firing activity.

Embodiments of the disclosed compounds are selective potassium channel agonists. In some embodiments, the compounds increase activity of KCNQ2/3 ($K_v7.2$/$K_v7.3$) channels, thereby providing a novel therapeutic approach for treating epilepsy and tinnitus. In some embodiments, the compounds also may be useful for treating neuropathic pain, anxiety, mania, attention deficit hyperactivity disorder (ADHD), depression, and/or migraines. In certain embodiments, the compounds may also be used prophylactically to prevent induction of tinnitus. Preventing the development of chronic tinnitus with transient, well-timed therapies will reduce the deficiencies of systemic medications as well as the health care costs associated with the long-term medical care of tinnitus patients.

Disclosed herein are (2-amino-4-(arylamino)phenyl)carbamates that activate potassium channels. In some embodiments, the compounds may selectively activate KCNQ2/3 channels and therefore are selective potassium channel agonists. "Selectively active" means that potassium channels other than KCNQ2/3 are not activated, or are only minimally activated relative to the KCNQ2/3 potassium channel activation.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C=C, C=N). All chiral, diastereomeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also include all isotopes of atoms present in the compounds, which can include, but are not limited to, deuterium, tritium, $^{18}F$, $^{14}C$, etc.

Embodiments of the disclosed selective potassium channel agonists, or pharmaceutically acceptable salts thereof, have a structure according to general formula I (I)

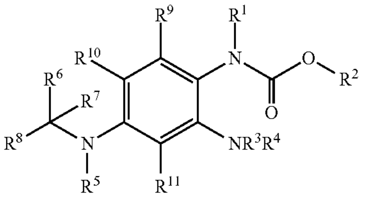

wherein:

$R^1$ is H or optionally-substituted alkyl;

$R^2$ is optionally-substituted $C_1$-$C_6$ alkyl (linear or branched) or optionally-substituted cyclopropyl;

$R^3$ and $R^4$ are each independently H or optionally-substituted alkyl;

$R^5$ is H, optionally-substituted alkyl, acyl, or alkoxycarbonyl;

$R^6$ and $R^7$ are each independently H, optionally-substituted alkyl, or $R^6$ and $R^7$ together form a carbocycle;

$R^8$ is substituted phenyl or optionally-substituted pyridinyl, provided that if $R^8$ is substituted phenyl, then $R^2$ is optionally-substituted cyclopropyl; and $R^9$, $R^{10}$ and $R^{11}$ are each independently H, halo, or optionally-substituted alkyl.

In some embodiments, $R^1$ and $R^5$ are H. In certain embodiments, $R^7$ and $R^8$ are H. In any or all of the foregoing embodiments, $R^3$ and $R^4$ may be H.

$R^2$ is optionally-substituted $C_1$-$C_6$ alkyl or optionally-substituted cyclopropyl. In some embodiments, $R^2$ is unsubstituted $C_1$-$C_6$ alkyl or cyclopropyl. In some examples, $R^2$ is ethyl, cyclopropyl, or isopropyl. In certain embodiments, $R^2$ is ethyl or cyclopropyl.

In any or all of the above embodiments, $R^9$-$R^{11}$ independently may be H or halo. In some embodiments, $R^9$-$R^{11}$ independently are H or F, wherein at least one of $R^9$-$R^{11}$ is F. In certain embodiments, $R^H$ is F and $R^9$ and $R^{10}$ independently are H or F. In some example, $R^H$ is F, one of $R^9$ and $R^{10}$ is F, and the other of $R^9$ and $R^{10}$ is H.

$R^8$ is substituted phenyl or optionally-substituted pyridinyl. In any or all of the above embodiments, when $R^8$ is substituted phenyl, then $R^2$ is optionally-substituted cyclopropyl. In some embodiments, $R^8$ is optionally-substituted pyridinyl and $R^2$ is optionally-substituted $C_1$-$C_6$ alkyl or optionally-substituted cyclopropyl. In certain embodiments, $R^8$ is optionally-substituted pyridinyl and $R^2$ is unsubstituted $C_1$-$C_6$ alkyl, such as ethyl, or cyclopropyl. In some embodiments, $R^8$ is

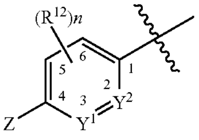

wherein $Y^1$ and $Y^2$ independently are CH, CX where X is halo, N, or CCN, provided that at least one of $Y^1$ and $Y^2$ is CH or CX; $R^{12}$ is halo, substituted sulfanyl (e.g., halosulfonyl), or haloalkyl; Z is haloalkyl, halo, or H, and n is 0, 1, or 2. In certain embodiments, $R^{12}$ is fluoro, $SF_5$ or $CF_3$. In some examples, Z is $CF_3$, F, or H. In particular examples, Z is $CF_3$.

In certain embodiments, $R^8$ is

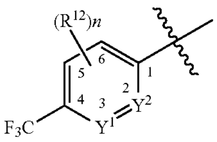

, wherein $Y^1$ and $Y^2$ independently are CH, CX where X is halo, N, or CCN, provided that at least one of $Y^1$ and $Y^2$ is CH or CX; $R^{12}$ is halo, and n is 0, 1, or 2. In certain embodiments, $Y^1$ and $Y^2$ are both CH, or one of $Y^1$ and $Y^2$ is N and the other of $Y^1$ and $Y^2$ is CH; and n is 0 or 1. In some examples, n is 1 or 2, and $R^{12}$ is fluoro.

In some embodiments, the selective potassium channel agonists, or pharmaceutically acceptable salts thereof, have a structure according to general formula II (II)

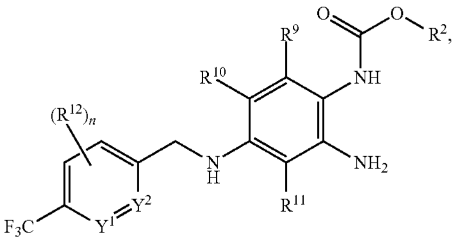

wherein $R^2$, $R^9$-$R^{12}$, $Y^1$, $Y^2$, and n are as previously defined. In certain embodiments, $R^{12}$ is halo, such as F, and n is 1 or 2. In some examples, n is 0. In some embodiments, $R^{11}$ is F, and $R^9$ and $R^{10}$ independently are H, halo, or optionally-substituted alkyl, such as haloalkyl. In certain embodiments, $R^{11}$ is F, and $R^9$ and $R^{10}$ independently are H, F, or —$CF_3$. In some examples $R^9$ is H or F. In certain examples, $R^{11}$ is F, and $R^9$ and $R^{10}$ independently are H or F.

In some embodiments, the selective potassium channel agonist has a structure according to general formula II wherein one of $Y^1$ and $Y^2$ is N and the other of $Y^1$ and $Y^2$ is CH, one of $Y^1$ and $Y^2$ is CF and the other of $Y^1$ and $Y^2$ is CH, both $Y^1$ and $Y^2$ are CH, or one of $Y^1$ and $Y^2$ is N and the other of $Y^1$ and $Y^2$ is CCN. In certain embodiments, one of $Y^1$ or $Y^2$ is N, and $R^2$ is ethyl or cyclopropyl. In any of the foregoing embodiments where one of $Y^1$ or $Y^2$ is N, and $R^2$ is ethyl or cyclopropyl, n may be 0 or 1. When n is 1, $R^{'2}$ may be F. In one embodiment, $Y^1$ is N, $Y^2$ is CH, n is 1, and $R^{12}$ is F and is positioned para to V, i.e., at the C6 position. In an independent embodiment, $Y^1$ is CH, $Y^2$ is N, n is 1, and $R^{12}$ is F and is at the C6 position. In another independent embodiment, $Y^1$ is N, $Y^2$ is CH, and n is 0. In still another independent embodiment, $Y^1$ is CH, $Y^2$ is N, and n is 0. In another independent embodiment, $Y^1$ and $Y^2$ are CH, and n is 0. In yet another independent embodiment, $Y^1$ is CH, $Y^2$ is CF, and n is 0. In any or all of the foregoing embodiments, $R^{11}$ may be F, and $R^9$ and $R^{10}$ independently may be H, F, or haloalkyl. In some embodiments, the haloalkyl is —$CF_3$.

When $Y^1$ and $Y^2$ independently are CH or CX, the selective potassium channel agonist may have a structure according to general formula III (III)

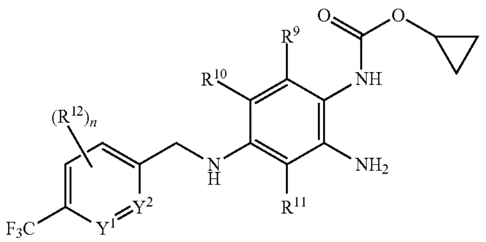

, wherein $R^2$, $R^9$-$R^{12}$, and n are as previously defined. In one embodiment, $Y^1$ is CH and $Y^2$ is CH or CX, such as CF. In an independent embodiment, $Y^1$ is CH, $Y^2$ is CH or CF, and n is 0. In any or all of the foregoing embodiments where $Y^1$ is CH, $Y^2$ is CH or CF, and n is 0, $R^{11}$ may be F, and $R^9$ and $R^{10}$ independently may be H, F, or haloalkyl. In some embodiments, the haloalkyl is —$CF_3$. In another independent embodiment, $Y^1$ is CH or CX, such as CF, and $Y^2$ is CH. In yet another independent embodiment, $Y^1$ is CH or CF, $Y^2$ is CH, and n is 0. In any or all of the foregoing embodiments where $Y^1$ is CH or CF, $Y^2$ is CH, and n is 0, $R^{11}$ may be F, and $R^9$ and $R^{10}$ independently may be H, F, or haloalkyl. In some embodiments, the haloalkyl is —$CF_3$. In certain embodiments where $Y^1$ is CH or CF, $Y^2$ is CH, and n is 0, $R^{11}$ may be F, and $R^9$ and $R^{10}$ independently may be H or F.

In some embodiments, the potassium channel agonist selectively activates the KCNQ2/3 channel. In certain embodiments, the potassium channel agonist has a high selectivity for KCNQ2/3 over KCNQ4/5, such as a selectivity of >5, >7, or even >10. In some embodiments, the agonist concentration that doubles the conductance at the voltage leading to 15% channel activation ($EC_{2x}$) is <2 μM, such as <1.5 μM, <1 μM, or even less than 0.5 μM. In some examples, the $EC_{2x}$ is from 0.1-2 μM, 0.1-1.5 μM, or 0.1-1 μM. In a few examples, the potassium channel agonist has a high selectivity for KCNQ4/5 over KCNQ2/3 providing a KCNQ2/3 over KCNQ4/5 selectivity of <1.

Representative, non-limiting examples of selective potassium channel agonists are shown in Table 1:

TABLE 1

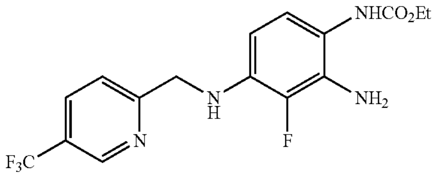

RL702.031 (2351785870)

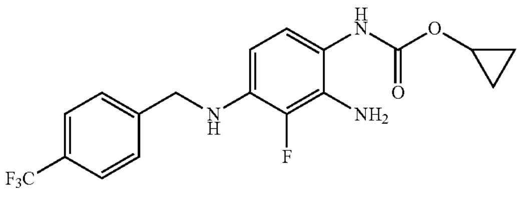

RL702.56 (2351785872)

TABLE 1-continued

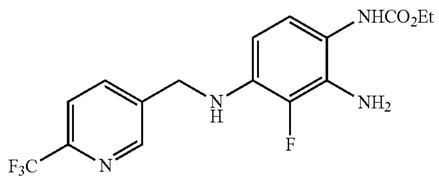

RL702.024 (2351785869)

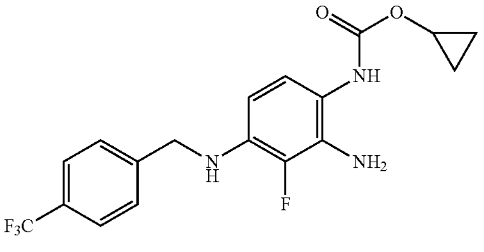

RL-32

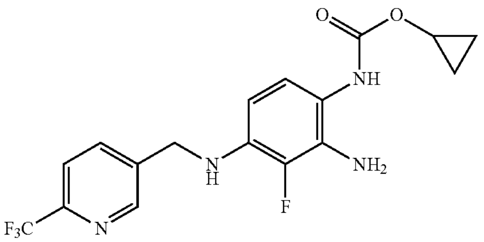

RL-67

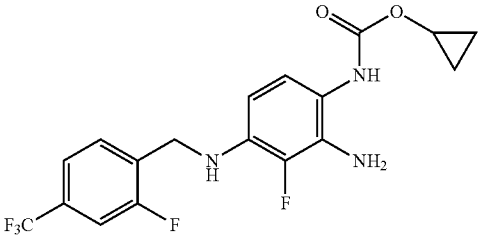

RL-35

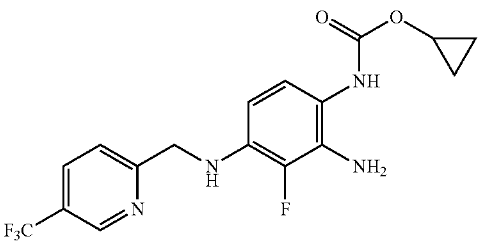

RL-68

TABLE 1-continued

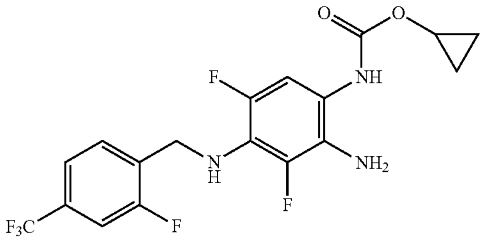

RL-36

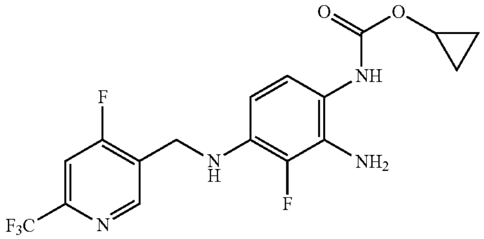 [SMILES: Nc1c(NC(=O)OC2CC2)ccc(NCc2cnc(C(F)(F)F)cc2F)c1F]

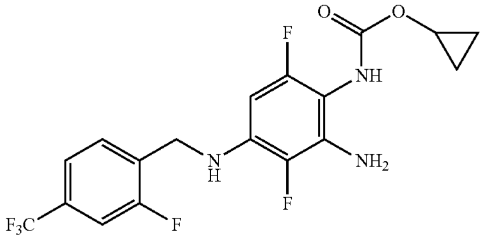

RL-46

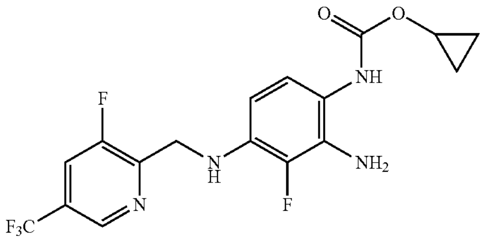

RL-96

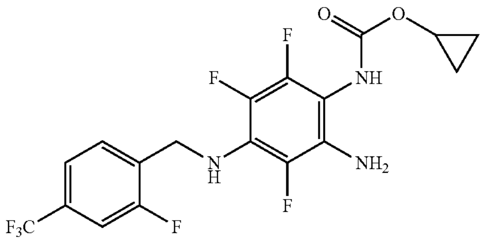

RL-50

TABLE 1-continued

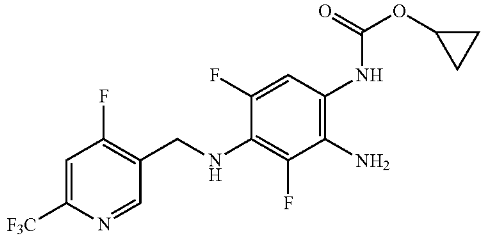 [SMILES: Nc1c(NC(=O)OC2CC2)cc(F)c(NCc2cnc(C(F)(F)F)cc2F)c1F]

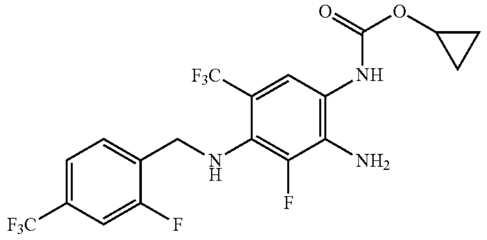 [SMILES: Nc1c(NC(=O)OC2CC2)cc(C(F)(F)F)c(NCc2ccc(C(F)(F)F)cc2F)c1F]

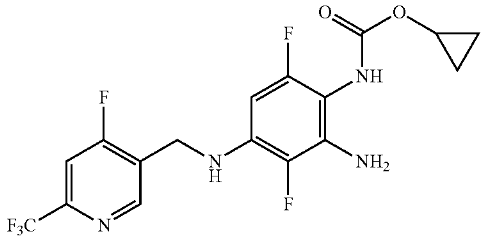 [SMILES: Nc1c(F)c(NCc2cnc(C(F)(F)F)cc2F)cc(F)c1NC(=O)OC1CC1]

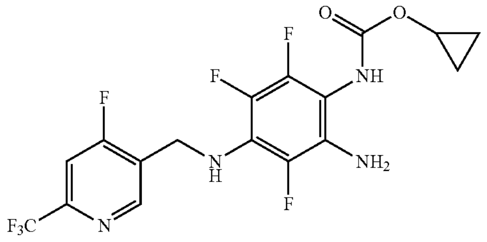 [SMILES: Nc1c(F)c(NCc2cnc(C(F)(F)F)cc2F)c(F)c(F)c1NC(=O)OC1CC1]

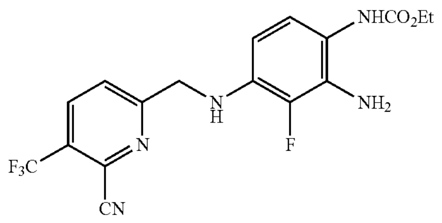

RL-23

III. Methods of Use

Disclosed herein are methods for activating a potassium channel, particularly a KCNQ2/3 potassium channel, by contacting the potassium channel with an effective amount of a compound as disclosed herein. Contacting the KCNQ2/3 potassium channel may comprise administering the effective amount of the compound to a subject.

In some embodiments, disclosed herein are methods for administering a therapeutically effective amount of a compound disclosed herein to a subject for treating or preventing conditions mediated by KCNQ2/3 potassium channel activity, particularly conditions caused or exacerbated by decreased KCNQ2/3 potassium channel activity. In one aspect, the methods treat a subject suffering from or susceptible to conditions that are ameliorated by KCNQ2/3 potassium channel opening or activation, comprising administering to the subject in need thereof a therapeutically effective amount of a compound disclosed herein, or a pharmaceutically acceptable salt thereof. In certain embodiments, the methods disclosed herein ameliorate such conditions by increasing the ion flow through KCNQ2/3 potassium channel(s).

In certain embodiments, there is provided a method of treating or preventing tinnitus in a subject in need thereof comprising administering to the subject a therapeutically effective amount of a compound disclosed herein, or a pharmaceutically acceptable salt thereof. The tinnitus may be a condition of, for example, age-related hearing loss, ear injury, circulatory system disorder, neurological damage, or ear infections.

In certain embodiments, there is provided a method of treating or preventing epilepsy in a subject in need thereof comprising administering to the subject a therapeutically effective amount of a compound disclosed herein, or a pharmaceutically acceptable salt thereof. "Epilepsy" is intended to include the following seizures: —simple partial seizures, complex partial seizures, secondary generalized seizures, generalized seizures including absence seizures, myoclonic seizures, clonic seizures, tonic seizures, tonic clonic seizures and atonic seizures. Also disclosed herein is a method for treating a subject suffering from or susceptible to epilepsy comprising co-administering to the subject in need thereof a therapeutically effective amount of a compound disclosed herein and one or more anti-epileptic drugs (AEDs). There are different types of AEDs. For example, narrow-spectrum AEDs include e.g., phenyloin, phenobarbital, carbamazepine, oxcarbazepine, gabapentin, pregabalin, lacosamide, and vigabatrin. Broad spectrum AEDs include e.g., valproic acid, lamotrigine, topiramate, zonisamide, levetiracetam, clonazepam, and rufinamide. In one aspect, the AED is any AED. In one aspect, the AED is a narrow spectrum AED. In one aspect, the AED is a broad spectrum AED.

In certain embodiments, the subject is in need of, or has been recognized as being in need of, treatment with a KCNQ2/3 activator. The subject may be selected as being amenable to treatment with a KCNQ2/3 activator.

In some embodiments, the methods disclosed herein involve administering to a subject in need of treatment a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

In some embodiments, one or more of the disclosed compounds are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., $21^{st}$ Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The active compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. When administered orally, an administered amount therapeutically effective may be from about 0.1 mg/day to about 1,000 mg/day. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerin, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropylene glycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians who are skilled in therapy of retroviral infections, diseases, and associated disorders.

IV. Examples

Example 1

Synthesis of Representative Compounds

Previously synthesized compound RL-81 is a KCNQ2/3 activator ($EC_{50}$=260 nM) that is more potent than flupirtine (FP) ($EC_{50}$=2.0 μM) and retigabine (RG) ($EC_{50}$=330 nM).

RL-81

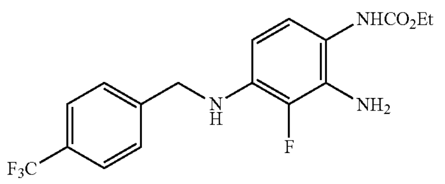

RL-81 was selected as a promising lead for development of clinical candidates for treating or preventing neurological disorders associated with neuronal hyperexcitability. Attention was focused on the position and number of fluorine groups on the three unsubstituted carbons of the triaminobenzene moiety, i.e., $R^9$-$R^{11}$ of formula I.

The syntheses of RL-81 and 19 new analogs are summarized in FIGS. 1-4. $S_NAr$ of benzylamines 3a-3c with fluorarenes 4a and 4b in the presence of catalytic iodine generated anilines 5a-5d in 63-84% yield (FIG. 1). Reduction of the nitro group and treatment with ethyl chloroformate led to RL-81, RL-73, RL-02, and RL-72 in 47%, 45%, 37%, and 24% yield, respectively. RL-81 was treated with trifluormethylating agent 6 in acetonitrile to obtain the $R^{10}$ trifluoromethyl derivative RL-073, albeit in a low yield of 17%. For the preparation of isopropyl and cyclopropyl carbamates RL-32 and RL-56, nitroaniline 5a was reduced with Pd/C under an atmosphere of hydrogen gas in ethanol, and the resulting diamine was selectively acylated with isopropyl chloroformate and cyclopropyl chloroformate in 63% and 40% yield, respectively.

The use of 2-fluoro-4-trifluoromethylbenzylamine 3d introduced an additional fluorine group at Y2 of formula I, and in an analogous series of $S_NAr$, zinc reduction, and carbamoylation transformations, ethyl carbamate RL-18 and cyclopropyl carbamates RL-35, RL-36, RL-46, and RL-50 were obtained in moderate to good yields (FIG. 2). In this series of analogs, up to two additional fluorine substituents were introduced at the $R^9$ and $R^{10}$ positions.

Figure 3:
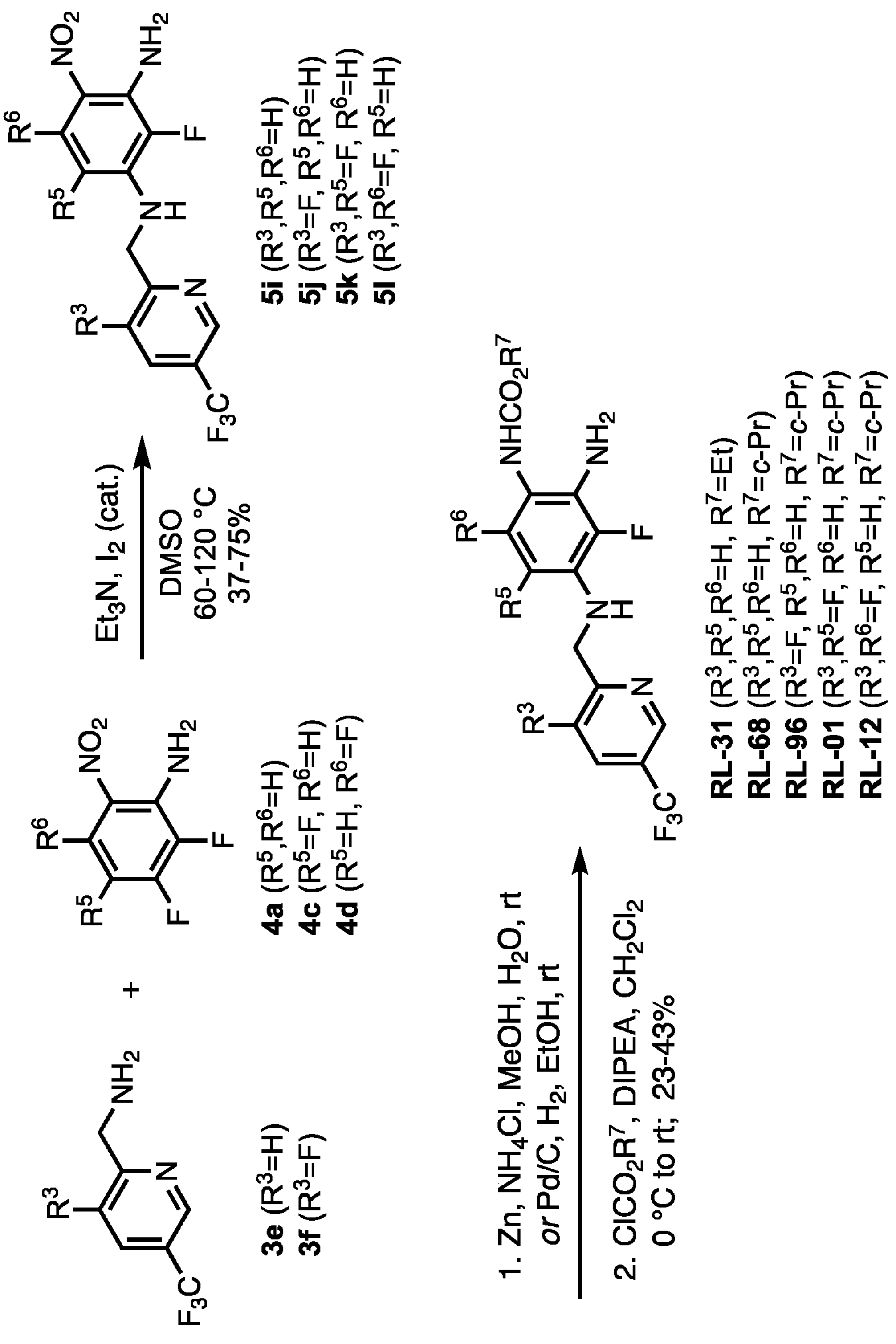

A further diversification of the RL-81 structure was accomplished by the use of (5-(trifluoromethyl)pyridin-2-yl)methanamine 3e and (3-fluoro-5-(trifluoromethyl(pyridin-2-yl)methanamine 3f (FIG. 3). Reduction of the nitro group in 5i, isolated in 75% yield from the coupling of 3e with 4a, with Pd/C and acylation with ethyl chloroformate provided RL-31 in 43% yield. A zinc reduction and cyclopropyl chloroformate were used for the preparation of RL-68 in 23% yield from 5i. The penta- and hexa-fluorinated intermediates 5j, 5k, and 5l were obtained from the coupling of 3e with 4a, 4c and 4d in 45%, 58%, and 37% yield, respectively. Zinc reduction and treatment with cyclopropyl chloroformate then yielded the corresponding carbamates RL-96, RL-01, and RL-12 in 33%, 37%, and 41% yield, respectively.

Figure 4:
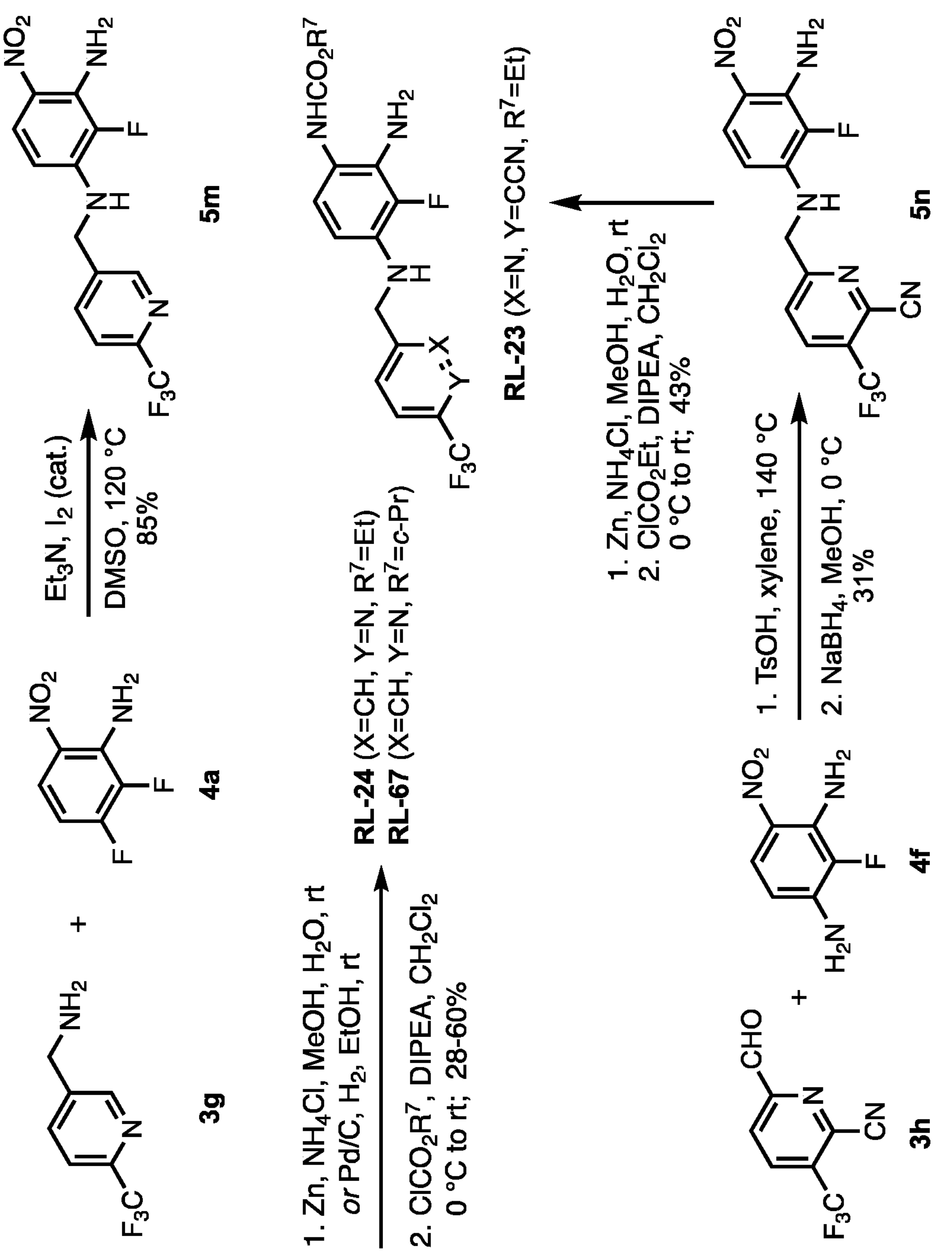

Finally, analogs with a pyridine group were synthesized by coupling of amine 3g with nitrobenzene 4a, which gave $S_NAr$ product 5m in 85% yield (FIG. 4). Reduction and acylation of 5m provided the carbamates RL-24 and RL-67 in 60% and 28% yield, respectively. The 2-pyridyl RL-23 which also contained a cyano group next to the nitrogen of the heterocycle (position Y1 of formula I) as a chemical replacement mimicking a pyridazine ring was generated in an overall yield of 13% by a reductive amination of pyridine 3h with aniline 4f, followed by reduction and acylation.

Full synthesis and characterization details are provided below.

General Experimental Protocols

All non-aqueous reactions were carried out under a nitrogen atmosphere in oven-dried glassware. Anhydrous tetrahydrofuran and diethyl ether were distilled from sodium benzophenone ketyl. Anhydrous dichloromethane, toluene and xylene were distilled from $CaH_2$. 1,4-dioxane, and MeOH, and MeCN were dried over 3 Å molecular sieves unless otherwise noted. Other solvents and reagents were used as obtained from commercial sources without further purification unless noted. Reactions were monitored via TLC using 250 μm pre-coated silica gel 60 $F_{254}$ plates, which were visualized with 254 nm and/or 365 nm UV light. Flash chromatography was performed with SiliCycle silica gel 60 (230-400 mesh). $^1H$, $^{13}C$ and $^{19}F$ NMR spectra were recorded on Bruker Avance 400, 500 or 600 MHz spectrometers, using the residual solvent as an internal standard. Melting points were obtained using a Laboratory Devices Mel-Temp II with open capillaries and are uncorrected. IR spectra were obtained on a PerkinElmer Spectrum 100 FT-IR. HRMS data were obtained on a Thermo Scientific Exactive Orbitrap LC-MS using heated electrospray ionization (HESI). X-Ray crystallography analysis was performed on Bruker X8 APEX X-ray diffractometer. All screening samples were analyzed by LC-HRMS prior to submission, and passed purity requirements (>95% by UV/ELS detection). LC-HRMS and ELS data were obtained on a Thermo Scientific Exactive Orbitrap LC-HRMS (ESI positive ion mode) coupled to an Agilent Technologies 385-ELSD and a Thermo Scientific Accela HPLC system using a 3.5 μm Waters XTerra C18 column (2.1×50 mm; 10 min gradient elution with $MeCN/H_2O/MeOH$ containing 0.1% formic acid at a flow rate of 500 μL/min from 3:92:5 at 0-0.5 min to 93:2:5 at 4.0 min, back to 3:92:5 from 6.0 to 7.5 min).

Synthesis Procedures and Compound Characterizations

2

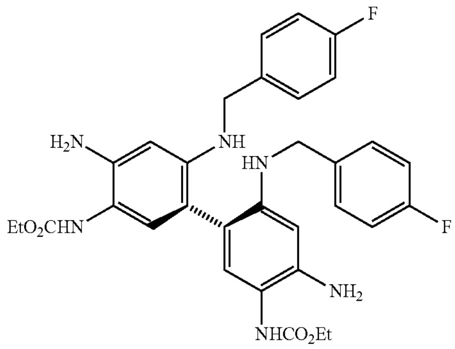

Diethyl (4,4'-diamino-6,6'-bis((4-fluorobenzyl)amino)-[1,1'-biphenyl]-3,3'-diyl)dicarbamate (2). To a solution of retigabine 1 (1.22 g, 4.02 mmol) in $CH_2Cl_2$ (300 mL) was added (diacetoxyiodo)benzene (0.648 g, 2.01 mmol) in one portion. The reaction mixture was stirred at room temperature for 2 h. The resulting purple solution was quenched with saturated $Na_2CO_3$, extracted with $CH_2Cl_2$ (3×30 mL), dried ($Na_2SO_4$), filtered, and concentrated in vacuo. The residue was purified by chromatography on $SiO_2$ (EtOAc/hexanes, 3:7 to 1:1) to afford 2 as a purple solid (0.334 g, 27%). Recrystallization from $CH_2Cl_2$/hexanes afford a yellowish solid: Mp 180.2-184.4° C.; IR (ATR) 3355, 1699, 1623, 1509, 1224, 1062, 827 $cm^{-1}$; $^1H$ NMR (500 MHz, $CDCl_3$) δ 7.19 (dd, 4H, J=8.3, 5.5 Hz), 6.94 (t, 4H, J=8.6 Hz), 6.81 (s, 2H), 6.13 (br s, 2H), 5.96 (s, 2H), 4.21 (s, 4H), 4.17 (q, 4H, J=7.0 Hz), 1.38-1.09 (m, 6H); $^{13}C$ NMR (125 MHz, $CDCl_3$) δ 161.9 (d, J=245.1 Hz), 155.6, 145.6, 142.9, 135.2 (d, J=3.0 Hz), 130.1, 128.6 (d, J=8.1 Hz), 115.5 (d, J=21.3 Hz), 114.6, 113.5, 99.3, 61.5, 47.5, 14.7; HRMS (HESI) m/z calcd for $C_{32}H_{35}N_6O_4F_2$ $[M+H]^+$ 605.2682, found 605.2682.

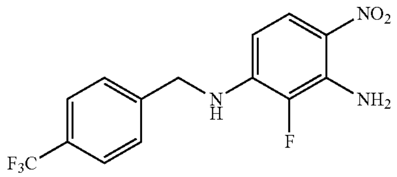

2-Fluoro-4-nitro-$N^1$-(4-(trifluoromethyl)benzyl)benzene-1,3-diamine (5a). To a stirred solution of 2,3-difluoro-6-nitroaniline 4a (1.10 g, 6.15 mmol) in dry DMSO (6 mL) was added 4-(trifluoromethyl)benzylamine 3a (1.00 g, 5.60 mmol) followed by $Et_3N$ (0.94 mL, 6.71 mmol) and 12 (28 mg, 0.11 mmol). The reaction mixture was heated to 120° C. for 36 h, cooled to room temperature, diluted with water (50 mL) and extracted with EtOAc (3×30 mL). The combined organic layers were washed with brine, dried ($Na_2SO_4$), filtered and concentrated under reduced pressure. The residue was recrystallized from acetone/hexanes to afford 5a (1.20 g). The filtrate was concentrated and purified by chromatography on $SiO_2$ (acetone/hexanes, 1:8 to 1:4 to 1:3, containing $Et_3N$ (1%)) to afford an additional batch of 5a (0.34 g; total amount 1.54 g, 84%) as a yellow solid: Mp 165.4-166.7° C.; IR (ATR) 3487, 3377, 1629, 1549, 1480, 1411, 1329, 1275, 1236, 1200, 1178, 1154, 1090, 1066, 1016, 787, 755 $cm^{-1}$; $^{1}H$ NMR (500 MHz, $CDCl_3$) δ 7.86 (dd, 1H, J=9.5, 1.0 Hz), 7.63 (d, 2H, J=8.0 Hz), 7.44 (d, 2H, J=8.0 Hz), 6.00-6.12 (m, 3H), 4.94 (brs, 1H), 4.55 (d, 2H, J=6.0 Hz); $^{13}C$ NMR (100 MHz, acetone-$d_6$) δ 144.2 (app d, J=1.0 Hz), 141.5 (d, J=9.0 Hz), 137.6 (d, J=227.0 Hz), 135.8 (d, J=13.0 Hz), 128.8 (q, J=32.0 Hz), 127.6, 125.4 (q, J=4.0 Hz), 124.5 (d, J=4.0 Hz), 124.5 (q, J=269.0 Hz), 122.9 (d, J=2.0 Hz), 100.7 (d, J=4.0 Hz), 45.5; $^{19}F$ NMR (376 MHz, $CDCl_3$) δ −62.9 (s, 3F), −160.7 (s, 1F); HRMS (HESI) m/z calcd for $C_{14}H_{12}N_3O_2F_4$ $[M+H]^+$ 330.0860, found 330.0858.

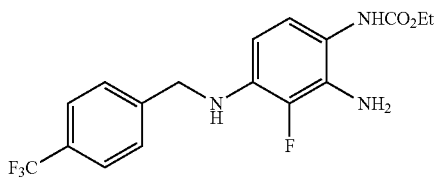

Ethyl (2-amino-3-fluoro-4-((4-(trifluoromethyl)benzyl)amino)phenyl)carbamate (RL-81). To a solution of 5a (0.066 g, 0.2 mmol) in MeOH (0.5 mL) was added zinc powder (0.066 g, 1.00 mmol) followed by the dropwise addition of a solution of saturated ammonium chloride (0.19 mL). The reaction mixture was stirred vigorously at room temperature for 5 h and filtered through celite. The celite was washed with EtOAc and the aqueous solution was extracted with EtOAc (3×2 mL). The combined organic layers were dried ($Na_2SO_4$) and concentrated to afford 3-fluoro-$N^4$-(4-(trifluoromethyl)benzyl)benzene-1,2,4-triamine as a dark red solid that was used in the next step without further purification.

An oven-dried 5-mL round bottomed flask equipped with a magnetic stir bar under argon was charged at 0° C. with 3-fluoro-$N^4$-(4-(trifluoromethyl)benzyl)benzene-1,2,4-triamine, $CH_2Cl_2$ (1 mL) and DIPEA (0.043 mL, 0.25 mmol). Ethyl chloroformate (0.02 mL, 0.20 mmol) was added dropwise via syringe at 0° C. The reaction mixture was stirred for 1 h at 0° C. and then for 3 h at room temperature, quenched with water, and extracted with $CH_2Cl_2$ (3×5 mL). The combined organic extracts were dried ($Na_2SO_4$) and concentrated under reduced pressure. The residue was purified by chromatography on $SiO_2$ (EtOAc/hexanes, 1:4 to 2:3) to afford a dark red solid that was recrystallized ($CH_2Cl_2$/hexanes) to give RL-81 (0.035 g, 47%) as colorless crystals: Mp 171.4-172.2° C.; IR (ATR) 3400, 3338, 3299, 1676, 1644, 1618, 1528, 1489, 1478, 1443, 1323, 1249, 1158, 1113, 1103, 826, 781, 775, 768, 673 $cm^{-1}$; $^{1}H$ NMR (400 MHz, $CDCl_3$) δ 7.59 (d, 2H, J=8.0 Hz), 7.46 (d, 2H, J=8.0 Hz), 6.73 (d, 1H, J=8.4 Hz), 6.13 (br s, 1H), 5.99 (t, 1H, J=8.8 Hz), 4.42 (s, 2H), 4.33 (br s, 1H), 4.19 (q, 2H, J=7.2 Hz), 3.86 (br s, 2H), 1.29 (t, 3H, J=7.2 Hz); $^{13}C$ NMR (100 MHz, acetone-$d_6$) δ 156.0, 146.4, 141.7 (d, J=227.7 Hz), 135.4, 132.5, 129.3 (q, J=32.0 Hz), 128.5, 126.1 (q, J=3.9 Hz), 125.5 (q, J=271.0 Hz), 122.3, 116.4, 101.3, 61.2, 47.4, 15.0; $^{19}F$ NMR (471 MHz, $CDCl_3$) δ −62.5 (s, 3F), −156.1 (s, 1F); HRMS (HESI) m/z calcd for $C_{17}H_{18}N_3O_2F_4$ $[M+H]^+$ 372.1330, found 372.1327.

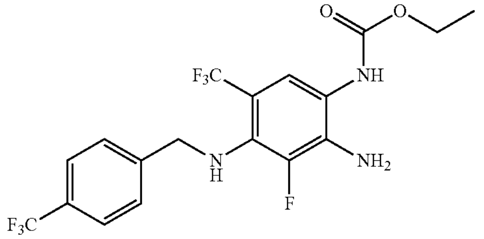

Ethyl (2-amino-3-fluoro-5-(trifluoromethyl)-4-((4-(trifluoromethyl)benzyl)amino)phenyl)carbamate (RL-073). To an oven dried microwave vial fitted with a stir bar was added 1-trifluoromethyl-1,2-benziodoxol-3-(1H)-one 6 (0.332 g, 1.05 mmol) and RL-81 (0.260 g, 0.700 mmol). The vial was evacuated and filled with $N_2$ (3×), followed by dry $CH_3CN$ (14 mL). The reaction mixture was stirred for 5 h at 85° C., concentrated in vacuo, and diluted with EtOAc and saturated $Na_2CO_3$. The aqueous layer was extracted with EtOAc (3×5 mL), dried ($Na_2SO_4$), and concentrated in vacuo. The residue was purified by chromatography on $SiO_2$ (EtOAc/hexanes, 1:4 to 3:7, containing $Et_3N$ (1%)) to afford a yellow oil that was purified by another chromatography on $SiO_2$ (20%-25% EtOAc/hexanes, 1:4 to 1:3, containing $Et_3N$ (1%)). A third chromatography on $SiO_2$ (EtOAc/hexanes, 1:4, containing $Et_3N$ (1%)) of slightly less pure fractions provided an additional batch of product, and the combined fractions were recrystallized from $CH_2Cl_2$/hexanes to afford RL-073 (0.052 g, 17%) as a white solid: Mp 107.8-108.6° C.; IR (ATR) 3371, 2986, 1703, 1642, 1492, 1324, 1225, 1158, 1108, 1066 $cm^{-1}$; $^{1}H$ NMR (500 MHz, $CDCl_3$) δ 7.59 (d, 2H, J=8.0 Hz), 7.47 (d, 2H, J=8.0 Hz), 7.10 (s, 1H), 6.09 (brs, 1H), 4.55 (s, 2H), 4.21 (q, 2H, J=7.0 Hz), 4.14 (br s, 3H), 1.30 (t, 3H, J=7.0 Hz); $^{13}C$ NMR (151 MHz, $CDCl_3$) δ 155.4, 143.8, 142.8 (d, J=232.6 Hz), 135.8, 133.1 (d, J=9.0 Hz), 129.7 (q, J=32.3 Hz), 127.8, 125.7-125.5 (m), 124.7 (qd, J=269.2, 4.2 Hz), 124.3 (q, J=272.0 Hz), 120.0, 115.4, 107.6 (d, J=25.8 Hz), 62.0, 50.8 (d, J=9.5 Hz), 14.5; $^{19}F$ NMR (471 MHz, $CDCl_3$) δ −59.3 (s, 3F), −62.5 (s, 3F), −146.1 (s, 1F); HRMS (HESI) m/z calcd for $C_{18}H_{17}N_3O_2F_7$ $[M+H]^+$ 440.1204, found 440.1195.

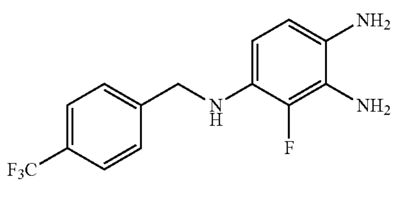

3-Fluoro-$N^4$-(4-(trifluoromethyl)benzyl)benzene-1,2,4-triamine. To a stirred solution of 5a (0.50 g, 1.52 mmol) in EtOH (5 mL) was added 10% Pd/C (0.082 g, 0.076 mmol) under $N_2$. The reaction mixture was stirred at room temperature for 4 h under a hydrogen atmosphere ($H_2$ balloon), and filtered through Celite. The filter cake was washed with $CH_2Cl_2$, and the combined liquid layers were concentrated in vacuo to afford crude 3-fluoro-$N^4$-(4-(trifluoromethyl)benzyl)benzene-1,2,4-triamine (0.39 g, 86%) as a red solid that was directly used for the next step: $^{1}H$ NMR (400 MHz, $CDCl_3$) δ 7.58 (d, 2H, J=8.0 Hz), 7.47 (d, 2H, J=8.0 Hz), 6.35 (dd, 1H, J=8.4, 2.0 Hz), 5.96 (app t, 1H, J=8.4 Hz), 4.38 (s, 2H), 4.01 (br s, 1H), 3.51 (br s, 2H), 3.06 (br s, 2H).

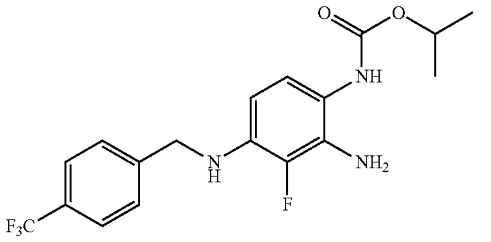 [SMILES: CC(C)OC(=O)Nc1ccc(NCc2ccc(C(F)(F)F)cc2)c(F)c1N]

Isopropyl (2-amino-3-fluoro-4-((4-(trifluoromethyl)benzyl)amino)phenyl)carbamate (RL-32). A solution of 3-fluoro-$N^4$-(4-(trifluoromethyl)benzyl)benzene-1,2,4-triamine (0.15 g, 0.50 mmol) in $CH_2Cl_2$ (10 mL) under argon was charged at 0° C. with diisopropylethylamine (0.10 mL, 0.55 mmol) and dropwise with a solution of isopropyl chloroformate (1 M in toluene, 0.045 mL, 0.45 mmol). The reaction mixture was stirred for 4 h at 0° C., and quenched with water. The aqueous layer was extracted with $CH_2Cl_2$ (3×10 mL), and the combined organic extracts were dried ($Na_2SO_4$), concentrated under reduced pressure, and purified by chromatography on $SiO_2$ (hexanes/EtOAc, 2:1 to 1:1, containing $Et_3N$ (1%)) to afford RL-32 as a light yellow solid (0.14 g, 73%). Recrystallization from $CH_2Cl_2$/hexanes afforded RL-32 (0.102 g) as a colorless solid: Mp 199.6-200.0° C.; IR (ATR) 3415, 3357, 3305, 1679, 1525, 1519, 1478, 1325, 1260, 1158, 1124, 1107, 1068 $cm^{-1}$; $^1H$ NMR (400 MHz, $CDCl_3$) δ 7.59 (d, 2H, J=8.0 Hz), 7.46 (d, 2H, J=8.4 Hz), 6.73 (d, 1H, J=8.8 Hz), 6.08 (br s, 1H), 5.99 (t, 1H, J=8.8 Hz), 4.97 (sept, 1H, J=6.0 Hz), 4.43 (d, 2H, J=5.6 Hz), 4.32 (br s, 1H), 3.88 (br s, 2H), 1.28 (d, 6H, J=6.0 Hz); $^{13}C$ NMR (100 MHz, $CDCl_3$) δ 155.0, 143.6, 141.4 (d, J=223.0 Hz), 134.9 (d, J=10.0 Hz), 130.8, 129.7 (q, J=32.0 Hz), 127.4, 125.7 (q, J=4.0 Hz), 124.3 (q, J=270.0 Hz), 121.7, 115.6, 101.9, 69.2, 47.5, 22.2; $^{19}F$ NMR (376 MHz, $CDCl_3$) δ −62.4 (s, 3F), −156.1 (s, 1F); HRMS (HESI) m/z calcd for $C_{18}H_{20}N_3O_2F_4$ $[M+H]^+$ 386.1484, found 386.1484.

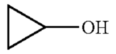

Cyclopropanol (Riggs et al., *J. Med. Chem* 2017, 60(21): 8989-9002). A suspension of cyclopropyl boronic acid (1.00 g, 11.6 mol) in water (8 mL) was treated at 0° C. with NaOH (1.02 g, 25.6 mmol), and stirred for 5 min until a homogeneous solution formed. A solution of 30% aqueous $H_2O_2$ (6.54 mL, 64.0 mmol) was added dropwise, and stirring was continued for 3 h at 0° C. The reaction mixture was extracted with $Et_2O$ (3×5 mL), and the combined organic layers were dried ($Na_2SO_4$), filtered, and concentrated in vacuo at 0° C. to afford cyclopropanol (0.36 g, 53%) as a colorless oil: $^1H$ NMR (500 MHz, $CDCl_3$) δ 3.52-3.48 (m, 1H), 0.57-0.46 (m, 4H). The compound was dissolved in dry $CH_2Cl_2$ (10 mL) and stored refrigerated over 4 Å molecular sieves for 1 d before usage.

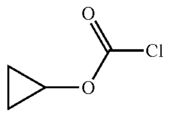

Cyclopropyl carbonochloridate (Grabowska et al. (WO2012/172473A1). A solution of cyclopropanol (0.060 g, 1.03 mmol) in $CH_2Cl_2$ (2 mL) was cooled to 0° C., treated with $K_2CO_3$ (0.43 g, 3.10 mmol) followed by phosgene (20% wt in toluene, 0.54 mL, 1.03 mmol), and stirred vigorously overnight at 0° C. to room temperature. Unreacted phosgene was removed by purging the solution with $N_2$ gas (passed through a KOH solution to dry) for 30 min. The reaction mixture was filtered through anhydrous $MgSO_4$, and concentrated at 0° C. to afford cyclopropyl chloroformate as a colorless oil (~0.3 mL) that was used directly as a toluene solution for the next step (cyclopropyl chloroformate/cyclopropanol=1:0.19, theoretical concentration=2.8 M). $^1H$ NMR (400 MHz, $CDCl_3$) δ 4.41-3.36 (m, 1H), 0.98-0.82 (m, 4H); $^{13}C$ NMR (100 MHz, $CDCl_3$) δ 151.3, 56.2, 5.49.

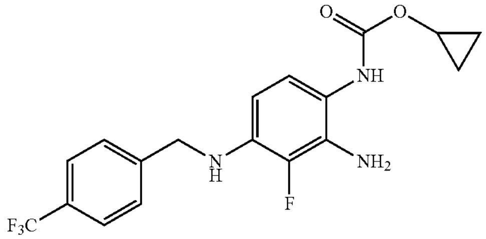

Cyclopropyl (2-amino-3-fluoro-4-((4-(trifluoromethyl)benzyl)amino)phenyl)carbamate (RL-56). A solution of 3-fluoro-$N^4$-(4-(trifluoromethyl)benzyl)benzene-1,2,4-triamine (0.07 g, 0.23 mmol) in $CH_2Cl_2$ (2.5 mL) was treated with diisopropylethylamine (0.045 mL, 0.26 mmol), cooled 0° C. and treated dropwise with cyclopropyl chloroformate (~2.8 M in toluene, 0.075 mL). The resulting mixture was stirred overnight at 0° C. to rt. After addition of water, the aqueous layer was extracted with $CH_2Cl_2$ (3×5 mL). The combined organic extracts were dried ($Na_2SO_4$), concentrated under reduced pressure and purified by chromatography on $SiO_2$ (hexanes/EtOAc, 5:1 to 2:1) to afford RL-56 (0.042 g, 47%) as a light yellow solid: Mp 175.1-175.6° C.; IR (ATR) 3314, 2937, 1696, 1523, 1327, 1258, 1163, 1117, 1103, 1066, 826, 764, 749 $cm^{-1}$; $^1H$ NMR (400 MHz, $CDCl_3$) δ 7.59 (d, 2H, J=8.4 Hz), 7.46 (d, 2H, J=8.0 Hz), 6.72 (d, 1H, J=7.6 Hz), 6.15 (br s, 1H), 5.99 (t, 1H, J=8.8 Hz), 4.42 (d, 2H, J=5.6 Hz), 4.33 (brs, 1H), 4.15-4.10 (m, 1H), 3.85 (brs, 2H), 0.72-0.70 (m, 4H); $^{13}C$ NMR (100 MHz, $CDCl_3$) δ 155.7, 143.5, 141.3 (d, J=230.0 Hz), 135.0 (d, J=9.0 Hz), 130.8, 129.7 (q, J=32.0 Hz), 127.4, 125.7 (q, J=4.0 Hz), 124.3 (q, J=271.0 Hz), 121.6, 115.2, 101.9, 49.9, 47.5, 5.2; $^{19}F$ NMR (376 MHz, $CDCl_3$) δ −62.4 (s, 3F), −156.0 (s, 1F); HRMS (HESI) calcd for $C_{18}H_{18}N_3O_2F_4$ [M+H] 384.1330, found 384.1329.

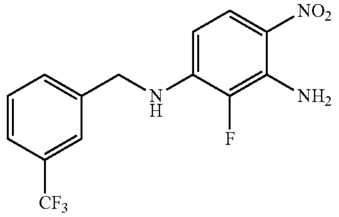 [SMILES: Nc1c([N+](=O)[O-])ccc(NCc2cccc(C(F)(F)F)c2)c1F]

2-Fluoro-4-nitro-$N^1$-(3-(trifluoromethyl)benzyl)benzene-1,3-diamine (5b). To a stirred solution of 2,3-difluoro-6- nitroaniline 4a (0.200 g, 1.11 mmol) in dry DMSO (4.6 mL) were added 3-(trifluoromethyl)benzylamine 3b (0.195 mL, 1.34 mmol) followed by $Et_3N$ (0.135 g, 1.34 mmol) and $I_2$ (cat. 2 mg). The reaction mixture was heated to 120° C. for 24 h, cooled to room temperature, diluted with water (25 mL) and extracted with EtOAc (3x15 mL). The combined organic layers were washed with brine, dried ($Na_2SO_4$), filtered and concentrated under reduced pressure. The residue was purified by chromatography on $SiO_2$ (EtOAc/hexanes, 1:10 to 1:4 to 1:3) to afford 5b as a yellow solid (0.280 g, 76%): Mp 156.0-157.2° C.; IR (ATR) 3495, 3383, 1627, 1480, 1411, 1275, 1251, 1120, 1070, 798 $cm^{-1}$; $^1H$ NMR (400 MHz, $CDCl_3$) δ 7.86 (dd, 1H, J=9.6, 1.6 Hz), 7.59-7.57 (m, 2H), 7.54-7.47 (m, 2H), 6.15-6.00 (m, 3H), 4.93 (brs, 1H), 4.54 (d, 2H, J=6.0 Hz); $^{13}C$ NMR (100 MHz, $CDCl_3$) δ 140.9 (d, J=9.5 Hz), 138.9, 138.0 (d, J=228.6 Hz), 135.2 (d, J=12.9 Hz), 131.5 (q, J=32.5 Hz), 130.5, 129.6, 125.6 (d, J=3.5 Hz), 124.9 (q, J=3.7 Hz), 124.1 (q, J=272.4 Hz), 124.0 (q, J=3.7 Hz), 123.7 (d, J=2.9 Hz), 100.7 (d, J=2.9 Hz), 46.8; $^{19}F$ NMR (471 MHz, $CDCl_3$) δ −62.7 (s, 3F), −160.6 (s, 1F); HRMS (HESI) calcd for $C_{14}H_{12}N_3O_2F_4$ $[M+H]^+$ 330.0860, found 330.0858.

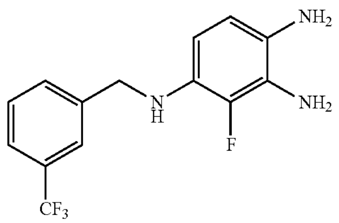

3-Fluoro-$N^4$-(3-(trifluoromethyl)benzyl)benzene-1,2,4-triamine. To a stirred solution of 5b (0.280 g, 0.85 mmol) in MeOH (2 mL) was added zinc powder (0.278 g, 4.25 mmol) followed by the dropwise addition of a solution of saturated aqueous ammonium chloride (0.80 mL). The reaction mixture was stirred vigorously at room temperature overnight, diluted with EtOAc (2 mL) and water (1 mL), and filtered through a pad of Celite. The Celite was washed with EtOAc and the solution was extracted with EtOAc (3x5 mL). The combined organic layers were dried ($Na_2SO_4$) and concentrated to afford crude 3-fluoro-$N^4$-(3-(trifluoromethyl)benzyl)benzene-1,2,4-triamine (0.190 g, 75%) as a dark red solid that was used in the next step without further purification: $^1H$ NMR (400 MHz, $CDCl_3$) δ 7.63 (s, 1H), 7.56 (d, 1H, J=7.6 Hz), 7.52 (d, 1H, J=7.6 Hz), 7.44 (t, 1H, J=7.6 Hz), 6.37 (dd, 1H, J=8.4, 2.0 Hz), 5.99 (t, 1H, J=8.8 Hz), 4.36 (s, 2H), 3.98 (brs, 1H), 3.52 (brs, 2H), 3.10 (brs, 2H); $^{19}F$ NMR (471 MHz, $CDCl_3$) δ −62.5 (s, 3F), −155.8 (s, 1F).

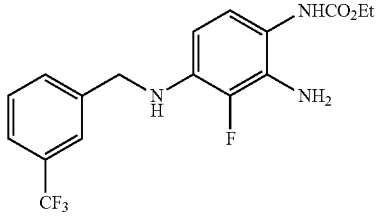

Ethyl (2-amino-3-fluoro-4-((3-(trifluoromethyl)benzyl)amino)phenyl)carbamate (RL-73). A solution of 3-fluoro-$N^4$-(3-(trifluoromethyl)benzyl)benzene-1,2,4-triamine (0.060 g, 0.20 mmol) under argon in $CH_2Cl_2$ (1 mL) was charged at 0° C. with diisopropylethylamine (0.043 mL, 0.25 mmol) and dropwise ethyl chloroformate (0.02 mL, 0.20 mmol) at 0° C. The reaction mixture was stirred for 1 h at 0° C. and for 3 h at room temperature, then quenched by addition of water. The aqueous layer was extracted with $CH_2Cl_2$ (3x5 mL). The combined organic extracts were dried ($Na_2SO_4$), concentrated under reduced pressure, and purified by chromatography on $SiO_2$ (EtOAc/hexanes, 1:4 to 2:3) to afford RL-73 (0.045 g, 60%) as a dark red solid. Recrystallization from $CH_2Cl_2$/hexanes gave colorless crystals: Mp 129.3-129.7° C.; IR (ATR) 3406, 3290, 1676, 1452, 1329, 1246, 1160, 1113, 1072, 915, 701 $cm^{-1}$; $^1H$ NMR (400 MHz, $CDCl_3$) δ 7.61 (s, 1H), 7.57-7.51 (m, 2H), 7.45 (t, 1H, J=7.6 Hz), 6.74 (dd, 1H, J=8.4, 1.2 Hz), 6.11 (br s, 1H), 6.02 (t, 1H, J=8.8 Hz), 4.41 (d, 2H, J=5.2 Hz), 4.30 (brs, 1H), 4.20 (q, 2H, J=7.2 Hz), 3.86 (brs, 2H), 1.28 (t, 3H, J=7.2 Hz); $^{13}C$ NMR (100 MHz, acetone-$d_6$) δ 156.0, 143.1, 141.8 (d, J=227.9 Hz), 135.5 (d, J=9.7 Hz), 132.4, 131.8, 130.9 (q, J=31.8 Hz), 130.1, 125.5 (q, J=271.5 Hz), 124.5 (q, J=3.9 Hz), 124.3 (q, J=3.9 Hz), 122.3, 116.5, 101.3, 61.2, 47.4, 15.0; $^{19}F$ NMR (376 MHz, $CDCl_3$) δ −62.6 (s, 3F), −155.5 (s, 1F); HRMS (HESI) calcd for $C_{17}H_{18}N_3O_2F_4$ $[M+H]^+$ 372.1330, found 372.1328.

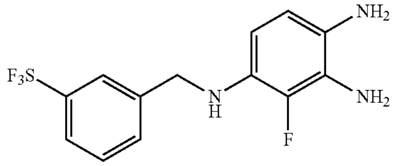

2-Fluoro-4-nitro-$N^1$-(3-(pentafluoro-$\lambda^6$-sulfanyl)benzyl)benzene-1,3-diamine (5c). A suspension of 2,3-difluoro-6-nitroaniline 4a (0.500 g, 2.78 mmol) in dry DMSO (5 mL) was treated with 3-(pentafluorosulfanyl)benzylamine 3c (0.714 g, 3.06 mmol) followed by $Et_3N$ (0.43 mL, 3.06 mmol) and $I_2$ (cat. 5 mg). The reaction mixture was heated to 120° C. for 24 h, cooled to room temperature, diluted with water (30 mL) and extracted with EtOAc (3x30 mL). The combined organic layers were washed with brine, dried ($Na_2SO_4$), filtered, and concentrated under reduced pressure. The resulting residue was treated with a small amount of $Et_2O$ (2 mL), sonicated, and filtered, and the filter cake was again washed with $Et_2O$ (3x3 mL) to afford 5c (0.51 g) as a yellow solid. The filtrate was concentrated in vacuo and the residue was purified by chromatography on $SiO_2$ (acetone/hexanes, 1:10 to 1:4 to 1:3) to afford additional 5c (0.17 g). The fractions were combined to afford 5c (0.68 g, 63%) as a yellow solid: Mp 169.5-170.0° C.; IR (ATR) 3495, 3385, 1631, 1549, 1482, 1413, 1286, 1273, 1240, 1206, 1176, 1141, 1105, 1087, 891, 859, 820, 796, 775, 751, 688 $cm^{-1}$; $^1H$ NMR (400 MHz, $CDCl_3$) δ 7.85 (dd, 1H, J=9.6, 1.6 Hz), 7.72-7.68 (m, 2H), 7.50-7.46 (m, 2H), 6.07 (brs, 2H), 6.02 (dd, 1H, J=9.6, 8.0 Hz), 5.00 (brs, 1H), 4.54 (d, 2H, J=1.5 Hz); $^{13}C$ NMR (100 MHz, acetone-$d_6$) δ 154.8 (app t, J=16.0 Hz), 142.2 (d, J=9.0 Hz), 142.2, 138.5 (d, J=228.0 Hz), 136.7 (d, J=13.0 Hz), 131.6, 130.4, 125.7-125.4 (m), 125.5 (d, J=5.0 Hz), 125.3 (app t, J=5.0 Hz), 123.8 (d, J=2.0 Hz), 101.6 (d, J=3.0 Hz), 46.3; $^{19}F$ NMR (376 MHz, $CDCl_3$) δ 84.0 (quint, 1F, J=150.4 Hz), 62.7 (d, 4F, J=150.4 Hz), −160.4 (s, 1F); HRMS (HESI) calcd for $C_{13}H_{12}N_3O_2F_2S$ $[M+H]^+$ 388.0549, found 388.0549.

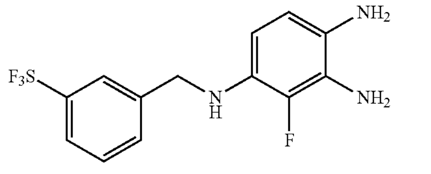

3-Fluoro-$N^4$-(3-(pentafluoro-$\lambda^6$-sulfanyl)benzyl)benzene-1,2,4-triamine. A solution of 5c (0.500 g, 1.29 mmol) in MeOH (4 mL) was treated with zinc powder (0.422 g, 6.45 mmol) followed by dropwise addition of an aqueous solution of saturated ammonium chloride (1.22 mL). The reaction mixture was stirred vigorously at room temperature overnight, and filtered through Celite. The Celite was washed (EtOAc), and the filtrate was extracted with EtOAc (3×5 mL). The combined organic layers were dried ($Na_2SO_4$), and concentrated under reduced pressure to afford 3-fluoro-$N^4$-(3-(pentafluoro-$\lambda^6$-sulfanyl)benzyl)benzene-1,2,4-triamine (0.390 g, 85%) as a red solid that was used in the next step without further purification: $^1H$ NMR (400 MHz, $CDCl_3$) δ 7.74 (s, 1H), 7.64 (d, 1H, J=8.4 Hz), 7.51 (d, 1H, J=7.6 Hz), 7.41 (t, 1H, J=8.0 Hz), 6.39 (d, 1H, J=7.6 Hz), 5.98 (t, 1H, J=8.4 Hz), 4.35 (s, 2H), 3.32 (br, 5H).

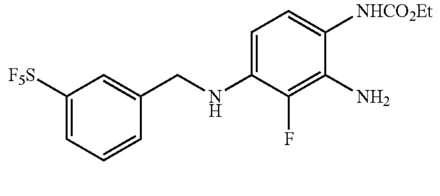

Ethyl (2-amino-3-fluoro-4-((3-(pentafluoro-$\lambda^6$-sulfanyl)benzyl)amino)phenyl)carbamate (RL-02). A solution of 3-fluoro-$N^4$-(3-(pentafluoro-$\lambda^6$-sulfanyl)benzyl)benzene-1,2,4-triamine (0.20 g, 0.56 mmol) in $CH_2Cl_2$ (3 mL) was treated under argon at 0° C. with diisopropylethylamine (0.12 mL, 0.7 mmol), followed by the dropwise addition of ethyl chloroformate (0.055 mL, 0.56 mmol) at 0° C. The reaction mixture was stirred for 1 h at 0° C., then for 3 h at room temperature, quenched with water and extracted with $CH_2Cl_2$ (3×5 mL). The combined organic extracts were dried ($Na_2SO_4$), concentrated under reduced pressure, and purified by chromatography on $SiO_2$ (EtOAc/hexanes, 1:3 to 2:3) to afford yellow solid that was recrystallized from $CH_2Cl_2$/hexanes to afford RL-02 (0.123 g, 44%) as a colorless solid: Mp 141.3-142.1° C.; IR (ATR) 3420, 3375, 2986, 1689, 1637, 1525, 1484, 1288, 1254, 1241, 829, 816, 787, 689 $cm^{-1}$; $^1H$ NMR (400 MHz, $CDCl_3$) δ 7.74 (s, 1H), 7.65 (d, 1H, J=8.0 Hz), 7.50 (d, 1H, J=7.6 Hz), 7.42 (t, 1H, J=8.0 Hz), 6.74 (d, 1H, J=7.6 Hz), 6.24 (brs, 1H), 6.00 (t, 1H, J=8.8 Hz), 4.40 (s, 2H), 4.19 (q, 2H, J=7.2 Hz), 3.98 (brs, 3H), 1.28 (t, 3H, J=7.2 Hz); $^{13}C$ NMR (100 MHz, $CDCl_3$) δ 155.5, 154.4 (quint, J=17.0 Hz), 141.3 (d, J=232.0 Hz), 140.7, 134.7 (d, J=9.0 Hz), 130.9, 130.3, 129.2, 125.0 (app t, J=5.0 Hz), 124.8 (quint, J=5.0 Hz), 121.7, 115.6, 101.9, 61.7, 47.6, 14.6; $^{19}F$ NMR (565 MHz, $CDCl_3$) δ 84.5 (quint, 1F, J=146.9 Hz), 62.8 (d, 4F, J=146.9 Hz), −155.8 (s, 1F); HRMS (HESI) calcd for $C_{16}H_{18}N_3O_2F_6S$ $[M+H]^+$ 430.1018, found 430.1015.

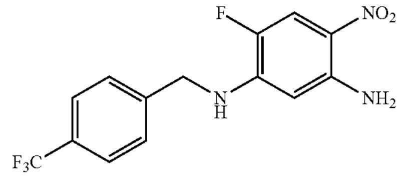 [SMILES: Nc1cc(NCc2ccc(C(F)(F)F)cc2)c(F)cc1[N+](=O)[O-]]

6-Fluoro-4-nitro-$N^1$-(4-(trifluoromethyl)benzyl)benzene-1,3-diamine (5d). A 30-mL microwave vial equipped with a magnetic stir bar was charged with 4,5-difluoro-2-nitroaniline 4b (0.530 g, 2.98 mmol) and 4-(trifluoromethyl)benzylamine 3a (0.575 g, 3.28 mmol). The vial was evacuated and filled with $N_2$ (3×). Dry DMSO (3 mL) was added followed by $Et_3N$ (0.42 mL, 2.98 mmol) and 12 (0.023 g, 0.089 mmol). The vial was sealed and the reaction mixture was heated to 120° C. for 30 h, cooled to room temperature, diluted with water (30 mL), and extracted with EtOAc (3×15 mL). The combined organic layers were washed with brine (2×5 mL), dried ($Na_2SO_4$), filtered and concentrated under reduced pressure. The residue was purified by chromatography on $SiO_2$ (acetone/hexanes, 1:4 to 3:7, containing $Et_3N$ (1%)) to afford 5d (0.81 g, 82%) as a yellow solid: Mp 150-151° C.; IR (ATR) 3446, 3323, 1641, 1549, 1397, 1325, 1283, 1251, 1105, 867 $cm^{-1}$; $^1H$ NMR (400 MHz, $CDCl_3$) δ 7.79 (d, 1H, J=12.4 Hz), 7.64 (d, 2H, J=8.0 Hz), 7.44 (d, 2H, J=8.0 Hz), 6.14 (brs, 2H), 5.69 (d, 1H, J=7.6 Hz), 5.12 (s, 1H), 4.50 (d, 1H, J=6.0 Hz); $^{13}C$ NMR (100 MHz, $CDCl_3$) δ 144.9, 143.8 (d, J=14.0 Hz), 143.5 (d, J=235.0 Hz), 141.0, 130.4 (q, J=32.0 Hz), 127.4, 126.1 (q, J=4.0 Hz), 124.1 (q, J=270.0 Hz), 121.6 (d, J=9.0 Hz), 111.1 (d, J=23.0 Hz), 96.1, 46.7; $^{19}F$ NMR (376 MHz, $CDCl_3$) δ −62.6 (s, 3F), −146.8 (s, 1F); HRMS (HESI) m/z calcd for $C_{14}H_{12}N_3O_2F_4$ $[M+H]^+$ 330.0860, found 330.0856.

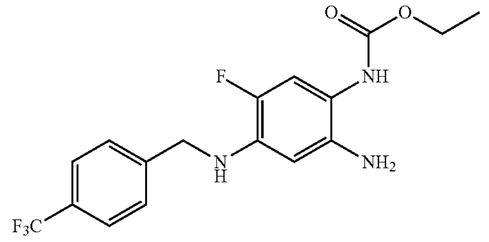 [SMILES: CCOC(=O)Nc1cc(F)c(NCc2ccc(C(F)(F)F)cc2)cc1N]

Ethyl (2-amino-5-fluoro-4-((4-(trifluoromethyl)benzyl)amino)phenyl)carbamate (RL-72). A solution of 5d (0.410 g, 1.25 mmol) in MeOH (4 mL) was charged with zinc powder (0.407 g, 6.23 mmol) followed by dropwise addition of saturated aqueous ammonium chloride solution (1.25 mL). The reaction mixture was stirred vigorously at room temperature for 1 h, filtered through Celite, and the filter cake was washed with EtOAc. The filtrate was treated with saturated aqueous $Na_2CO_3$ solution, and the aqueous layer was extracted with EtOAc (3×5 mL). The combined organic layers were washed with brine, dried ($Na_2SO_4$), and concentrated in vacuo. The resulting solid was dissolved in $CH_2Cl_2$ (20 mL), cooled to 0° C., treated with diisopropylethylamine (0.33 mL, 1.87 mmol) and ethyl chloroformate (0.11 mL, 1.12 mmol). The reaction mixture was stirred for 1 h at 0° C. and then for 3 h at room temperature before saturated aqueous $Na_2CO_3$ was added. The aqueous layer was extracted with $CH_2Cl_2$ (3×10 mL). The combined organic extracts were dried ($Na_2SO_4$), and concentrated under reduced pressure. The residue was purified by chromatography on $SiO_2$ (EtOAc/hexanes, 2:3, containing $Et_3N$ (1%)) to afford crude product that was recrystallized ($CH_2Cl_2$/hexanes) to give RL-72 (0.112 g. 24%) as a colorless solid: Mp 174.0-174.4° C.; IR (ATR) 3341, 2971, 1738, 1677, 1540, 1324, 1249, 1123, 1067, 704 $cm^{-1}$; $^1H$ NMR (400 MHz, $CDCl_3$) δ 7.59 (d, 2H, J=8.0 Hz), 7.45 (d, 2H, J=8.0 Hz), 6.93 (d, 1H, J=10.8 Hz), 6.13 (br s, 1H), 5.93 (d, 1H, J=8.4 Hz), 4.39 (s, 2H), 4.19 (q, 2H, J=7.2 Hz), 3.55 (brs, 2H), 1.28 (t, 3H, J=7.2 Hz); $^{13}C$ NMR (100 MHz, $CDCl_3$) δ 155.3, 145.0 (d, J=231.0 Hz), 143.3, 138.0, 135.3, 129.7 (q, J=32.0 Hz), 127.4, 125.8 (q, J=4.0 Hz), 124.3 (q, J=270.0 Hz), 112.8, 100.9, 61.6, 47.5, 14.7; $^{19}F$ NMR (376 MHz, $CDCl_3$) δ −62.4 (s, 3F), −146.3 (s, 1F); HRMS (HESI) m/z calcd for $C_{17}H_{18}N_3O_2F_4$ $[M+H]^+$ 372.1330, found 372.1326.

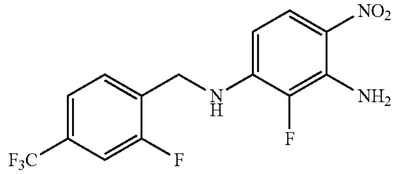 [SMILES: Nc1c([N+](=O)[O-])ccc(NCc2ccc(C(F)(F)F)cc2F)c1F]

2-Fluoro-N[1]-(2-fluoro-4-(trifluoromethyl)benzyl)-4-nitrobenzene-1,3-diamine (5e). A solution of 2-fluoro-4-(trifluoromethyl)benzylamine 3d (0.10 g, 0.50 mmol) and 2,3-difluoro-6-nitroaniline 4a (0.095 g, 0.53 mmol) in dry DMSO (1.0 mL) was treated under argon with $Et_3N$ (0.077 mL, 0.55 mmol) and $I_2$ (5 mg, 0.02 mmol). The reaction mixture was heated to 120° C. for 30 h, cooled to room temperature, quenched with water (10 mL) and extracted with $CH_2Cl_2$ (4×10 mL). The combined organic layers were washed with brine (2×10 mL), dried ($Na_2SO_4$), filtered and concentrated under reduced pressure. The residue was purified by chromatography on $SiO_2$ (acetone/hexanes, 1:8 to 1:5 to 1:4, containing $Et_3N$ (0.2%)) to afford 5e (0.142 g, 81%) as a yellow solid: Mp 153.4-153.6° C.; IR (ATR) 3487, 3379, 1629, 1547, 1478, 1420, 1281, 1238, 1176, 1161, 1115, 1090, 908, 755, 742 $cm^{-1}$; $^1H$ NMR (400 MHz, acetone-$d_6$) δ 7.78 (d, 1H, J=9.6 Hz), 7.66 (t, 1H, J=8.0 Hz), 7.54-7.51 (m, 2H), 6.71 (brs, 2H), 6.59 (br s, 1H), 6.24-6.19 (m, 1H), 4.74 (d, 2H, J=6.4 Hz); $^{13}C$ NMR (100 MHz, acetone-$d_6$) δ 161.2 (d, J=247.4 Hz), 142.1 (d, J=9.5 Hz), 138.6 (d, J=228.8 Hz), 136.7 (d, J=13.3 Hz), 131.8 (d, J=14.6 Hz), 131.5 (qd, J=25.1, 8.3 Hz), 130.9 (d, J=4.6 Hz), 125.6 (d, J=3.7 Hz), 124.5 (qd, J=271.5, 2.8 Hz), 123.9 (d, J=2.8 Hz), 122.2 (quint, J=3.8 Hz), 113.4 (dq, J=25.1, 3.9 Hz), 101.3 (d, J=3.12 Hz), 40.6 (d, J=4.6 Hz); $^{19}F$ NMR (376 MHz, acetone-$d_6$) δ −63.1 (s, 3F), −117.3 (s, 1F), −160.5 (s, 1F); HRMS (HESI) m/z calcd for $C_{14}H_{11}N_3O_2F_5$ $[M+H]^+$ 348.0766, found 348.0764.

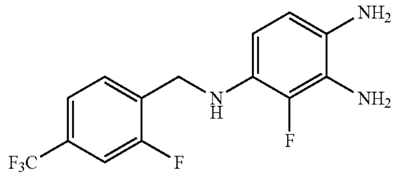

3-Fluoro-N[4]-(2-fluoro-4-(trifluoromethyl)benzyl)benzene-1,2,4-triamine. A solution of 5e (0.14 g, 0.40 mmol) in MeOH (2 mL) was treated with zinc powder (0.26 g, 4.03 mmol) followed dropwise by saturated aqueous ammonium chloride (0.76 mL). The reaction mixture was stirred vigorously at room temperature for 5 h, and filtered through Celite. The filter cake was washed ($CH_2Cl_2$), and the filtrate was dried ($Na_2SO_4$) and concentrated in vacuo to afford crude 3-fluoro-N[4]-(2-fluoro-4-(trifluoromethyl)benzyl)benzene-1,2,4-triamine (0.10 g, 78%) as a red solid that was used in the next step without further purification: HRMS (HESI) calcd for $C_{14}H_{13}N_3F_5$ $[M+H]^+$ 318.1024, found 318.1023.

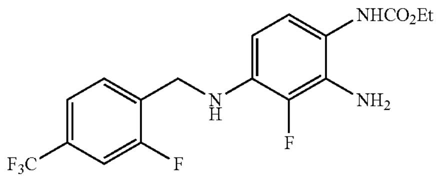

Ethyl (2-amino-3-fluoro-4-((2-fluoro-4-(trifluoromethyl)benzyl)amino)phenyl)carbamate (RL-18). A solution of 3-fluoro-N[4]-(2-fluoro-4-(trifluoromethyl)benzyl)benzene-1,2,4-triamine (0.090 g, 0.28 mmol) in $CH_2Cl_2$ (6 mL) under argon was treated at 0° C. with diisopropylethylamine (0.06 mL, 0.35 mmol) and dropwise with ethyl chloroformate (0.028 mL, 0.28 mmol). The reaction mixture was stirred for 4 h at 0° C. and quenched with water. The aqueous layer was extracted with $CH_2Cl_2$ (3×5 mL), and the combined extracts were dried ($Na_2SO_4$), concentrated in vacuo and purified by chromatography on $SiO_2$ (hexanes/EtOAc, 5:1 to 4:1 to 3:1) to afford RL-18 (0.045 g, 41%) as a red solid that was recrystallized ($CH_2Cl_2$/hexanes) to afford a colorless solid (0.030 g): Mp 170.1-170.7° C.; IR (ATR) 3407, 3331, 3297, 1681, 1646, 1521, 1489, 1428, 1329, 1254, 1217, 1163, 1120, 1081, 1064, 911, 874, 783, 744, 710 $cm^{-1}$; $^1H$ NMR (500 MHz, $CDCl_3$) δ 7.49 (t, 1H, J=8.0 Hz), 7.36 (d, 1H, J=8.0 Hz), 7.32 (d, 1H, J=10.0 Hz), 6.74 (d, 1H, J=8.5 Hz), 6.13 (brs, 1H), 6.00 (app t, 1H, J=8.5 Hz), 4.48 (d, 2H, J=6.5 Hz), 4.32 (brs, 1H), 4.19 (q, 2H, J=7.0 Hz), 3.87 (brs, 2H), 1.29 (t, 3H, J=7.0 Hz); $^{13}C$ NMR (125 MHz, $CDCl_3$) δ 160.4 (d, J=248.2 Hz), 155.5, 141.4 (d, J=232.4 Hz), 134.6 (d, J=9.9 Hz), 131.5 (qd, J=33.4, 8.0 Hz), 131.0, 130.7 (d, J=14.5 Hz), 129.7 (d, J=4.6 Hz), 123.4 (qd, J=272.3, 2.9 Hz), 121.9, 121.3 (quint, J=3.8 Hz), 115.7, 112.9 (dq, J=24.8, 3.9 Hz), 101.8, 61.7, 41.4 (d, J=4.3 Hz), 14.7; $^{19}F$ NMR (471 MHz, $CDCl_3$) δ −62.6 (s, 3F), −116.7 (s, 1F), −156.0 (s, 1F); HRMS (HESI) calcd for $C_{17}H_{17}N_3O_2F_5$ $[M+H]^+$ 390.1235, found 390.1237.

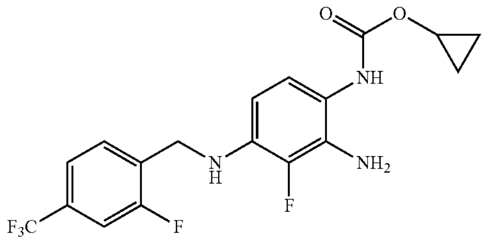 [SMILES: Nc1c(NC(=O)OC2CC2)ccc(NCc2ccc(C(F)(F)F)cc2F)c1F]

Cyclopropyl (2-amino-3-fluoro-4-((2-fluoro-4-(trifluoromethyl)benzyl)amino)phenyl)carbamate (RL-35). A suspension of 5e (0.347 g, 1.00 mmol) and zinc powder (0.327 g, 5.00 mmol) in MeOH (10 mL) was treated dropwise with aqueous 5 M ammonium chloride solution (1.00 mL) and stirred vigorously at room temperature for 1 h. The reaction mixture was filtered through Celite, and the filtrate was concentrated, diluted with EtOAc and saturated aqueous $NaHCO_3$, and the aqueous layer was extracted with EtOAc (3×10 mL). The combined organic extracts were dried ($Na_2SO_4$), filtered, and concentrated in vacuo. A solution of the dark red residue in dry $CH_2Cl_2$ (20 mL) was treated with diisopropylethylamine (0.21 mL, 1.20 mmol) and cyclopropyl chloroformate (0.50 mL, 1.00 mmol). The resulting mixture was stirred vigorously at room temperature for 4 h, quenched with saturated aqueous $NaHCO_3$ solution, and extracted with $CH_2Cl_2$ (3×10 mL). The combined organic extracts were dried ($Na_2SO_4$), concentrated in vacuo, and purified by chromatography on $SiO_2$ (EtOAc/hexanes, 3:7 to 1:1, containing $Et_3N$ (1%)) to afford a light yellow solid that was recrystallized ($CH_2Cl_2$/hexanes) to afford 5e (0.221 g. 55%) as a colorless solid: Mp 177-178° C.; IR (ATR) 3306, 1689, 1338, 1123 $cm^{-1}$; $^1H$ NMR (400 MHz, $CDCl_3$) δ 7.48 (t, 1H, J=7.6 Hz), 7.38-7.31 (m, 2H), 6.73 (d, 1H, J=7.6 Hz), 6.14 (br s, 1H), 6.00 (t, 1H, J=8.8 Hz), 4.47 (d, 2H, J=5.6 Hz), 4.33 (brs, 1H), 4.16-4.10 (m, 1H), 3.86 (brs, 2H), 0.80-0.60 (m, 4H); $^{13}C$ NMR (151 MHz, $CDCl_3$) δ 160.4 (d, J=248.5 Hz), 155.7, 141.4 (d, J=230.8 Hz), 134.6, 131.4 (qd, J=33.5, 8.0 Hz), 130.8, 130.6 (d, J=14.3 Hz), 129.7 (d, J=4.9 Hz), 123.4 (qd, J=272.1, 2.0 Hz), 121.6, 121.5-121.2 (m), 115.5, 112.9 (dm, J=24.8 Hz), 101.8, 49.9, 41.3 (d, J=4.2 Hz), 5.3; $^{19}F$ NMR (376 MHz, $CDCl_3$) δ −62.6 (s, 3F), −116.7 (s, 1F), −155.9 (s, 1F); HRMS (HESI) m/z calcd for $C_{18}H_{17}N_3O_2F_5$ $[M+H]^+$ 402.1235, found 402.1232.

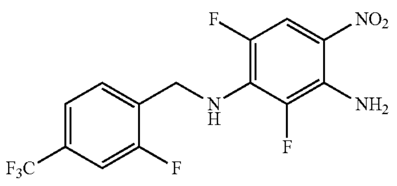 [SMILES: Nc1c([N+](=O)[O-])cc(F)c(NCc2ccc(C(F)(F)F)cc2F)c1F]

2,6-Difluoro-$N^1$-(2-fluoro-4-(trifluoromethyl)benzyl)-4-nitrobenzene-1,3-diamine (5f). A vial containing 2-fluoro-4-(trifluoromethyl)benzylamine 3d (0.20 g, 1.00 mmol) and 2,3,4-trifluoro-6-nitroaniline 4c (0.19 g, 1.00 mmol) was evacuated and backfilled with $N_2$ (3×). Dry DMSO (2.0 mL) was added, followed by $Et_3N$ (0.15 mL, 1.06 mmol) and 12 (10 mg, 0.04 mmol). The vial was sealed and the reaction mixture was heated to 120° C. for 30 h, cooled to room temperature, diluted with water (20 mL) and extracted with $CH_2Cl_2$ (3×10 mL). The combined organic layers were washed with brine (2×10 mL), dried ($Na_2SO_4$), filtered and concentrated in vacuo. The residue was purified by chromatography on $SiO_2$ (EtOAc/hexanes, 1:4, containing $Et_3N$ (0.2%)) to afford a yellow solid that was recrystallized from $CH_2Cl_2$/hexanes to afford 5f (0.26 g, 71%) as a bright yellow solid: Mp 108-110° C.; IR (ATR) 3500, 3379, 3088, 1644, 1528, 1509, 1431, 1328, 1256, 1126, 909 $cm^{-1}$; $^1H$ NMR (400 MHz, acetone-$d_6$) δ 8.17 (t, 1H, J=8.0 Hz), 8.07-7.95 (m, 3H), 7.21 (brs, 2H), 6.93 (brs, 1H), 5.32 (d, 2H, J=6.8 Hz); $^{13}C$ NMR (100 MHz, acetone-$d_6$) δ 160.8 (d, J=247.5 Hz), 143.4 (dd, J=233.0, 9.0 Hz), 139.0 (dd, J=230.0, 7.0 Hz), 136.0 (d, J=14.0 Hz), 133.0 (dd, J=16.00, 10.0 Hz), 132.8 (d, J=13.0 Hz), 131.4 (qd, J=33.0, 8.0 Hz), 130.6 (d, J=5.0 Hz), 124.5 (qd, J=270.0, 3.0 Hz), 122.2 (app quint, J=4 Hz), 121.6 (dd, J=10.0, 5.0 Hz), 113.4 (dq, J=25.0, 4.0 Hz), 107.5 (dd, J=25.0, 2.0 Hz), 42.6 (d, J=4.0 Hz); $^{19}F$ NMR (376 MHz, acetone-$d_6$) δ −63.1 (s, 3F), −118.0 (s, 1F), −144.7 (d, 1F, J=3.8 Hz), −155.5 (d, 1F, J=7.5 Hz); HRMS (HESI) m/z calcd for $C_{14}H_{10}N_3O_2F_6$ $[M+H]^+$ 366.0672, found 366.0669.

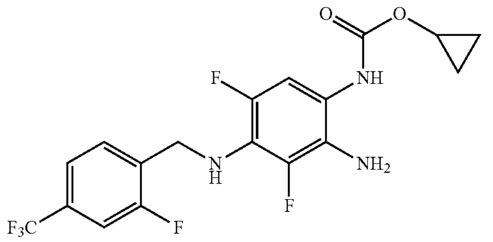

Cyclopropyl (2-amino-3,5-difluoro-4-((2-fluoro-4-(trifluoromethyl)benzyl)amino)phenyl)carbamate (RL-36). A solution of 5f (0.365 g, 1.00 mmol) in MeOH (10 mL) was treated with zinc powder (0.327 g, 5.00 mmol) followed by a 5 M aqueous ammonium chloride solution (1.00 mL). The reaction mixture was stirred vigorously at room temperature for 2 h, and filtered through Celite. The filtrate was concentrated in vacuo, and the residue was diluted with EtOAc and saturated aqueous $NaHCO_3$. The aqueous layer was extracted with EtOAc (3×10 mL), dried ($Na_2SO_4$), filtered, and concentrated in vacuo to yield a dark red residue that was dissolved in dry $CH_2Cl_2$ (20 mL). After addition of diisopropylethylamine (0.21 mL, 1.20 mmol) and cyclopropyl chloroformate (0.50 mL, 1.00 mmol), the reaction mixture was stirred vigorously at room temperature for 4 h, and quenched with saturated aqueous $NaHCO_3$. The aqueous layer was extracted with $CH_2Cl_2$ (3×10 mL), and the combined organic layers were dried ($Na_2SO_4$), concentrated in vacuo, and purified by chromatography on $SiO_2$ (EtOAc/hexanes, 3:7 to 1:1, containing $Et_3N$ (1%)) to afford a pink solid that was recrystallized ($CH_2Cl_2$/hexanes) twice to afford RL-36 (0.204 g, 49%) as a light beige solid: Mp 119-120° C.; IR (ATR) 3309, 1702, 1519, 1429, 1329, 1239, 1164, 1124 $cm^{-1}$; $^1H$ NMR (500 MHz, $CDCl_3$) δ 7.46 (t, 1H, J=7.5 Hz), 7.35 (d, 1H, J=8.0 Hz), 7.29 (d, 1H, J=10.0 Hz), 6.90 (s, 1H), 6.40 (brs, 1H), 4.54 (d, 2H, J=7.0 Hz), 4.13-4.10 (m, 1H), 3.97 (brs, 1H), 3.50 (brs, 2H), 0.71 (d, 4H, J=5.0 Hz); $^{13}C$ NMR (125 MHz, $CDCl_3$) δ 160.6 (d, J=248.5 Hz), 155.1, 146.5 (d, J=232.6 Hz), 143.9 (d, J=229.9 Hz), 131.5 (qd, J=33.3, 8.0 Hz), 131.2 (d, J=14.8 Hz), 130.3 (d, J=4.8 Hz), 125.5, 123.4 (qd, J=272.3, 2.7 Hz), 122.7, 121.2 (quint, J=3.8 Hz), 117.0, 112.9 (dq, J=24.9, 3.8 Hz), 107.2, 50.0, 44.3 (q, J=3.8 Hz), 5.1; $^{19}F$ NMR (471 MHz, $CDCl_3$) δ −62.7 (s, 3F), −117.1 (s, 1F), −139.2 (s, 1F), −147.1 (s, 1F); HRMS (HESI) m/z calcd for $C_{18}H_{16}N_3O_2F_6$ $[M+H]^+$ 420.1141, found 420.1140.

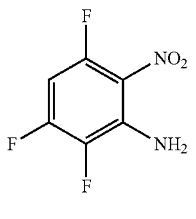 [SMILES: Nc1c(F)c(F)cc(F)c1[N+](=O)[O-]]

2,3,5-Trifluoro-6-nitroaniline (4d) (Burdon et al., *J. Fluorine Chem.* 1981, 18:507-514). A sealable vial was flushed with $N_2$ and filled with 2,3,4,6-tetrafluoronitrobenzene (1.05 g, 5.22 mmol) and $Et_2O$ (20 mL). Aqueous 28% ammonium hydroxide solution (1.60 mL, 11.49 mmol) was added dropwise over 1 h. The reaction mixture was stirred for 1 h at room temperature, quenched with water, and the aqueous layer was extracted with $Et_2O$ (2×5 mL). The combined organic layers were dried ($Na_2SO_4$), filtered, concentrated in vacuo, and the residue was purified by chromatography on $SiO_2$ (EtOAc/hexanes, 1:19 to 1:9) to afford 4d (0.884 g, 88%) as a bright yellow solid: Mp 63-65° C.; IR(ATR) 3499, 3389, 3099, 1647, 1594, 1539, 1473, 1354, 1285, 1239, 1108, 1092, 885 $cm^{-1}$; $^1H$ NMR (500 MHz, $CDCl_3$) δ 6.37 (ddd, 1H, J=11.4, 10.0, 6.5 Hz), 6.04 (brs, 2H); $^{13}C$ NMR (125 MHz, $CDCl_3$) δ 153.9 (ddd, J=261.3, 14.1, 3.6 Hz), 152.2 (ddd, J=256.6, 14.9, 11.4 Hz), 137.0-136.7 (m), 135.0 (dd, J=14.8, 4.8 Hz), 121.9, 93.5 (dd, J=27.4, 23.5 Hz); $^{19}F$ NMR (471 MHz, $CDCl_3$) δ −117.5 (dd, 1F, J=12.0, 8.9 Hz), −125.7 (dd, 1F, J=20.8, 8.9 Hz), −161.5 (dd, 1F, J=20.8, 12.2 Hz); HRMS (HESI) m/z calcd for $C_6H_4N_2O_2F_3$ $[M+H]^+$ 193.0225, found 193.0208.

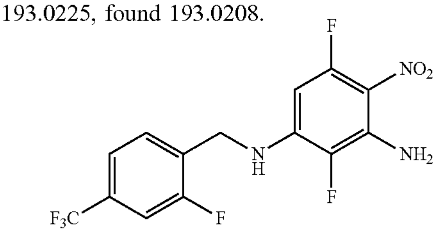

2,5-Difluoro-$N^1$-(2-fluoro-4-(trifluoromethyl)benzyl)-4-nitrobenzene-1,3-diamine (5g). An oven-dried sealable vial was charged with 2-fluoro-4-(trifluoromethyl)benzylamine 3d (0.36 g, 1.87 mmol) and 4d (0.36 g, 1.087 mmol). The vial was evacuated and backfilled with $N_2$ (3×). Dry DMSO (2.0 mL) was added, followed by $Et_3N$ (0.32 mL, 2.25 mmol) and $I_2$ (24 mg, 0.09 mmol). The vial was sealed and the reaction mixture was heated to 120° C. for 36 h, cooled to room temperature, diluted with water (20 mL), and extracted with $CH_2Cl_2$ (3×10 mL). The combined organic layers were washed with brine (2×10 mL), dried ($Na_2SO_4$), concentrated in vacuo, and purified by chromatography on $SiO_2$ (EtOAc/hexanes, 1:4, containing $Et_3N$ (0.2%)) to afford a yellow solid that was recrystallized ($CH_2Cl_2$/hexanes) to afford 5g (0.38 g, 56%) as a yellow solid: Mp 149-150° C.; IR (ATR) 3488, 3401, 1637, 1551, 1425, 1270, 1171, 1116, 881, 789 $cm^{-1}$; $^1H$ NMR (600 MHz, $CDCl_3$) δ 7.46-7.41 (m, 2H), 7.36 (d, 1H, J=10.2 Hz), 5.92 (br s, 2H), 5.85 (dd, 1H, J=13.8, 7.2 Hz), 5.02 (brs, 1H), 4.55 (d, 2H, J=6.6 Hz); $^{13}C$ NMR (151 MHz, $CDCl_3$) δ 160.4 (d, J=247.5 Hz), 156.1 (dd, J=255.0, 1.5 Hz), 139.8 (dd, J=13.9, 10.9 Hz), 135.2 (d, J=13.6 Hz), 134.2 (dd, J=225.0, 2.1 Hz), 132.4 (qd, J=33.0, 8.0 Hz), 129.6 (d, J=4.5 Hz), 128.6 (d, J=15.0 Hz), 123.2 (q, J=271.6 Hz), 121.7 (quint, J=3.6 Hz), 117.2 (d, J=10.0 Hz), 113.4 (dq, J=24.0, 3.8 Hz), 88.7 (d, J=27.0 Hz), 40.8 (d, J=4.5 Hz); $^{19}F$ NMR (565 MHz, $CDCl_3$) δ −62.8 (s, 3F), −115.8 (s, 1F), −116.8 (d, 1F, J=11.3 Hz), −164.0 (d, 1F, J=11.3 Hz); HRMS (HESI) calcd for $C_{14}H_{10}N_3O_2F_6$ $[M+H]^+$ 366.0672, found 366.0669.

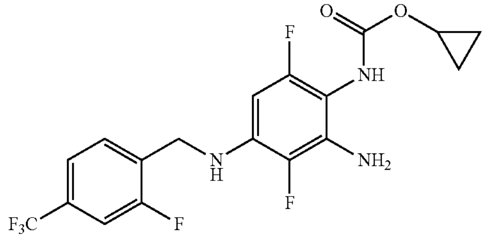 [SMILES: Nc1c(F)c(NCc2ccc(C(F)(F)F)cc2F)cc(F)c1NC(=O)OC1CC1]

Cyclopropyl (2-amino-3,6-difluoro-4-((2-fluoro-4-(trifluoromethyl)benzyl)amino)phenyl)carbamate (RL-46). A solution of 5g (0.366 g, 1.00 mmol) in MeOH (10 mL) was treated with zinc powder (0.327 g, 5.00 mmol) followed by 5 M aqueous ammonium chloride solution (1.00 mL, 5.00 mmol) and vigorously stirred at room temperature for 2 h. The reaction mixture was filtered through Celite, and the filtrate was concentrated in vacuo, and dissolved in EtOAc and saturated aqueous $NaHCO_3$. The aqueous layer was extracted with EtOAc (3×10 mL), and the combined organic layers were dried ($Na_2SO_4$), filtered, and concentrated in vacuo. A solution of the residue in dry $CH_2Cl_2$ (20 mL), was treated sequentially with diisopropylethylamine (0.21 mL, 1.20 mmol) and cyclopropyl chloroformate (0.41 mL, 0.90 mmol). The mixture was stirred vigorously at room temperature for 4 h, quenched with saturated aqueous $NaHCO_3$ solution, and extracted with $CH_2Cl_2$ (3×10 mL). The combined organic extracts were dried ($Na_2SO_4$), concentrated under reduced pressure, and purified by chromatography on $SiO_2$ (EtOAc/hexanes, 3:7 to 1:1, containing $Et_3N$ (1%)) to afford a light yellow solid that was recrystallized ($CH_2Cl_2$/hexanes) to give RL-46 (0.17 g, 41%) as a colorless solid: Mp 192-194° C.; IR (ATR) 3302, 1694, 1659, 1541, 1430, 1337, 1271, 1122 $cm^{-1}$; $^1H$ NMR (400 MHz, DMSO-$d_6$, 353 K) δ 7.91 (brs, 1H), 7.65-7.51 (m, 3H), 5.92 (br, 1H), 5.76 (dd, 1H, J=12.1, 1.6 Hz), 4.71 (br s, 2H), 4.43 (d, 2H, J=6.3 Hz), 4.00 (sept, 1H, J=3.2 Hz), 0.66-0.57 (m, 4H); $^{13}C$ NMR (151 MHz, acetone-$d_6$) 161.3 (d, J=246.8 Hz), 157.9, 157.1 (d, J=236.7 Hz), 137.2 (d, J=231.6 Hz), 136.7-136.2 (m), 135.5 (dd, J=12.1, 5.4 Hz), 132.6 (d, J=14.5 Hz), 131.2 (qd, J=33.0, 8.1 Hz), 131.0 (d, J=4.6 Hz), 124.5 (qd, J=271.6, 2.2 Hz), 122.3-122.0 (m), 113.3 (dq, J=25.2, 3.9 Hz), 102.7 (dd, J=18.0, 4.4 Hz), 87.8 (d, J=27.3 Hz), 49.8, 41.0 (d, J=4.3 Hz), 5.3; $^{19}F$ NMR (565 MHz, acetone-$d_6$) δ −63.0 (s, 3F), −117.8 (s, 1F), −127.7 (d, 1F, J=11.3 Hz), −163.4 (d, 1F, J=11.3 Hz); HRMS (HESI) m/z calcd for $C_{18}H_{16}N_3O_2F_6$ $[M+H]^+$ 420.1141, found 420.1139.

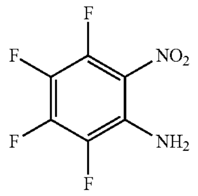 [SMILES: Nc1c(F)c(F)c(F)c(F)c1[N+](=O)[O-]]

2,3,4,5-Tetrafluoro-6-nitroaniline (4e) (Burdon et al., *J. Fluorine Chem.* 1981, 18:507-514). To a 3-neck round bottom flask flushed with $N_2$ were added pentafluoronitrobenzene (0.45 g, 2.01 mmol), $Et_2O$ (10 mL), and 28% aqueous ammonium hydroxide (0.56 mL, 4.01 mmol) dropwise over the course of 4 h. After addition of water, the aqueous layer was extracted with $Et_2O$ (2×5 mL). The combined organic layers were dried ($Na_2SO_4$), filtered, and concentrated under reduced pressure. The residue was purified by chromatography on $SiO_2$ (EtOAc/hexanes, 1:9 to 1:4) to afford 2,3,5,6-tetrafluoro-4-nitroaniline (0.097g, 23%) as a light yellow solid and 2,3,4,5-tetrafluoro-6-nitroaniline (0.24 g, 57%) as a yellow solid: Mp 41-43° C.; IR(ATR) 3494, 3373, 2923, 1668, 1606, 1538, 1519, 1351, 1255, 1121, 998 $cm^{-1}$; $^1H$ NMR (500 MHz, $CDCl_3$) δ 5.78 (brs); $^{13}C$ NMR (151 MHz, $CDCl_3$) δ 143.9 (dtd, J=262.6, 12.7, 4.7 Hz), 144.3 (ddt, J=260.2, 13.9, 4.5 Hz), 136.3 (ddd, J=243.1, 12.2, 3.7 Hz), 133.3 (dt, J=246.0, 15.1 Hz), 132.3 (d, J=12.9 Hz), 121.2; $^{19}F$ NMR (471 MHz, $CDCl_3$) δ

−144.7 (dt, 1F, J=22.7, 9.3 Hz), −147.1 (td, 1F, J=21.3, 8.9 Hz)−160.4 to −160.1 (m, 1F), −172.1 (td, 1F, J=22.4, 5.2 Hz); HRMS (HESI) m/z calcd for $C_6HN_2O_2F_4$ $[M-H]^-$ 208.9969, found 208.9976.

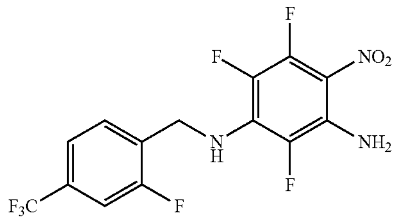 [SMILES: Nc1c(F)c(NCc2ccc(C(F)(F)F)cc2F)c(F)c(F)c1[N+](=O)[O-]]

2,5,6-Trifluoro-N[1]-(2-fluoro-4-(trifluoromethyl)benzyl)-4-nitrobenzene-1,3-diamine (5h). To an oven dried sealable vial were added 3d (0.39 g, 2.00 mmol) and 4e (0.40 g, 1.90 mmol). The vial was evacuated, backfilled with $N_2$ (3×), and dry DMSO (2.0 mL) was added followed by $Et_3N$ (0.32 mL, 2.28 mmol) and $I_2$ (24 mg, 0.09 mmol). The vial was sealed and the reaction mixture was heated to 120° C. for 42 h, cooled to room temperature, diluted with water (20 mL) and extracted with $CH_2Cl_2$ (3×10 mL). The combined organic layers were washed with brine (2×10 mL), dried ($Na_2SO_4$), filtered and concentrated under reduced pressure. The residue was purified by chromatography on $SiO_2$ (EtOAc/hexanes, 1:4 to 1:3, containing $Et_3N$ (0.2%)) to afford a yellow solid that was recrystallized ($CH_2Cl_2$/hexanes) to afford 5h (0.37 g, 51%) as a yellow solid: Mp 119-121° C.; $^1H$ NMR (400 MHz, $CDCl_3$) δ 7.50-7.40 (m, 2H), 7.36 (d, 1H, J=10.0 Hz), 5.86 (br s, 2H), 4.78 (s, 2H); $^{13}C$ NMR (151 MHz, $CDCl_3$) δ 160.5 (d, J=249.0 Hz). 144.2 (ddd, J=258.6, 14.2, 3.0 Hz), 134.1 (dm, J=228.2 Hz), 133.1 (d, J=14.7 Hz), 132.8 (ddd, J=235.2, 16.7, 7.9 Hz), 132.3 (qd, J=33.6, 8.1 Hz), 131.4 (td, J=11.5, 3.8 Hz), 129.9 (d, J=4.1 Hz), 129.7 (d, J=14.2 Hz), 123.2 (qd, J=272.7, 2.1 Hz), 121.9-1215 (m), 115.9, 113.29 (dq, J=24.6, 3.5 Hz), 43.1 (dd, J=12.7, 4.5 Hz); $^{19}F$ NMR (565 MHz, $CDCl_3$) δ −62.8 (s, 3F), −116.3 (s, 1F), −147.1 (dd, 1F, J=22.6, 5.7 Hz), −160.8 (d, 1F, J=11.3 Hz), −169.7 (d, 1F, J=17.0 Hz); HRMS (HESI) m/z calcd for $C_{14}H_9N_3O_2F_7$ $[M+H]^+$ 384.0578, found 384.0575.

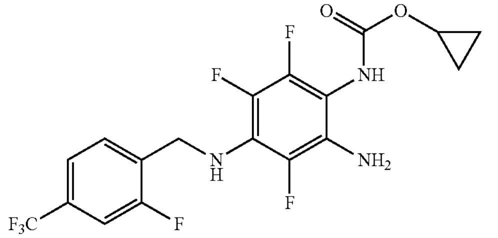 [SMILES: Nc1c(F)c(NCc2ccc(C(F)(F)F)cc2F)c(F)c(F)c1NC(=O)OC1CC1]

Cyclopropyl (2-amino-3,5,6-trifluoro-4-((2-fluoro-4-(trifluoromethyl)benzyl)amino)phenyl)carbamate (RL-50). A suspension of 5h (0.383 g, 1.00 mmol) and zinc powder (0.327 g, 5.00 mmol) in MeOH (10 mL) was treated dropwise with 5 M aqueous ammonium chloride solution (1.00 mL) and stirred vigorously at room temperature for 1 h. The reaction mixture was filtered through Celite, and the filtrate was concentrated, and diluted with EtOAc and saturated aqueous $NaHCO_3$. The aqueous layer was extracted with EtOAc (3×10 mL), dried ($Na_2SO_4$), filtered, and concentrated in vacuo. A solution of the yellow residue in dry $CH_2Cl_2$ (20 mL) was treated with diisopropylethylamine (0.21 mL, 1.20 mmol), followed by cyclopropyl chloroformate (0.50 mL, 1.00 mmol). The resulting mixture was stirred vigorously at room temperature for 4 h, and quenched with saturated aqueous $NaHCO_3$ solution. The aqueous layer was extracted with $CH_2Cl_2$ (3×10 mL), and the combined organic layers were dried ($Na_2SO_4$), concentrated under reduced pressure and purified by chromatography on $SiO_2$ (EtOAc/hexanes, 1:4 to 3:7, containing $Et_3N$ (1%)) to yield a light yellow solid that was recrystallized from $CH_2Cl_2$/hexanes to afford RL-50 (0.089 g. 20%) as a colorless solid: Mp 126-128° C.; IR (ATR) 3365, 1721, 1514, 1330, 1170, 1127 $cm^{-1}$; $^1H$ NMR (400 MHz, DMSO-$d_6$, 373 K) δ 8.05 (brs, 1H), 7.66 (t, 1H, J=7.6 Hz), 7.57-7.37 (m, 2H), 5.56 (t, 1H, J=6.8 Hz), 4.57 (d, 2H, J=6.8 Hz), 4.52 (brs, 2H), 4.04 (sept, 1H, J=3.2 Hz), 0.71-0.57 (m, 4H); $^{13}C$ NMR (151 MHz, $CD_3OD$) δ 161.7 (d, J=247.5 Hz), 158.3, 146.2 (ddd, J=238.5, 12.0, 3.0 Hz), 138.9 (d, J=226.9 Hz), 135.3 (d, J=232.2 Hz), 133.6 (d, J=14.6 Hz), 132.0 (qd, J=33.2, 8.2 Hz), 131.6 (d, J=14.1 Hz), 131.2 (d, J=4.2 Hz), 126.7 (t, J=11.6 Hz), 124.9 (qd, J=268.5, 2.4 Hz), 122.3-122.0 (m), 113.5 (dq, J=25.4, 3.5 Hz), 104.1-103.8 (m), 50.7, 43.7, 5.5; $^{19}F$ NMR (565 MHz, $CD_3OD$) δ −64.1 (s, 3F), −119.0 (s, 1F), −153.7 (dd, 1F, J=20.9, 7.3 Hz), −158.7 (d, 1F, J=5.7 Hz), −172.0 (d, 1F, J=21.4 Hz); HRMS (HESI) m/z calcd for $C_{18}H_{15}N_3O_2F_7$ $[M+H]^+$ 438.1047, found 438.1044.

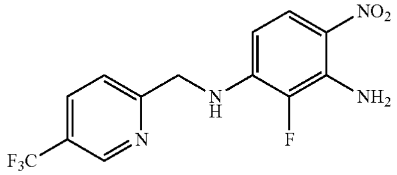 [SMILES: Nc1c([N+](=O)[O-])ccc(NCc2ccc(C(F)(F)F)cn2)c1F]

2-Fluoro-4-nitro-N[1]-((5-(trifluoromethyl)pyridin-2-yl)methyl)benzene-1,3-diamine (5i). 2-(Aminomethyl)-5-(trifluoromethyl)pyridine hydrochloride (0.180 g, 0.804 mmol) was neutralized with 1 M NaOH (0.84 mL). The resulting aqueous solution was extracted with $CH_2Cl_2$ (3×). The combined organic layers were dried ($Na_2SO_4$), and concentrated in vacuo to give a yellowish oil that was dissolved in dry DMSO (1.6 mL) and treated with 2,3-difluoro-6-nitroaniline 4a (0.144 g, 0.804 mmol) followed by $Et_3N$ (0.12 mL, 0.885 mmol) and 12 (8 mg, 0.03 mmol, 0.04 equiv). The reaction mixture was heated to 120° C. for 30 h, cooled to room temperature, diluted with water (15 mL) and extracted with $CH_2Cl_2$ (3×10 mL). The combined organic layers were washed with brine (2×10 mL), dried ($Na_2SO_4$), filtered and concentrated under reduced pressure. The residue was purified by chromatography on $SiO_2$ (acetone/hexanes, 1:8 to 1:5 to 1:4, containing $Et_3N$ (0.2%)) to give 5i (0.20 g, 75%) as a yellow solid: Mp 138.2-138.5° C.; IR (ATR) 3484, 3370, 1629, 1607, 1551, 1482, 1325, 1282, 1251, 1126, 1077, 1018, 755 $cm^{-1}$; $^1H$ NMR (400 MHz, $CDCl_3$) δ 8.88 (s, 1H), 7.95-7.87 (m, 2H), 7.44 (d, 1H, J=8.4 Hz), 6.10-6.05 (m, 3H), 5.72 (br s, 1H), 4.66 (d, 2H, J=5.6 Hz); $^{13}C$ NMR (100 MHz, $CDCl_3$) δ 160.4, 146.5 (q, J=4.0 Hz), 140.7 (d, J=9.0 Hz), 138.1 (d, J=227.0 Hz), 135.3 (d, J=13.0 Hz), 134.2 (q, J=3.5 Hz), 126.0 (q, J=33.0 Hz), 125.6 (d, J=3.0 Hz), 123.7 (d, J=3.0 Hz), 123.5 (q, J=271.0 Hz), 121.3, 100.9 (d, J=3.0 Hz), 47.8; $^{19}F$ NMR (376 MHz, $CDCl_3$) δ −62.3 (s, 3F), −160.5 (s, 1F); HRMS (HESI) m/z calcd for $C_{13}H_{10}N_4O_2F_4$ $[M+H]^+$ 330.0813, found 330.0811.

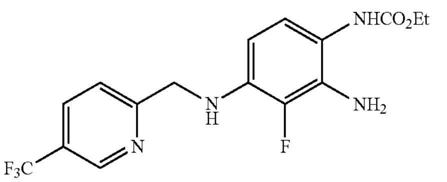

Ethyl (2-amino-3-fluoro-4-(((5-(trifluoromethyl)pyridin-2-yl)methyl)amino)phenyl)carbamate (RL-31). A solution of 5i (0.165 g, 0.5 mmol) in EtOH (2.5 mL) was treated with 10% Pd/C (0.025 g) under $N_2$ and stirred at room temperature for 5 h under a atmosphere of $H_2$ (balloon). The reaction mixture was filtered through Celite ($CH_2Cl_2$), and concentrated in vacuo to afford a brown solid (0.135 g, 0.43 mmol, 90%) that was dissolved in $CH_2Cl_2$ (8 mL) and treated under argon at 0° C. with diisopropylethylamine (0.08 mL, 0.48 mmol) followed by ethyl chloroformate (0.038 mL, 0.39 mmol) dropwise at 0° C. The reaction mixture was stirred for 4 h at 0° C., quenched with water, and extracted with $CH_2Cl_2$ (3×5 mL). The combined organic extracts were dried ($Na_2SO_4$), concentrated under reduced pressure, and purified by chromatography on $SiO_2$ (hexanes/EtOAc, 2:1 to 1:1, in the presence of $Et_3N$ (1%)) to yield a light yellow solid (0.078 g, 43%) that was recrystallized ($CH_2Cl_2$/hexanes) to afford RL-31 (0.048 g) as a colorless solid: Mp 153.6-154.2° C.; IR (ATR) 3303, 1685, 1638, 1540, 1532, 1528, 1329, 1260, 1128, 764, 751 $cm^{-1}$; $^1H$ NMR (400 MHz, $CDCl_3$) δ 8.84 (s, 1H), 7.86 (dd, 1H, J=8.4, 2.0 Hz), 7.46 (d, 1H, J=8.4 Hz), 6.72 (d, 1H, J=8.4 Hz), 6.30 (br s, 1H), 5.96 (t, 1H, J=8.8 Hz), 4.85 (br s, 1H), 4.53 (d, 2H, J=5.6 Hz), 4.18 (q, 2H, J=7.2 Hz), 3.88 (brs, 2H), 1.27 (t, 3H, J=7.2 Hz); $^{13}C$ NMR (100 MHz, $CDCl_3$) δ 162.9, 155.5, 146.4 (q, J=4.0 Hz), 141.4 (d, J=230.4 Hz), 134.7 (d, J=9.8 Hz), 134.0 (q, J=3.4 Hz), 131.0, 125.3 (q, J=33.0 Hz), 123.6 (q, J=272.2 Hz), 121.7, 121.1, 115.5, 101.8, 61.7, 49.1, 14.7; $^{19}F$ NMR (376 MHz, $CDCl_3$) δ −62.3 (s, 3F), −155.8 (s, 1F); HRMS (HESI) m/z calcd for $C_{16}H_{17}N_4O_2F_4$ $[M+H]^+$ 373.1282, found 373.1280.

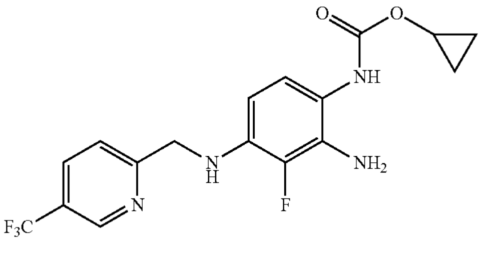 [SMILES: Nc1c(NC(=O)OC2CC2)ccc(NCc2ccc(C(F)(F)F)cn2)c1F]

Cyclopropyl (2-amino-3-fluoro-4-(((5-(trifluoromethyl)pyridin-2-yl)methyl)amino)phenyl)carbamate (RL-68). A mixture of 5i (0.33 g, 1.00 mmol) and zinc powder (0.327 g, 5.00 mmol) in MeOH (10 mL) was treated dropwise with 5 M aqueous ammonium chloride solution (1.00 mL, 5.00 mmol) and stirred vigorously at room temperature for 1 h. The reaction mixture was filtered through Celite, and the filtrate was concentrated, diluted with EtOAc and saturated aqueous $NaHCO_3$. The aqueous layer was extracted with EtOAc (3×10 mL), dried ($Na_2SO_4$), filtered, concentrated in vacuo, and dissolved in dry $CH_2Cl_2$ (20 mL). After addition of diisopropylethylamine (0.21 mL, 1.20 mmol) and cyclopropyl chloroformate (0.50 mL, 1.00 mmol), the reaction mixture was stirred vigorously at room temperature for 4 h and quenched with saturated aqueous $NaHCO_3$. The aqueous layer was extracted with $CH_2Cl_2$ (3×10 mL), and the combined organic extracts were dried ($Na_2SO_4$), concentrated under reduced pressure, and purified by chromatography on $SiO_2$ (EtOAc/hexanes, 3:7 to 1:1, containing $Et_3N$ (1%)) to yield a light yellow solid that was recrystallized ($CH_2Cl_2$/hexanes) to afford RL-68 (0.089 g, 23%) as a colorless solid: Mp 170-171° C.; IR (ATR) 3308, 1691, 1529, 1327, 1123, 1079, 1020, 768 $cm^{-1}$; $^1H$ NMR (600 MHz, $CD_3OD$) δ 8.81 (s, 1H), 8.02 (d, 1H, J=7.8 Hz), 7.60 (d, 1H, J=7.8 Hz), 6.65 (d, 1H, J=7.2 Hz), 5.89 (t, 1H, J=7.8 Hz), 4.53 (s, 2H), 4.10-3.97 (m, 1H), 0.87-0.42 (m, 4H); $^{13}C$ NMR (151 MHz, $CD_3OD$) δ 165.9, 158.4, 146.8, 142.4 (d, J=230.2 Hz), 136.0, 135.5, 132.6, 126.3 (q, J=33.0 Hz), 125.2 (q, J=271.9 Hz), 123.0, 122.7, 116.4, 102.2, 50.3, 49.6, 5.5; $^{19}F$ NMR (565 MHz, $CD_3OD$) δ −63.7 (s, 3F), −157.8 (s, 1F); HRMS (HESI) m/z calcd for $C_{17}H_{127}N_4O_2F_4$ $[M+H]^+$ 385.1282, found 385.1280.

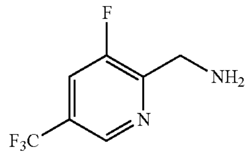 [SMILES: NCc1ncc(C(F)(F)F)cc1F]

(3-Fluoro-5-(trifluoromethyl)pyridin-2-yl)methanamine (3f). A solution of 3-fluoro-5-(trifluoromethyl)picolinonitrile (2.20 g, 11.57 mmol) in MeOH (20 mL) was treated with 10% Pd/C (0.616 g, 0.579 mmol) and concentrated HCl (1.07 mL, 12.73 mmol) and stirred at room temperature for 15 h under an atmosphere of $H_2$ (balloon). The reaction mixture was filtered through Celite, and the Celite was washed with MeOH and water. The filtrate was concentrated to remove the MeOH, treated with additional water, and the aqueous solution was extracted with $CH_2Cl_2$ (3×10 mL). The aqueous layer was treated with 1 N NaOH (13 mL) and extracted with $CH_2Cl_2$ (3×15 mL). The combined organic layers were dried ($Na_2SO_4$), filtered, concentrated in vacuo to afford 3f as green-blue oil (1.32 g, 59%): IR (ATR) 3377, 2913, 1416, 1333, 1127, 932 $cm^{-1}$; $^1H$ NMR (400 MHz, $CDCl_3$) δ 8.51 (s, 1H), 7.45 (d, 1H, J=8.8 Hz), 3.96 (s, 2H); $^{13}C$ NMR (100 MHz, $CDCl_3$) δ 156.1 (d, J=258.0 Hz), 154.3 (d, J=15.0 Hz), 141.8-141.5 (m), 126.3 (qd, J=33.0, 3.0 Hz), 122.6 (qd, J=271.0, 1.0 Hz), 119.7 (dq, J=22.0, 3.5 Hz), 41.5; $^{19}F$ NMR (376 MHz, $CDCl_3$) δ −62.5 (s, 3F), −126.1 (s, 1F); HRMS (HESI) m/z calcd for $C_7H_7N_2F_4$ $[M+H]^+$ 195.0540, found 195.0540.

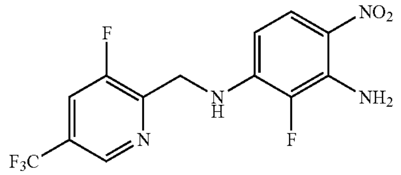 [SMILES: Nc1c([N+](=O)[O-])ccc(NCc2ncc(C(F)(F)F)cc2F)c1F]

2-Fluoro-$N^1$-((3-fluoro-5-(trifluoromethyl)pyridin-2-yl)methyl)-4-nitrobenzene-1,3-diamine (5j). An oven-dried sealable vial was charged with 3f (0.46 g, 2.37 mmol) and 2,3-difluoro-6-nitroaniline 4a (0.433 g, 2.49 mmol evacuated and backfilled with $N_2$ (3×), and treated with dry DMSO (2.5 mL) followed by $Et_3N$ (0.37 mL, 2.61 mmol) and 12 (0.030 g, 0.118 mmol). The vial was sealed and the reaction mixture was heated to 100° C. for 6 h, cooled to room temperature, diluted with water (30 mL) and extracted with EtOAc (3×10 mL). The combined organic layers were washed with brine (2×5 mL), dried ($Na_2SO_4$), filtered and concentrated under reduced pressure. The residue was purified by chromatography on $SiO_2$ (EtOAc/hexanes, 1:4, containing $Et_3N$ (0.5%)) to afford 5j (0.37 g, 45%) as a yellow solid: Mp 158.9-161.2° C.; IR (ATR) 3385, 1629, 1483, 1418, 1334, 1278, 1126, 933, 741 $cm^{-1}$; $^1H$ NMR (600 MHz, acetone-$d_6$) δ 8.78 (s, 1H), 8.07 (d, 1H, J=9.6 Hz), 7.81 (dd, 1H, J=9.6, 1.2 Hz), 6.69 (brs, 2H), 6.50 (brs, 1H), 6.39 (dd, 1H, J=9.6, 8.4 Hz), 4.85 (d, 2H, J=5.4 Hz); $^{13}C$ NMR (151 MHz, acetone-$d_6$) δ 157.7 (d, J=260.0 Hz), 151.1 (d, J=15.3 Hz), 142.5-142.3 (m), 142.2 (d, J=9.5 Hz), 138.7 (d, J=228.2 Hz), 136.6 (d, J=13.2 Hz), 127.5 (qd, J=33.5, 3.5 Hz), 125.6 (d, J=3.7 Hz), 123.9 (q, J=272.2 Hz), 123.8 (d, J=2.9 Hz), 121.5 (dq, J=21.7, 3.6 Hz), 101.8 (d, J=3.0 Hz), 43.1; $^{19}F$ NMR (376 MHz, $CDCl_3$) δ −62.1 (s, 3F), −124.7 (s, 1F), −160.5 (s, 1F); HRMS (HESI) calcd for $C_{13}H_{10}N_4O_2F_5$ $[M+H]^+$ 349.0718, found 349.0716.

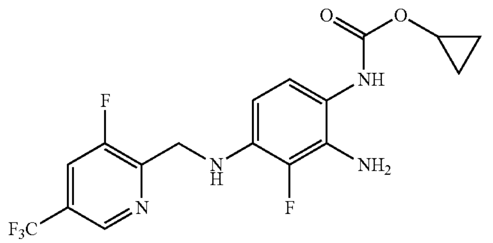 [SMILES: Nc1c(NC(=O)OC2CC2)ccc(NCc2ncc(C(F)(F)F)cc2F)c1F]

Cyclopropyl (2-amino-3-fluoro-4-(((3-fluoro-5-(trifluoromethyl)pyridin-2-yl)methyl)amino)phenyl)carbamate (RL-96). A solution of 5j (0.23 g, 0.66 mmol) in MeOH (7 mL) was treated with zinc powder (0.216 g, 3.30 mmol) followed by a 5 M aqueous ammonium chloride solution (0.66 mL, 3.30 mmol). The reaction mixture was stirred vigorously at room temperature for 2 h, filtered through Celite, and the filtrate was concentrated, diluted with EtOAc and saturated aqueous $NaHCO_3$. The aqueous layer was extracted with EtOAc (3×10 mL), and the combined organic layers were dried ($Na_2SO_4$), filtered, and concentrated in vacuo. A solution of the residue in dry $CH_2Cl_2$ (20 mL) was treated with diisopropylethylamine (0.14 mL, 0.79 mmol) followed by a 1 M solution of cyclopropyl chloroformate in toluene (0.66 mL, 0.66 mmol). The reaction mixture was stirred vigorously at room temperature for 4 h, and quenched with saturated aqueous $NaHCO_3$. The aqueous layer was extracted with $CH_2Cl_2$ (3×10 mL), and the combined organic extracts were dried ($Na_2SO_4$), evaporated under reduced pressure, and purified by chromatography on $SiO_2$ (EtOAc/hexanes, 3:7 to 1:1, containing $Et_3N$ (1%)) to yield a light-yellow solid that was recrystallized ($CH_2Cl_2$/hexanes) to afford RL-96 (0.088 g, 33%) as a colorless solid: Mp 162.6-163.5° C.; IR (ATR) 3333, 1701, 1540, 1415, 1331, 1130 $cm^{-1}$; $^1H$ NMR (600 MHz, $CDCl_3$) δ 8.69 (s, 1H), 7.63 (d, 1H, J=8.4 Hz), 6.81 (s, 1H), 6.27-6.19 (d, 1H, J=8.4 Hz), 6.15 (br s, 1H), 4.56 (s, 2H), 4.18-4.08 (m, 1H), 3.84 (br s, 2H), 0.80-0.55 (m, 4H); $^{13}C$ NMR (151 MHz, $CDCl_3$) δ 156.7 (d, J=260.8 Hz), 155.6, 150.3 (d, J=14.9 Hz), 142.0-141.6 (m), 141.8 (d, J=231.8 Hz), 134.7, 130.7, 127.1 (q, J=33.7 Hz), 122.7 (q, J=272.6 Hz), 121.5, 120.3 (dq, J=21.6, 3.3 Hz), 115.6, 102.3, 49.9, 43.2, 5.3; $^{19}F$ NMR (376 MHz, $CDCl_3$) δ −62.1 (s, 3F), −124.9 (s, 1F), −155.4 (s, 1F); HRMS (HESI) m/z calcd for $C_{17}H_{16}N_4O_2F_5$ $[M+H]^+$ 403.1188, found 403.1185.

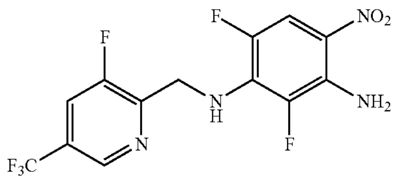 [SMILES: Nc1c([N+](=O)[O-])cc(F)c(NCc2ncc(C(F)(F)F)cc2F)c1F]

2,6-Difluoro-$N^1$-((3-fluoro-5-(trifluoromethyl)pyridin-2-yl)methyl)-4-nitrobenzene-1,3-diamine (5k). An oven-dried sealable vial was charged with 3f (0.243 g, 1.25 mmol) and 2,3,4-trifluoro-6-nitroaniline 4c (0.200 g, 1.04 mmol), evacuated and backfilled with Na (3×), and charged with dry DMSO (2 mL), $Et_3N$ (0.18 mL, 1.25 mmol) and $I_2$ (0.132 g, 0.520 mmol). The vial was sealed and the reaction mixture was heated to 60° C. for 30 h before cooling to room temperature, diluted with water (20 mL) and extracted with EtOAc (3×10 mL). The combined organic layers were washed with brine (2×5 mL), dried ($Na_2SO_4$), filtered, concentrated under reduced pressure, and purified by chromatography on $SiO_2$ (EtOAc/hexanes, 1:4, containing $Et_3N$ (0.2%)) to afford 5k (0.221 g, 58%) as a yellow solid: Mp 157.6-158.4° C.; IR (ATR) 3314, 1548, 1474, 1412, 1339, 1256, 1136 $cm^{-1}$; $^1H$ NMR (400 MHz, acetone-$d_6$) δ 8.78 (s, 1H), 8.07 (d, 1H, J=9.2 Hz), 7.61 (d, 1H, J=9.2 Hz), 6.76 (brs, 2H), 6.40 (brs, 1H), 5.02 (s, 2H); $^{13}C$ NMR (100 MHz, acetone-$d_6$) δ 157.2 (d, J=259.6 Hz), 151.4 (d, J=15.0 Hz), 143.6 (dd, J=231.8, 8.8 Hz), 142.6-142.2 (m), 139.2 (dd, J=230.7, 7.0 Hz), 135.9 (d, J=14.6 Hz), 133.4 (dd, J=15.6, 10.7 Hz), 127.4 (qd, J=33.6, 3.6 Hz), 123.9 (q, J=271.9 Hz), 121.8-121.4 (m), 121.4 (dq, J=22.0, 3.6 Hz), 107.4 (dd, J=24.9, 2.1 Hz), 44.5-44.3 (m); $^{19}F$ NMR (376 MHz, acetone-$d_6$) δ −62.1 (s, 3F), −125.1 (s, 1F), −143.3 (d, 1F, J=6.6 Hz), −155.7 (d, 1F, J=6.6 Hz); HRMS (HESI) m/z calcd for $C_{13}H_9N_4O_2F_6$ $[M+H]^+$ 367.0624, found 367.0623.

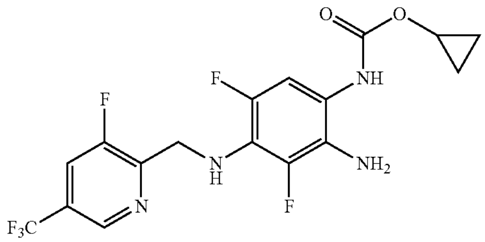 [SMILES: Nc1c(NC(=O)OC2CC2)cc(F)c(NCc2ncc(C(F)(F)F)cc2F)c1F]

Cyclopropyl (2-amino-3,5-difluoro-4-(((3-fluoro-5-(trifluoromethyl)pyridin-2-yl)methyl)amino)phenyl)carbamate (RL-01). A solution of 5k (0.220 g, 0.601 mmol) in MeOH (6 mL) was treated with zinc powder (0.196 g, 3.00 mmol) followed by a 5 M aqueous ammonium chloride solution (0.60 mL, 3.00 mmol). The reaction mixture was stirred vigorously at room temperature for 2 h, filtered through Celite, and the filtrate was concentrated in vacuo, diluted with EtOAc and saturated aqueous $NaHCO_3$. The aqueous layer was extracted with EtOAc (3×10 mL), and the combined organic layers were dried ($Na_2SO_4$), filtered, and concentrated in vacuo. A solution of the residue in dry $CH_2Cl_2$ (12 mL) was treated with diisopropylethylamine (0.125 mL, 0.721 mmol) followed by cyclopropyl chloroformate (0.43 mL, 0.600 mmol). The reaction mixture was stirred vigorously at room temperature for 4 h, quenched with saturated aqueous $NaHCO_3$, and extracted with $CH_2Cl_2$ (3×10 mL). The combined organic extracts were dried ($Na_2SO_4$), concentrated under reduced pressure, and purified by chromatography on $SiO_2$ (EtOAc/hexanes, 3:7 to 1:1, containing $Et_3N$ (1%)) to give a crude product that was recrystallized ($CH_2Cl_2$/hexanes) to afford RL-01 (0.093 g, 37%) as a colorless solid: Mp 137-138° C.; IR (ATR) 3366, 1714, 1523, 1336, 1234, 1136 $cm^{-1}$; $^1H$ NMR (600 MHz, $CDCl_3$) δ 8.68 (s, 1H), 7.60 (d, 1H, J=9.0 Hz), 6.91 (s, 1H), 6.46 (s, 1H), 4.90 (brs, 1H), 4.71 (s, 2H), 4.14-4.07 (m, 1H), 3.42 (brs, 2H), 0.78-0.60 (m, 4H); $^{13}C$ NMR (151 MHz, $CDCl_3$) δ 156.4 (d, J=260.8 Hz), 155.0, 150.7 (d, J=15.6 Hz), 146.6 (d, J=230.7 Hz), 144.0 (d, J=224.2 Hz), 141.9-141.6 (m), 127.0 (qd, J=33.9, 3.0 Hz), 125.4, 123.2, 122.7 (q, J=272.9 Hz), 120.3 (dq, J=21.5, 3.3 Hz), 116.8, 107.1, 50.0, 45.4, 5.2; $^{19}F$ NMR (565 MHz, $CDCl_3$) δ −62.1 (s, 3F), −125.2 (s, 1F), −139.5 (s, 1F), −147.1 (s, 1F); HRMS (HESI) m/z calcd for $C_{17}H_{15}N_4O_2F_6$ $[M+H]^+$ 421.1094, found 421.1093.

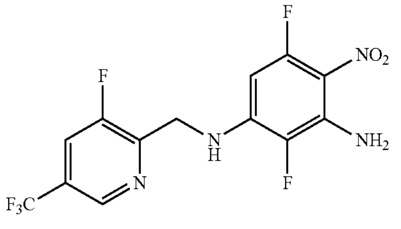 [SMILES: Nc1c(F)c(NCc2ncc(C(F)(F)F)cc2F)cc(F)c1[N+](=O)[O-]]

2,5-Difluoro-N1-((3-fluoro-5-(trifluoromethyl)pyridin-2-yl)methyl)-4-nitrobenzene-1,3-diamine (5l). An oven-dried sealable vial was charged with 3f (0.364 g, 1.87 mmol) and 2,3,5-trifluoro-6-nitroaniline 4d (0.300 g, 1.56 mmol), evacuated and back filled with $N_2$ (3×), and charged with dry DMSO (3 mL) followed by $Et_3N$ (0.24 mL, 1.72 mmol) and $I_2$ (0.198 g, 0.781 mmol). The vial was sealed and the reaction mixture was heated to 60° C. for 30 h, cooled to room temperature, diluted with water (30 mL) and extracted with EtOAc (3×15 mL). The combined organic layers were washed with brine (2×10 mL), dried ($Na_2SO_4$), filtered and concentrated under reduced pressure. The residue was purified by chromatography on $SiO_2$ (acetone/hexanes, 1:4, containing $Et_3N$ (0.2%)) to yield a yellow solid that was recrystallized (EtOAc) to afford 5l (0.21 g, 37%) as yellow powder: Mp 181-182° C.; IR (ATR) 3387, 1639, 1334, 1276, 1137 $cm^{-1}$; $^1H$ NMR (400 MHz, DMSO-$d_6$) δ 8.81 (s, 1H), 8.29 (d, 1H, J=9.2 Hz), 7.39 (brs, 1H), 6.90 (s, 2H), 6.22 (dd, 1H, J=15.2, 7.2 Hz), 4.72 (d, 2H, J=5.6 Hz); $^{13}C$ NMR (151 MHz, DMSO-$d_6$) δ 156.6 (d, J=260.0 Hz), 155.1 (d, J=252.7 Hz), 150.7 (d, J=14.6 Hz), 141.7-141.5 (m), 141.0 (dd, J=10.7, 14.6 Hz), 135.7 (d, J=14.0 Hz), 133.2 (d, J=226.6 Hz), 125.8 (qd, J=33.1, 3.4 Hz), 122.9 (q, J=272.8 Hz), 121.1 (dq, J=21.9, 3.2 Hz), 115.0 (dd, J=10.6, 3.2 Hz), 88.7 (d, J=28.7 Hz), 42.1; $^{19}F$ NMR (376 MHz, acetone-$d_6$) δ −60.5 (s, 3F), −119.1 (d, 1F, J=11.3 Hz), −123.8 (s, 1F), −160.6 (d, 1F, J=11.3 Hz); HRMS (HESI) m/z calcd for $C_{13}H_9N_4O_2F_6$ $[M+H]^+$ 367.0624, found 367.0621.

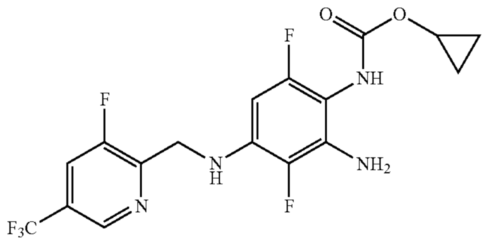 [SMILES: Nc1c(F)c(NCc2ncc(C(F)(F)F)cc2F)cc(F)c1NC(=O)OC1CC1]

Cyclopropyl (2-amino-3,6-difluoro-4-(((3-fluoro-5-(trifluoromethyl)pyridin-2-yl)methyl)amino)phenyl)carbamate (RL-12). A solution of 5l (0.200 g, 0.546 mmol) in MeOH (6 mL) was treated with zinc powder (0.179 g, 2.73 mmol) followed by a 5 M aqueous ammonium chloride solution (0.55 mL, 2.73 mmol). The reaction mixture was stirred vigorously at room temperature for 2 h, filtered through Celite, and the filtrate was concentrated, diluted with EtOAc and saturated aqueous $NaHCO_3$. The aqueous layer was extracted with EtOAc (3×10 mL), dried ($Na_2SO_4$), filtered, and concentrated in vacuo. A solution of the residue in dry $CH_2Cl_2$ (10 mL) was treated with diisopropylethylamine (0.12 mL, 0.68 mmol) followed by cyclopropyl chloroformate (0.39 mL, 0.546 mmol), stirred vigorously at room temperature for 4 h, and quenched with saturated aqueous $NaHCO_3$. The aqueous layer was extracted with $CH_2Cl_2$ (3×10 mL), and the combined organic extracts were dried ($Na_2SO_4$), concentrated under reduced pressure, and purified by chromatography on $SiO_2$ (EtOAc/hexanes, 3:7 to 1:1, containing $Et_3N$ (1%)) to yield a beige solid that was recrystallized ($CH_2Cl_2$/hexanes) to afford RL-12 (0.095 g, 41%) as an off-white solid: Mp 200-202° C.; IR (ATR) 3345, 1695, 1660, 1344, 1278, 1128 $cm^{-1}$; $^1H$ NMR (600 MHz, DMSO-$d_6$) δ 8.84 (s, 1H), 8.28 (d, J=9.6 Hz, 1H), 8.17 (s, 1H), 6.07 (brs, 1H), 5.94-5.85 (m, 1H), 4.94 (s, 2H), 4.55 (d, J=5.4 Hz, 2H), 4.03-3.86 (m, 1H), 0.72-0.38 (m, 4H); $^{13}C$ NMR (151 MHz, DMSO-$d_6$) δ 156.7 (d, J=259.5 Hz), 155.7 (d, J=236.1 Hz), 155.5, 151.6 (d, J=14.4 Hz), 141.8-141.4 (m), 135.6 (d, J=225.4 Hz), 135.7-135.3 (m), 134.5, 125.5 (qd, J=33.0, 3.5 Hz), 122.9 (q, J=272.7 Hz), 121.0 (dq, J=22.1, 3.2 Hz), 100.8 (d, J=16.1 Hz), 86.4 (d, J=27.4 Hz), 48.8, 42.7, 4.8; $^{19}F$ NMR (565 MHz, DMSO-$d_6$) δ −60.5 (s, 3F), −124.0 (s, 1F), −126.3 (d, 1F, J=11.3 Hz), −160.5 (d, 1F, J=11.3 Hz); HRMS (HESI) m/z calcd for $C_{17}H_{15}N_4O_2F_6$ $[M+H]^+$ 421.1094, found 421.1091.

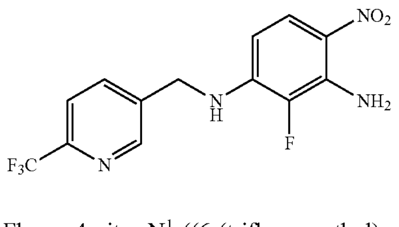

2-Fluoro-4-nitro-$N^1$-((6-(trifluoromethyl)pyridin-3-yl)methyl)benzene-1,3-diamine (5m). A solution of 3-(aminomethyl)-6-(trifluoromethyl)pyridine 3g (0.200 g, 1.08 mmol) and 2,3-difluoro-6-nitroaniline 4a (0.203 g, 1.13 mmol) in dry DMSO (2 mL) was treated under $N_2$ with $Et_3N$ (0.16 mL, 1.19 mmol) and $I_2$ (11 mg, 0.04 mmol). The reaction mixture was heated to 120° C. for 30 h, cooled to room temperature, diluted with water (20 mL), and extracted with EtOAc (3×10 mL). The combined organic layers were washed with brine (2×10 mL), dried ($Na_2SO_4$), filtered, and concentrated under reduced pressure. The residue was purified by chromatography on $SiO_2$ (acetone/hexanes, 1:8 to 1:5 to 1:4, containing $Et_3N$ (1%)) to afford 5m (0.302 g, 85%) as a yellow solid: Mp 151.8-152.2° C.; IR (ATR) 3478, 3364, 1631, 1484, 1335, 1286, 1251, 1178, 1131, 1085 $cm^{-1}$; $^1H$ NMR (400 MHz, acetone-$d_6$) δ 8.81 (s, 1H), 8.08 (d, 1H, J=8.0 Hz), 7.82 (d, 1H, J=8.4 Hz), 7.78-7.75 (m, 1H), 6.71 (brs, 3H), 6.27-6.21 (m, 1H), 4.80 (d, 2H, J=6.4 Hz); $^{13}C$ NMR (100 MHz, acetone-$d_6$) δ 150.2, 147.2 (q, J=34.0 Hz), 142.0 (d, J=9.0 Hz), 139.6, 138.6 (d, J=228.0 Hz), 137.3, 136.7 (d, J=13.0 Hz), 125.6 (d, J=4.0 Hz), 123.9 (d, J=2.0 Hz), 122.8 (q, J=271.0 Hz), 121.2 (q, J=2.7 Hz), 101.5 (d, J=3.3 Hz), 44.2; $^{19}F$ NMR (376 MHz, acetone-$d_6$) δ −68.2 (s, 3F), −160.3 (s, 1F); HRMS (HESI) m/z calcd for $C_{13}H_{11}N_4O_2F_4$ $[M+H]^+$ 331.0813, found 331.0811.

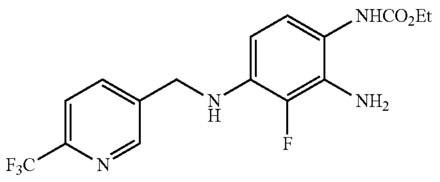

Ethyl (2-amino-3-fluoro-4-(((6-(trifluoromethyl)pyridin-3-yl)methyl)amino)phenyl)carbamate (RL-24). A solution of 5m (0.28 g, 0.85 mmol) in EtOH (4 mL) was charged with 10% Pd/C (0.046 g) under $N_2$ and stirred at room temperature for 5 h under an atmosphere of $H_2$ (balloon). The reaction mixture was filtered through Celite ($CH_2Cl_2$), and concentrated in vacuo to afford a red orange solid (0.235 g, 0.78 mmol, 92%) that was added under argon at 0° C. to a solution of diisopropylethylamine (0.15 mL, 0.86 mmol) in $CH_2Cl_2$ (16 mL). Ethyl chloroformate (0.070 mL, 0.70 mmol) was added dropwise via syringe at 0° C. The resulting mixture was stirred for 4 h at 0° C., quenched with water, and extracted with $CH_2Cl_2$ (3×10 mL). The combined organic extracts were dried ($Na_2SO_4$), concentrated under reduced pressure, and purified by chromatography on $SiO_2$ (hexanes/EtOAc, 2:1 to 1:1 to 1:2, containing $Et_3N$ (1%)) to yield a yellow solid (0.190 g, 65%) that was recrystallized ($CH_2Cl_2$/hexanes) to afford RL-24 (0.162 g) as a colorless solid: Mp 149.6-149.9° C.; IR (ATR) 2962, 3312, 3295, 1676, 1521, 1486, 1474, 1454, 1340, 1137, 1130, 1115, 1087, 779, 719, 714 $cm^{-1}$; $^1H$ NMR (500 MHz, $CDCl_3$) δ 8.71 (s, 1H), 7.86 (d, 1H, J=8.0 Hz), 7.65 (d, 1H, J=8.0 Hz), 6.74 (d, 1H, J=8.5 Hz), 6.13 (brs, 1H), 5.96 (t, 1H, J=8.5 Hz), 4.48 (d, 2H, J=6.0 Hz), 4.35 (brs, 1H), 4.19 (q, 2H, J=7.0 Hz), 3.88 (brs, 2H), 1.29 (t, 3H, J=7.0 Hz); $^{13}C$ NMR (100 MHz, $CDCl_3$) δ 155.4, 149.1, 147.3 (q, J=34.0 Hz), 141.2 (d, J=231.0 Hz), 138.4, 136.1, 134.4 (d, J=10.0 Hz), 131.0, 121.8, 121.7 (q, J=272.0 Hz), 120.5 (q, J=2.6 Hz), 115.8, 101.7, 61.7, 45.1, 14.6; $^{19}F$ NMR (471 MHz, $CDCl_3$) δ −67.8 (s, 3F), −155.7 (s, 1F); HRMS (HESI) m/z calcd for $C_{16}H_{17}N_4O_2F_4$ $[M+H]^+$ 373.1282, found 373.1276.

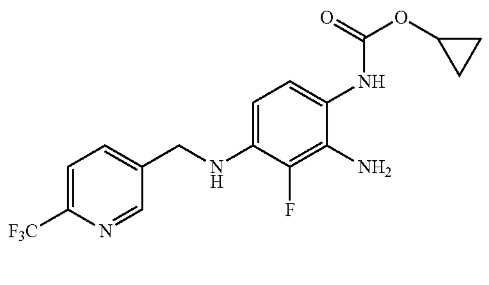 [SMILES: Nc1c(NC(=O)OC2CC2)ccc(NCc2ccc(C(F)(F)F)nc2)c1F]

Cyclopropyl (2-amino-3-fluoro-4-(((6-(trifluoromethyl)pyridin-3-yl)methyl)amino)phenyl)carbamate (RL-67). A mixture of 5m (0.200 g, 0.606 mmol) and zinc powder (0.198 g, 3.03 mmol) in MeOH (7 mL) was treated dropwise with 5 M aqueous ammonium chloride solution (0.61 mL, 3.03 mmol), and stirred vigorously at room temperature for 1 h. The reaction mixture was filtered through Celite, and the filtrate was concentrated. The residue was diluted with EtOAc and saturated aqueous $NaHCO_3$, and the aqueous layer was extracted with EtOAc (3×10 mL), dried ($Na_2SO_4$), filtered, and concentrated in vacuo. The dark red residue was dissolved in dry $CH_2Cl_2$ (12 mL) and treated with diisopropylethylamine (0.13 mL, 0.73 mmol) followed by an 0.8 M solution of cyclopropyl chloroformate in toluene (0.76 mL, 0.61 mmol). The reaction mixture was stirred vigorously at room temperature for 4 h, quenched with saturated aqueous $NaHCO_3$, and the aqueous layer was extracted with $CH_2Cl_2$ (3×10 mL). The combined organic extracts were dried ($Na_2SO_4$), concentrated in vacuo, and purified by chromatography on $SiO_2$ (EtOAc/hexanes, 3:7 to 1:1, containing $Et_3N$ (1%)) to yield a light yellow solid that was recrystallized ($CH_2Cl_2$/hexanes) to afford RL-67 (0.064 g, 28%) as a colorless solid: Mp 148-149° C.; IR (ATR) 3345, 1707, 1638, 1527, 1335, 1237, 1134, 1085, 775 $cm^{-1}$; $^1H$ NMR (400 MHz, $CDCl_3$) δ 8.71 (s, 1H), 7.87 (d, 1H, J=7.2 Hz), 7.65 (d, 1H, J=8.0 Hz), 6.76 (d, 1H, J=7.2 Hz), 6.14 (brs, 1H), 6.01 (t, 1H, J=8.8 Hz), 4.49 (s, 2H), 4.17-4.09 (m, 1H), 0.76-0.65 (m, 4H); $^1H$ NMR (600 MHz, acetone-$d_6$) δ 8.79 (s, 1H), 8.05 (d, J=7.8 Hz, 1H), 7.79 (d, J=7.8 Hz, 1H), 7.66 (brs, 1H), 6.73 (s, 1H), 5.98 (app t, J=8.4 Hz, 1H), 5.53 (brs, 1H), 4.59 (d, 2H), 4.44 (brs, 2H), 4.10-3.99 (m, 1H), 0.71-0.52 (m, 4H); $^{13}C$ NMR (151 MHz, acetone-$d_6$) δ 156.3, 150.2, 146.9 (q, J=34.1 Hz), 141.7 (d, J=238.5 Hz), 140.9, 137.2, 135.1, 132.4, 122.9 (q, J=272.9 Hz), 122.4, 121.2-121.0 (m), 116.4, 101.2, 49.6, 45.0, 5.3; $^{19}F$ NMR (565 MHz, acetone-$d_6$) δ −68.1 (s, 3F), −157.6 (s, 1F); HRMS (HESI) calcd for $C_{17}H_{17}N_4O_2F_4$ $[M+H]^+$ 385.1282, found 385.1281.

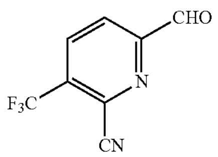 [SMILES: N#Cc1nc(C=O)ccc1C(F)(F)F]

6-Formyl-3-(trifluoromethyl)picolinonitrile (3h). A solution of TBAF (0.45 mL, 0.452 mmol) and 6-(((tert-butyldimethylsilyl)oxy)methyl)-3-(trifluoromethyl)picolinonitrile (0.13 g, 0.411 mmol) in THF (2 mL) was stirred at room temperature for 1 h, and concentrated under reduced pressure. A solution of the crude residue and $SeO_2$ (0.050 g, 0.452 mmol) in 1,4-dioxane (1 mL) was heated at 110° C. for 8 h, cooled to room temperature, filtered through Celite, and the Celite was washed ($CH_2Cl_2$). The filtrate was concentrated under reduced pressure and purified by chromatography on $SiO_2$ (EtOAc/hexanes, 1:10) to afford 3h (0.031 g, 38%) as light yellow oil: IR (ATR) 1724, 1307, 1141, 1119, 1036, 856, 762 $cm^{-1}$; $^1H$ NMR (400 MHz, $CDCl_3$) δ 10.11 (d, 1H, J=0.4 Hz), 8.34 (d, 2H, J=8.0 Hz), 8.27 (d, 2H, J=8.0 Hz); $^{13}C$ NMR (100 MHz, $CDCl_3$) δ 190.1, 155.0, 136.6 (q, J=4.0 Hz), 133.6 (q, J=34.0 Hz), 132.0, 123.9, 121.4 (q, J=273.0 Hz), 113.5; $^{19}F$ NMR (376 MHz, $CDCl_3$) δ −62.1 (s); HRMS (HESI) calcd for $C_8H_4N_{20}F_3$ $[M+H]^+$ 201.0270, found 201.0270.

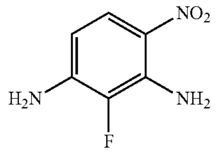 [SMILES: Nc1ccc([N+](=O)[O-])c(N)c1F]

2-Fluoro-4-nitrobenzene-1,3-diamine (4f). A microwave vial containing a solution of 2,3-difluoro-6-nitroaniline (1.00 g, 5.74 mmol) in 1,4-dioxane (5 mL) was treated with 28% aqueous ammonium hydroxide solution (4.00 mL, 28.97 mmol). The vial was sealed and heated at 95° C. for 19 h. The solvent was removed in vacuo, and the residue was diluted with EtOAc, dried ($Na_2SO_4$), filtered, concentrated in vacuo, and purified by chromatography on $SiO_2$ (acetone/hexanes, 1:3 to 1:2, containing $Et_3N$ (1%)) to afford 4f (0.85 g, 89%) as a yellow solid: Mp 174-175.5° C.; IR (ATR) 3341, 1631, 1537, 1474, 1411, 1280, 1210, 758 $cm^{-1}$; $^{1}H$ NMR (400 MHz, $CD_3OD$) δ 7.71 (dd, 1H, J=9.6, 1.6 Hz), 6.13 (dd, 1H, J=9.6, 8.4 Hz); $^{13}C$ NMR (100 MHz, $CD_3OD$) δ 143.5 (d, J=10.0 Hz), 138.3 (d, J=13.0 Hz), 138.3 (d, J=226.0 Hz), 124.8, 123.9 (d, J=2.0 Hz), 105.9 (d, J=4.0 Hz); $^{19}F$ NMR (471 MHz, $CDCl_3$) δ −159.2; HRMS (HESI) calcd for $C_6H_7N_3O_2F$ $[M+H]^+$ 172.0517, found 172.0516.

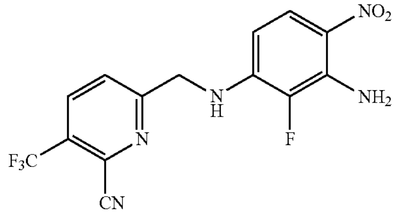 [SMILES: N#Cc1nc(CNc2ccc([N+](=O)[O-])c(N)c2F)ccc1C(F)(F)F]

6-(((3-Amino-2-fluoro-4-nitrophenyl)amino)methyl)-3-(trifluoromethyl)picolinonitrile (5n). A mixture of 3h (0.20 g, 1.00 mmol), 4f (0.171 g, 1.00 mmol), TsOH (0.017 g, 0.10 mmol) and 4 Å molecular sieves (200 mg) in dry xylene (1 mL) was heated at reflux for 1 h, cooled to room temperature, quenched with MeOH (0.5 mL) and treated with $NaBH_4$ (0.045 g, 1.20 mmol). The reaction mixture was stirred for 30 minutes, filtered, concentrated in vacuo, and the residue was purified by chromatography on $SiO_2$ (EtOAc/hexanes, 1:4 to 1:1) to afford 5n (0.11 g, 31%) as a yellow solid: Mp 195-196.5° C.; IR (ATR) 3359, 1636, 1280, 1131, 1039, 834, 757 $cm^{-1}$; $^{1}H$ NMR (400 MHz, acetone-$d_6$) δ 8.44 (d, 1H, J=8.4 Hz), 8.04 (d, 1H, J=8.4 Hz), 7.79 (d, 1H, J=9.6, 1.6 Hz), 6.75 (brs, 3H), 6.22 (d, 1H, J=9.6, 8.4 Hz), 4.91 (d, 2H, J=6.0 Hz); $^{13}C$ NMR (100 MHz, acetone-$d_6$) δ 165.6, 141.8 (d, J=10.0 Hz), 138.7 (d, J=228.0 Hz), 137.0 (q, J=4.0 Hz), 136.7 (d, J=13.0 Hz), 131.0 (q, J=2.0 Hz), 129.2 (q, J=33.0 Hz), 126.0, 125.8, 123.8 (d, J=3.0 Hz), 123.3 (q, J=271.0 Hz), 115.3, 101.5 (d, J=3.0 Hz), 48.2; $^{19}F$ NMR (471 MHz, acetone-$d_6$) δ −62.3 (s, 3F), −160.3 (s, 1F); HRMS (HESI) calcd for $C_{14}H_{10}N_5O_2F_4$ $[M+H]^+$ 356.0765, found 356.0764.

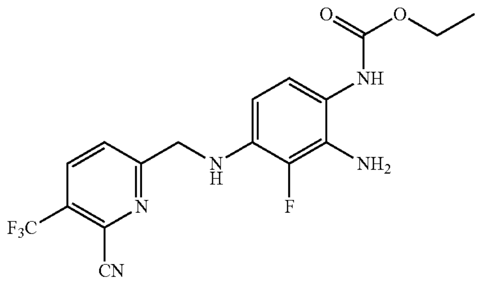 [SMILES: CCOC(=O)Nc1ccc(NCc2ccc(C(F)(F)F)c(C#N)n2)c(F)c1N]

Ethyl (2-amino-4-(((6-cyano-5-(trifluoromethyl)pyridin-2-yl)methyl)amino)-3-fluorophenyl)carbamate (RL-23). A solution of 5n (0.10 g, 0.28 mmol) in MeOH (2 mL) was treated with zinc powder (0.092 g, 1.41 mmol) followed by 5 M aqueous ammonium chloride solution (0.28 mL). The reaction mixture was stirred vigorously at room temperature for 40 min, treated with diisopropylethylamine (0.49 mL, 2.81 mmol) followed by ethyl chloroformate (0.13 mL, 1.41 mmol), stirred vigorously at room temperature for 2 h, and filtered through Celite. The filter cake was washed with EtOAc, and the filtrate was diluted with EtOAc and saturated aqueous $NaHCO_3$. The aqueous layer was extracted with EtOAc (3×5 mL), and the combined organic extracts were dried ($Na_2SO_4$), concentrated under reduced pressure, and purified by chromatography on $SiO_2$ (40-60% EtOAc/hexanes, 2:3 to 3:2, containing $Et_3N$ (1%)) to afford RL-23 (0.048 g, 43%) as a light yellow solid: Mp 153-154° C.; IR (ATR) 3367, 1690, 1527, 1308, 1227, 1143, 1124, 1038, 770 $cm^{-1}$; $^{1}H$ NMR (500 MHz, $CDCl_3$) δ 8.03 (d, 1H, J=8.5 Hz), 7.71 (d, 1H, J=8.0 Hz), 6.72 (d, 1H, J=8.5 Hz), 6.19 (brs, 1H), 5.87 (t, 1H, J=8.8 Hz), 4.59 (s, 2H), 4.19 (q, 2H, J=7.0 Hz), 1.28 (t, 3H, J=7.0 Hz); $^{13}C$ NMR (100 MHz, $CDCl_3$) δ 164.9, 155.5, 141.3 (d, J=230.0 Hz), 135.4 (q, J=5.0 Hz), 134.0 (d, J=10.0 Hz), 131.2 (d, J=12.0 Hz), 130.8 (d, J=2.0 Hz), 129.1 (q, J=34.0 Hz), 124.3, 122.0 (q, J=272.0 Hz), 121.9, 116.0, 114.3, 101.6, 61.8, 48.8, 14.7; $^{19}F$ NMR (471 MHz, $CDCl_3$) δ −61.7 (s, 3F), −155.5 (s, 1F); HRMS (HESI) m/z calcd for $C_{17}H_{16}N_5O_2F_4$ $[M+H]^+$ 398.1235, found 398.1231.

Example 2

Biological Evaluation and Effects of Fluorine Substitution

Figure 5B:
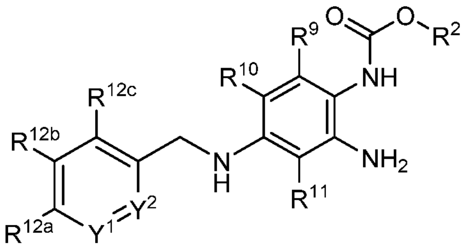

Biological evaluation of the new analogs, including RL-81 as a positive standard was performed in the Eli Lilly Open Innovation Drug Discovery (OIDD) program (now discontinued; see https://openinnovation.lilly.com/dd/log-in.jsp). Ion channel agonistic potency was determined in a high-throughput assay using the automated electrophysiology IonWorks® Barracuda™ (IWB) platform (Molecular Devices, LLC) in HEK293 cells. The results are shown in FIGS. 5A-5B. The resulting 10-point concentration-response curves provide a measure of compound efficacy by determining the agonist concentration that doubles the conductance at the voltage leading to 15% channel activation ($EC_{2x}$). The lower the $EC_{2x}$ values, the more potent the agonist.

Compared to the literature standards, flupirtine (FP) and regitabine (RG), the previous lead structure RL-81 demonstrated ca. 8-50 times higher (vs. FP) or comparable (vs. RG) efficacy at all tested $K_v7$ channels (FIG. 6A). Since the primary interest was in optimizing central ($K_v7.2/K_v7.3$)

over peripheral Kv7.4/Kv7.5) tissue activities, a selectivity index (SI) was calculated as the inverse ratio of the $EC_{2x}$ values for these two channel types:

$$SI=EC_{2x}(K_v7.4/K_v7.5)/EC_{2x}(K_v7.2/K_v7.3)$$

The higher the SI ratio, the better the selectivity of the agent for the $K_v7.2/K_v7.3$ channels.

Interestingly, RL-81 (SI=0.3) proved to be considerably more potent at $K_v7.4/K_v7.5$ than FP (SI=1.8), suggesting an adverse property profile and setting the stage for further medicinal chemistry optimizations. One of the first modifications was to move the $CF_3$ group on $R^8$ from the para- to the meta-position (i.e., from $R^{12a}$ to $R^{12b}$) in the structure of FIGS. 5A-5B). Surprisingly, the resulting analog, RL-73, was twice as potent at $K_v7.2/K_v7.3$ when RL-81, while substantially decreasing activity at $K_v7.4/K_v7.5$, resulting in a superior SI=4.7. These findings were further substantiated by the $SF_5$-containing analog RL-02, which showed an equivalent channel activity profile to RL-73, and also had a more favorable SI=1.8. Structurally, the only difference between RL-73 and RL-02 is the switch from a meta-$CF_3$- to a meta-$SF_5$-substituent, thus also validating the potential for biological mimicry between the trifluoromethyl and pentasulfanyl groups. Interestingly, while the $K_v7.2/K_v7.3$ vs. $K_v7.4/K_v7.5$ selectivity is high, both RL-73 and Rl-02 have low $EC_{2x}$, values for $K_v7.3/K_v7.5$ and $K_v7.4$ in the 0.2-0.6 μM range, comparable to RL-81's $EC_{2x}$, 0.29 and 0.10 μM. Therefore, the structural-activities studies were continued and several further modifications of RL-81 were made.

Moving the fluorine atom from $R^{11}$ to $R^{19}$ in RL-72 had a detrimental effect on the $EC_{2x}$, for $K_v7.2/K_v7.3$, reducing it 5-fold vs. RL-81 to 1.26 μM. However, the selectivity was superb with $EC_{2x}$'s of >10, 4.65, and >10 μM for $K_v7.3/K_v7.5$, $K_v7.4$, and $K_v7.4/K_v7.5$, respectively, providing an SI>7. However, installing a $CF_3$-group at the $R^{10-}$ position in RL-073 completely abrogated activity at all channel types. This position appears to be very sensitive to steric bulk.

Surprisingly, changing the ethyl group at $R^2$ to an isopropyl group slightly increased the potency of RL-32 at $K_v7.2/K_v7.3$, but vastly decreased the $K_v7.4/K_v7.5$ $EC_{2x}$, to 4.98 μM, leading to an SI=31, 100× better than the SI=0.3 of RL-81. The SI=2.5 of the corresponding cyclopropyl analog RL-56 fits this trend, since the steric dimensions of a cyclopropane are in between those of the isopropane and the ethane groups. RL-56 proved to be the most active analog on $K_v7.2/K_v7.3$ at that point, with an $EC_{2x}$ of 0.11±0.02 μM. However, both RL-32 and RL-56 also still showed <0.4 μM $EC_{2x}$ potencies at Kv7.3/Kv7.5 and $K_v7.4$ channels.

For the next SAR iteration, a 2-fluoro-4-trifluoromethylbenzylamine moiety was introduced, providing a CF group at $Y^2$ and a $CF_3$ group at $R^{12a}$, and varied fluorinations at $R^9$-$R^{11}$. The parent compound in this series, RL-18, was both potent, $EC_{2x}$=0.18±0.11 μM, and moderately selective, SI=1.7 (FIG. 5A). Changing the ethyl to cyclopropyl at $R^2$ decreased potency and SI (i.e., RL-35), but, as previously found, adding fluorines at $R^9$ or $R^{10}$ recovered a high selectivity, generating an SI>10 and >7, respectively, for RL-36 and RL-46. In agreement with the data found for RL-72, the $R^{10}$-fluorinated RL-36 also lacked agonist activity at $K_v7.3/K_v7.4$, $K_v7.4$, and $K_v7.4/K_v7.5$, and, due to its remaining sub-micromolar $EC_{2x}$=0.93 at $K_v7.2/K_v7.3$, RL-36 therefore represents an overall significant improvement over RL-81. In contrast, the hepta-fluorinated RL-50 lost all activity.

In a final round of SAR investigations, trifluoromethylated pyridines were prepared. Initially, the focus was on 2-pyridyl analogs RL-31, RL-68, RL96, RL-01, RL-12, and RL-23. With the exception of the $R^{12c}$-fluorinated RL-96 and RL-12, these analogs demonstrated either low selectivity or low potency. The $R^{12c}$, $R^9$, $R^{11}$-trifluorinated RL-12, in particular, maintained a respectable 1.00 μM $EC_{2x}$, at $K_v7.2/K_v7.3$, with an SI>10 and no detectable agonist activity at other channels. Compared to their 2-pyridyl isomers, RL-31 and Rl-68, the 3-pyridyl analogs RL-24 and RL-67 showed slightly increased selectivity, but essentially equivalent potency, demonstrating that among the studied chemotypes, the fluorination pattern is the most significant determinant of selectivity and activity.

Figure 7:
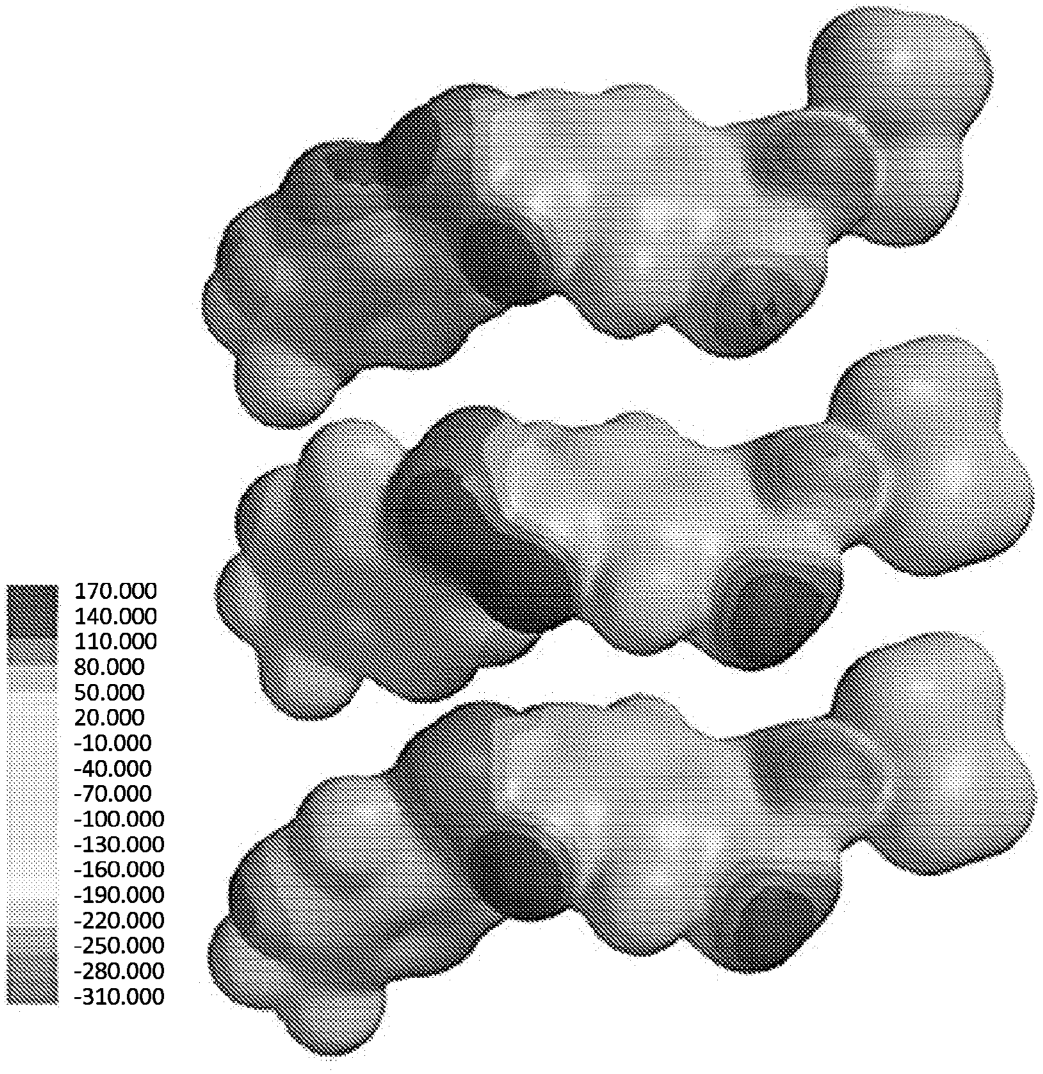
FIG. 7 shows maps of electron-density surface encoded with electrostatic potential for three disclosed compounds; colors reflect a property range from +170 kJ/mol (blue) to −310 kJ/mol (red).

Since substitution with fluorine has profound effects on the electron distribution in conjugated π-systems, we examined the electrostatically encoded electron-density surfaces of RL-81 and RL-50, which has additional fluorinations at the benzylamine moiety and, especially at $R^9$ and $R^{19}$ of the triaminobenzene, rendering it inactive at all $K_v7$ channel types (FIG. 7). Most significantly, the electron density at the carbamate oxygen and the ortho-aniline nitrogen is significantly decreased as a result of the two additional fluorinations at the triaminobenzene moiety in RL-50. In comparison, RL-46, which has only one additional fluorine atom at $R^9$ vs. RL-81 and is still moderately active, shows an intermediate electron density at the carbamate oxygen and the ortho-aniline nitrogen. Accordingly, it is hypothesized that the $K_v7.2$-5 channel potency is largely due to the electrostatic/H-bonding interactions at the carbamate oxygen and the ortho-aniline, with decreased electron density being detrimental. In contrast, steric and conformational effects at the carbamate ester and the benzylamine moieties appear to influence channel selectivity. This hypothesis is also supported by literature evidence. Based on mutation and modeling studies, the tryptophan residue W236 in $K_v7.2$ (or, analogously and respectively, W265, 242, 235 in $K_v7.3$, $K_v7.4$, $K_v7.5$) is thought to be critical for binding, and participates in hydrogen bonding interactions with carbamate or amide groups of small molecule agonists (Schenzer et al., *J. Neurosci.* 2005, 25:5051-5060; Kim et al., *Nat. Commun.* 2015, 6:8116). In contrast, Kv7.1, which lacks a corresponding W residue, is not activated by retigabine-type molecules.

An alternative, but possibly complementary, interpretation of the differential selectivities for fluorinated and heterocylic analogs of retigabine and RL-81 could be their preference for different binding sites on the channels, and hence different mechanisms of action. While retigabine binds to the pore domain on $K_v7.2$-$K_v7.5$, other compounds have been suggested to target the voltage-sensing domain (Wang et al., *J. Physiol.* 2017, 595:663-676).

In summary, analogs of the potent $K_v7$ agonist RL-81 were prepared and characterized, and several new lead structures were obtained with greatly improved selectivity for $K_v7.2/K_v7.3$ over the other tested potassium channels, i.e., $K_v7.3/K_v7.5$, $K_v7.4$, and $K_v7.4/K_v7.5$. Specifically, RL-36 and RL-12 maintained an agonist $EC_{2x}$ of ca. 1 μM on $K_v7.2/K_v7.3$ in a high-throughput assay on the automated electrophysiology IonWorks® Barracuda™ (IWB) platform in HEK293 cells, but lacked activity on $K_v7.3/K_v7.5$, $K_v7.4$, and $K_v7.4/K_v7.5$, resulting in a selectivity index SI>10. RL-56, an analog of RL-81, has ca. 3 times more potent $EC_{2x}$ of 0.11±0.02 μM. RL-56 also demonstrated an SI=2.5 for $K_v7.2/K_v7.3$ over $K_v7.4/K_v7.5$, almost an order of magnitude more selective than RL-81 (SI=0.3). Accordingly, RL-56, RL-36, and RL-12 represent promising new lead structures for the therapeutic use of selective potassium channel agonists in epilepsy, neuropathic pain, anxiety, mania, ADHD, depression, migraines, and tinnitus. Notably, the $R^{10}$ substitution on RL-36 should prevent the oxidative dimerization observed for RG. Furthermore, the SAR studies demonstrated the utility of fluorine substituents, including F, $CF_3$, and $SF_5$, to substantially alter the potency and selectivity of pharmaceutical candidates. While the utility of fluorinated drug candidates has been highlighted in particular for their increases in metabolic stability, conformational effects, pKa modulation, and for applications as bioisosteric replacements, fewer studies have focused on their effects on specific target affinity. The extensive use of fluorine as the guiding principle in iterative core structure modifications in this work further supports the versatility of fluorine substituents, including F, $CF_3$, and $SF_5$, to span orders of magnitude of potency and selectivity in lead optimization.

While the primary focus was the preparation of $K_v7$ agonists with a high selectivity for $K_v7.2/K_v7.3$ over $K_v7.4/K_v7.5$, this work also identified several analogs with significant selectivity for $K_v7.4/K_v7.5$ over $K_v7.2/K_v7.3$, i.e., an SI<1, such as RL-81 and RL-35. $K_v7.4$ is the primary potassium channel in the smooth muscle of the bladder, where it serves to regulate contractility. Activation of $K_v7.4$ leads to membrane hyperpolarization and a resultant loss of contractile function, a possible etiology for the urinary retention side effect of RG. While currently there is no clinical precedence for selective agonists of $K_v7.4$ and $K_v7.5$, other medicinal chemistry efforts toward this goal have been reported. Therefore, RL-81 and RL-35 could form the foundation for the development of more selective $K_v7.4/K_v7.5$ activators, with potential applications for treatment of visceral smooth muscle-related diseases, including irritable bowel syndrome and overactive bladder syndrome.

Example 3

Biological Activity of Additional Compounds

Biological data was obtained for several compounds, including compounds according to Formula I. The results are shown in FIGS. 6A and 6B. The evaluated compounds included:

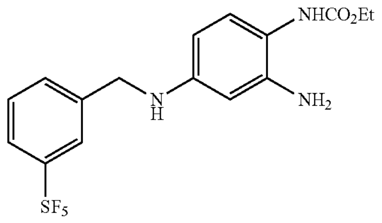

NR561.045 (2351785855)

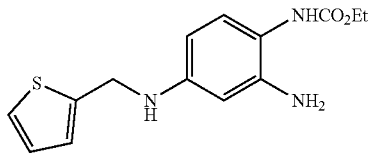

NR579.046 (2351785863)

-continued

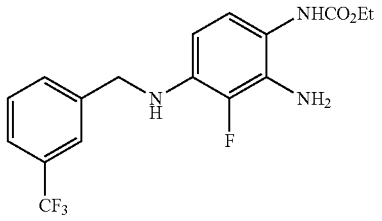

RL648.073 (2351785864)

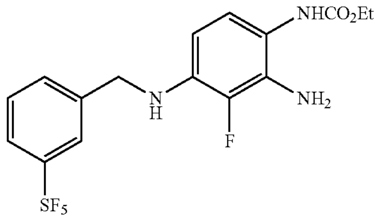

RL573.002 (2351785867)

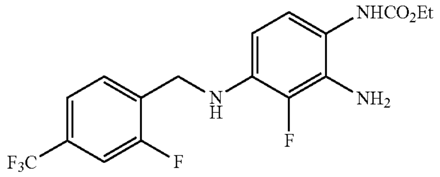

RL702.018 (2351785868)

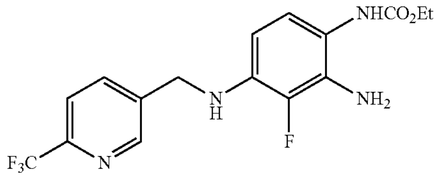

RL702.024 (2351785869)

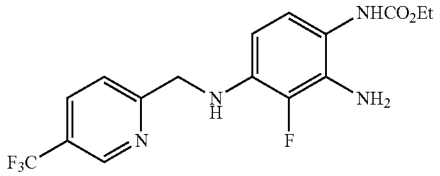

RL702.031 (2351785870)

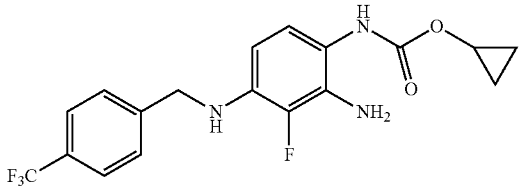

RL702.56 (23517857872)

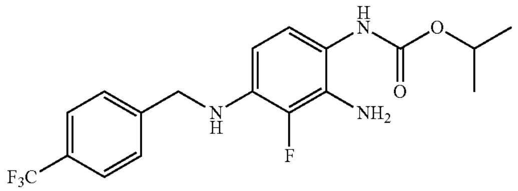

RL702.032 (23517857871)

-continued

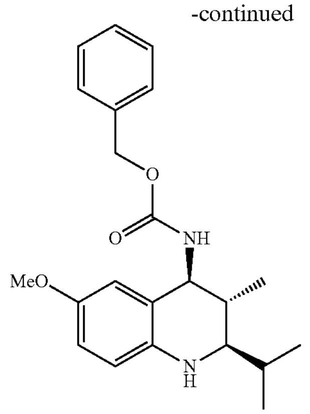

UPCMLD34AMZK041521 (2351363628)

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A compound, or a pharmaceutically acceptable salt thereof, having a formula I (I)

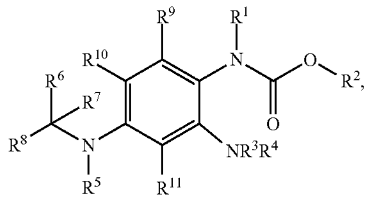

wherein:

$R^1$ is H or optionally-substituted alkyl;

$R^2$ is optionally-substituted cyclopropyl or optionally-substituted $C_1$-$C_6$ alkyl;

$R^3$ and $R^4$ are each independently H or optionally-substituted alkyl;

$R^5$ is H, optionally-substituted alkyl, acyl, or alkoxy-carbonyl;

$R^6$ and $R^7$ are each independently H, optionally-substituted alkyl, or $R^6$ and $R^7$ together form a carbocycle;

$R^8$ is substituted phenyl or optionally-substituted pyridinyl, provided that if $R^8$ is substituted phenyl, then $R^2$ is optionally-substituted cyclopropyl; and $R^9$, $R^{10}$ and $R^{11}$ are each independently H, halo, or optionally-substituted alkyl.

2. The compound according to claim 1, wherein:

(i) $R^1$ and $R^5$ are H;

(ii) $R^3$ and $R^4$ are H;

(iii) $R^7$ and $R^8$ are H; or (iv) any combination of (i), (ii), and (iii).

3. The compound according to claim 1, wherein $R^2$ is cyclopropyl or unsubstituted $C_1$-$C_6$ alkyl.

4. The compound according to claim 3, wherein $R^2$ is cyclopropyl or ethyl.

5. The compound according to claim 1, wherein $R^8$ is

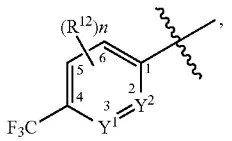

and wherein:

$Y^1$ and $Y^2$ independently are CH, CX where X is halo, N, or CCN, provided that at least one of $Y^1$ and $Y^2$ is CH or CX;

$R^{12}$ is halo or substituted sulfanyl; and n is 0, 1, or 2.

6. The compound according to claim 5 having a formula II:

(II)

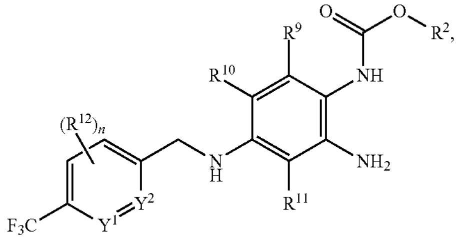

wherein if $Y^1$ and $Y^2$ independently are CH or CX, then $R^2$ is cyclopropyl.

7. The compound according to claim 5, wherein:

one of $Y^1$ and $Y^2$ is N;

the other of $Y^1$ and $Y^2$ is CH; and $R^2$ is cyclopropyl or ethyl.

8. The compound according to claim 5 wherein $Y^1$ and $Y^2$ independently are CH or CX, and the compound has a formula III (III)

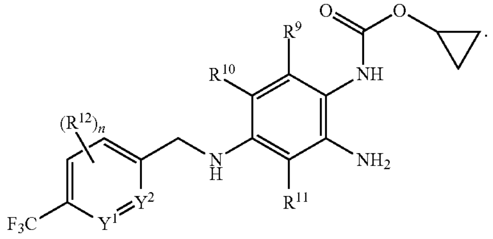

9. The compound according to claim 5, wherein n is 0 or 1.

10. The compound according to claim 9, wherein n is 1, $R^{12}$ is F, and $R^{12}$ is at the C6 position.

11. The compound according to claim 5, wherein n is 0.

12. The compound according to claim 1, wherein:

$R^9$ and $R^{10}$ independently are H, F, or haloalkyl; and $R^{11}$ is F.

13. The compound according to claim 1, wherein the compound is:

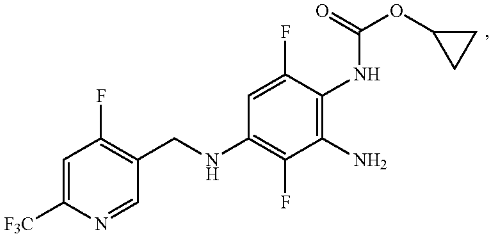
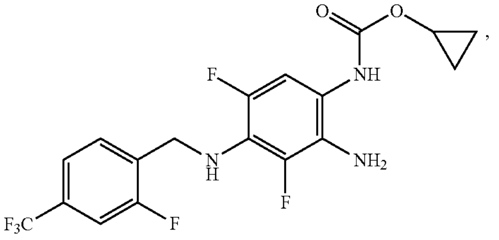
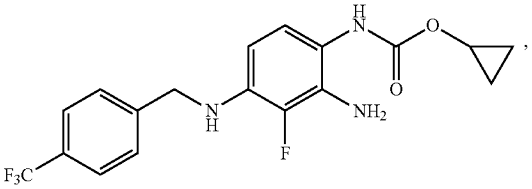
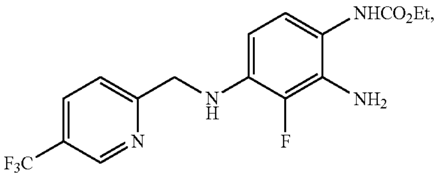
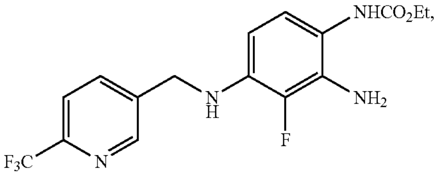
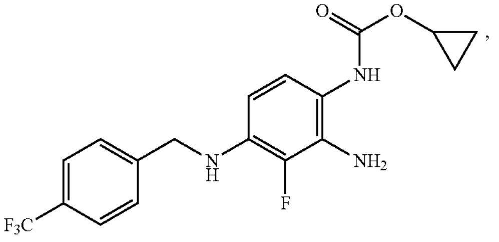
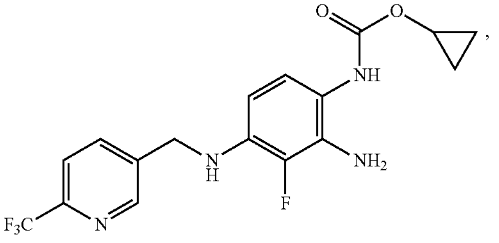
-continued
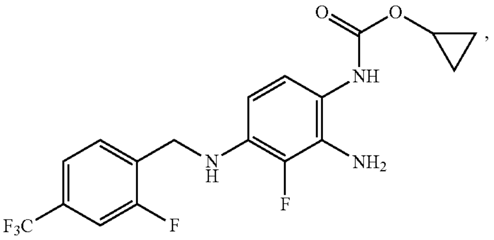
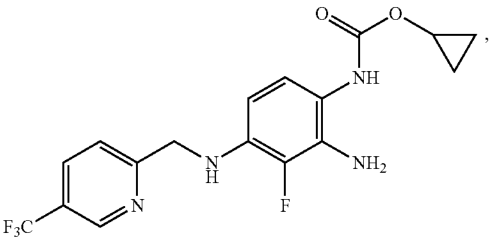
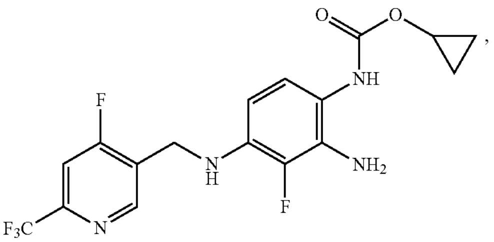
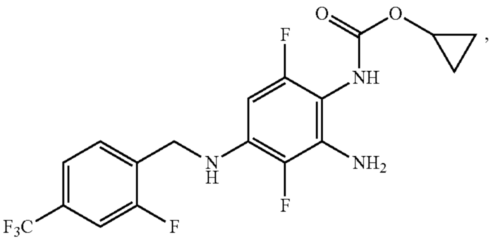
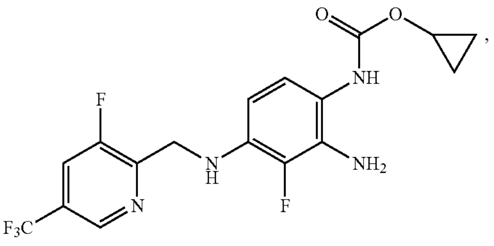
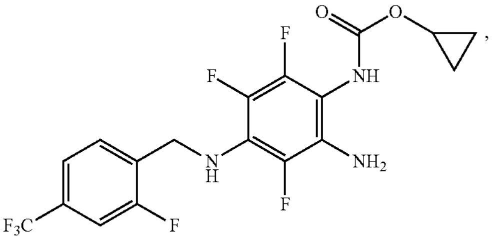

-continued

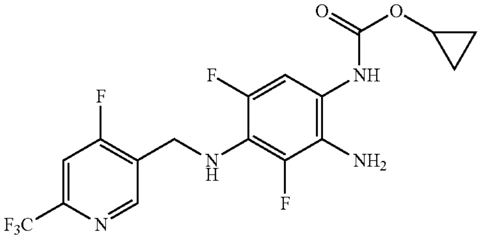

,

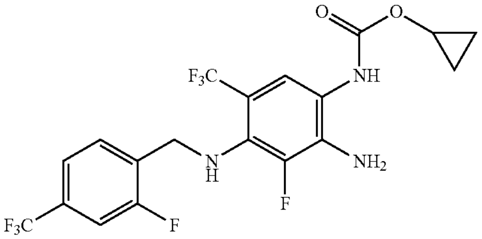

,

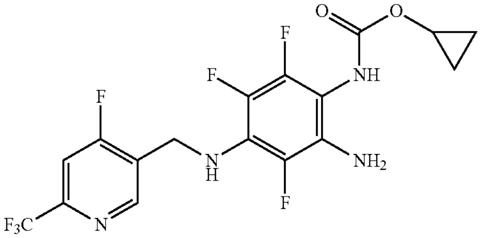

, or

-continued

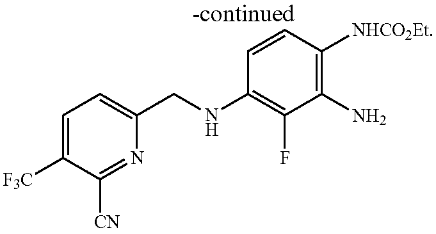

14. A pharmaceutical composition comprising at least one compound according to claim 1, and at least one pharmaceutically acceptable additive.

15. A method of activating a potassium channel, comprising contacting the potassium channel with an effective amount of at least one compound according to claim 1 or a pharmaceutical composition comprising the compound and at least one pharmaceutically acceptable additive.

16. The method of claim 15, wherein the potassium channel is KCNQ2/3.

17. The method of claim 15, wherein contacting the potassium channel with an effective amount of the compound or pharmaceutical composition comprises administering the effective amount of the compound or pharmaceutical composition to a subject.

18. A method of treating a subject suffering from or susceptible to tinnitus or epilepsy, comprising administering to the subject a therapeutically effective amount of at least one compound according to claim 1 or a pharmaceutical composition comprising the compound and at least one pharmaceutically acceptable additive.

* * * * *